(12) United States Patent
Espie et al.

(10) Patent No.: US 12,065,499 B2
(45) Date of Patent: Aug. 20, 2024

(54) ANTI-CD40 ANTIBODIES FOR USE IN TREATMENT OF SJÖGREN'S SYNDROME

(71) Applicant: Novartis AG, Basel (CH)

(72) Inventors: Pascal Espie, Saint Louis (FR); Peter Gergely, Oberwil (CH); James Rush, Thalwil (CH)

(73) Assignee: Novartis AG, Basel (CH)

( * ) Notice: Subject to any disclaimer, the term of this patent is extended or adjusted under 35 U.S.C. 154(b) by 280 days.

(21) Appl. No.: 16/177,689

(22) Filed: Nov. 1, 2018

(65) Prior Publication Data

US 2019/0153111 A1  May 23, 2019

Related U.S. Application Data

(60) Provisional application No. 62/644,939, filed on Mar. 19, 2018, provisional application No. 62/581,212, filed on Nov. 3, 2017.

(51) Int. Cl.

| | | |
|---|---|---|
| *C07K 16/28* | (2006.01) |
| *A61K 39/00* | (2006.01) |
| *A61K 39/395* | (2006.01) |
| *A61P 37/02* | (2006.01) |
| *A61P 37/06* | (2006.01) |

(52) U.S. Cl.
CPC .... *C07K 16/2878* (2013.01); *A61K 39/39591* (2013.01); *A61P 37/02* (2018.01); *A61P 37/06* (2018.01); *A61K 2039/505* (2013.01); *A61K 2039/54* (2013.01); *A61K 2039/545* (2013.01); *C07K 2317/21* (2013.01); *C07K 2317/33* (2013.01); *C07K 2317/52* (2013.01); *C07K 2317/71* (2013.01); *C07K 2317/76* (2013.01); *C07K 2317/77* (2013.01); *C07K 2317/92* (2013.01); *C07K 2317/94* (2013.01)

(58) Field of Classification Search
CPC ............ C07K 16/2878; C07K 2317/71; C07K 2317/76; C07K 2317/92; A61P 37/02; A61K 39/39591; A61K 2039/505
See application file for complete search history.

(56) References Cited

U.S. PATENT DOCUMENTS

| | | | |
|---|---|---|---|
| 8,568,725 B2 | 10/2013 | Takahashi et al. | |
| 8,591,900 B2 | 11/2013 | Barrett et al. | |
| 8,669,352 B2 | 3/2014 | den Hartog et al. | |
| 8,828,396 B2 * | 9/2014 | Heusser ............. | A61K 39/3955 424/153.1 |
| 9,221,913 B2 | 12/2015 | Heusser et al. | |
| 2010/0316636 A1 | 12/2010 | Radin et al. | |
| 2012/0121585 A1 * | 5/2012 | Heusser ............. | A61K 39/3955 424/133.1 |

FOREIGN PATENT DOCUMENTS

| | | |
|---|---|---|
| RU | 2014113304 | 10/2015 |
| WO | 2012045703 A1 | 4/2012 |
| WO | 2012065950 A1 | 5/2012 |
| WO | 013034904 | 3/2013 |
| WO | WO2013/164789 A2 | 11/2013 |
| WO | 2015112800 A1 | 7/2015 |
| WO | 2016081748 A2 | 5/2016 |
| WO | 2017059196 A2 | 4/2017 |
| WO | 2019087094 A1 | 5/2019 |

OTHER PUBLICATIONS

Fisher et al. The novel Anti-CD40 monoclonal antibody CFZ533 shows beneficial effects in patients with primary Sjogren's Syndrome: A Phase IIa Double Blind placebo controlled randomized trial. Abstract No. 1784. Meeting:2017 ACR/ARHP. Published Sep. 18, 2017. (Year: 2017).*
Fisher et al. Subcutaneous Dosing of the Novel ANTI-CD40 Antibody Iscalimab Achieves Target Drug Exposure and Clinical Efficacy in Primary Sjogren's Syndrome; Results of a Phase Iia randomised open label two are parallel group trial. 2019 (Year: 2019).*
Cordoba, F. et al. "A Novel, Blocking, Fc-Silent Anti-CD40 Monoclonal Antibody Prolongs Nonhuman Primate Renal Allograft Survival in the Absence of B Cell Depletion: Novel CD40 mAb Prolongs Allograft Survival", American Journal of Transplantation, vol. 15, No. 11, pp. 2825-2836, 2015.
Byrd, John C et al., "Phase I study of the anti-CD40 humanized monoclonal antibody lucatumumab (HCD122) in relapsed chronic lymphocytic leukemia", Leukemia and Lymphoma., vol. 53, No. 11, pp. 2136-2142, 2012.
Pers, Jacques-Olivier, et al: "Future treatments for Sjogren's syndrome", Presse Medical, vol. 45, No. 6, pp. e193-e200, Jun. 1, 2016.
Bombardieri et al., "Ectopic lymphoid neogenesis in rheumatic autoimmune diseases". Nat Rev Rheumatol. 13(3):141-154, 2017.
Bombardieri et al., "Inducible tertiary lymphoid structures, autoimmunity, and exocrine dysfunction in a novel model of salivary gland inflammation in C57BL/6 mice." J. Immunol. 189(7):3767-3776, 2012.
Bombardieri, "Ectopic lymphoid neogenesis and lymphoid chemokines in Sjogren's syndrome: at the interplay between chronic inflammation, autoimmunity and lymphomagenesis" Curr Pharm Biotechnol. 13(10):1989-1996, 2012.
Fisher et al., "The Novel Anti-CD40 Monoclonal Antibody CFZ533 Shows Beneficial Effects in Patients with Primary Sjögren's Syndrome: A Phase IIa Double-Blind, Placebo-Controlled Randomized Trial". ACR/ARHP annual meeting, Abstract No. 1784. 69(10), 2017.
Jacobi et al., "Analysis of immunoglobulin light chain rearrangements in the salivary gland and blood of a patient with Sjogren's syndrome" Arthritis Res 4(4):R4, 2002.

(Continued)

*Primary Examiner* — Amy E Juedes
*Assistant Examiner* — Brian Hartnett
(74) *Attorney, Agent, or Firm* — David Goetz

(57) ABSTRACT

The disclosure relates to methods, treatment regimens, uses, kits and therapies for treating Sjögren's syndrome, by employing anti-CD40 antibodies.

12 Claims, 27 Drawing Sheets

Specification includes a Sequence Listing.

(56) References Cited

OTHER PUBLICATIONS

Kaufman et al., "Sjögren's syndrome—not just Sicca: renal involvement in Sjögren's syndrome." Scand J Rheumatol. 37:213-8, 2008.
Komaroff et al., "Health status in patients with chronic fatigue syndrome and in general population and disease comparison groups." *Am J Med*. 101(3):281-90, 1996.
Kuenstner et al., "The comparability of quality of life scores. A multitrait multimethod analysis of the EORTC QLQ-C30, SF-36 and FLIC questionnaires". *Eur J Cancer* 38(3):339-48, 2002.
Papas et al., "Patient and investigator reported outcomes suggest improvements upon treatment with the novel anti-CD40 monoclonal antibody CFZ533 in patients with primary Sjogren's syndrome: a phase iia double-blind, placebo-controlled randomized trial" 36(3):251-252, 2018.
Segal et al., "Primary Sjögren's Syndrome: health experiences and predictors of health quality among patients in the United States" Health Qual Life Outcomes 7:46, 2009.
Slade et al., "Assessment of Safety, Pharmacokinetics and Pharmacodynamics of a Novel Anti-CD40 Monoclonal Antibody, CFZ533, in Healthy Volunteers and in Rheumatoid Arthritis Patients". ACR/ARHP annual meeting, Abstract No. 1582, 2016.
Stott et al., "Antigen-driven clonal proliferation of B cells within the target tissue of an autoimmune disease. The salivary glands of patients with Sjogren's syndrome" *J Clin Invest*.; 102(5):938-946, 1998.
Tishler et al., "Hydroxychloroquine treatment for primary Sjögren's syndrome: its effect. on salivary and serum inflammatory markers" *Ann Rheum Dis*. 58:253-6, 1999.
Voulgarelis, "Mucosa-associated lymphoid tissue lymphoma in Sjogren's syndrome: risks, management, and prognosis". *Rheum Dis Clin North Am*. 34(4):921-933, viii., 2008.
Winzer, "Use of methotrexate in patients with systemic lupus erythematosus and primary Sjögren's syndrome" *Clin Exp Rheumatol*. 28 (5 Suppl 61):S156-9, 2010.
Clinicaltrials.gov publication NCT02291029, weblink: https://clinicaltrials.gov/ct2/show/NCT02291029?cond=cfz533&rank=2, Jan. 10, 2019.
Wang et al., "IgG Fc Engineering to Modulate Antibody Effector Functions," Protein Cell, 2018, vol. 9, No. 1, pp. 63-73.
Musselli C. et al., "BIIB063, a Potent Anti-CD40 Antagonistic Monoclonal Antibody (MAb): Lessons Learned From an Early Development Program," Arthritis & Rheumatology, Sep. 18, 2017, vol. 69 Suppl. 10, Abstract No. 45.
Ristov J. et al., "Characterization of the in Vitro and in Vivo Properties of CFZ533, a Blocking and Non-Depleting anti-CD40 Monoclonal Antibody", American Journal of Transplantation, May 24, 2018, vol. 18, pp. 2895-2904.

\* cited by examiner

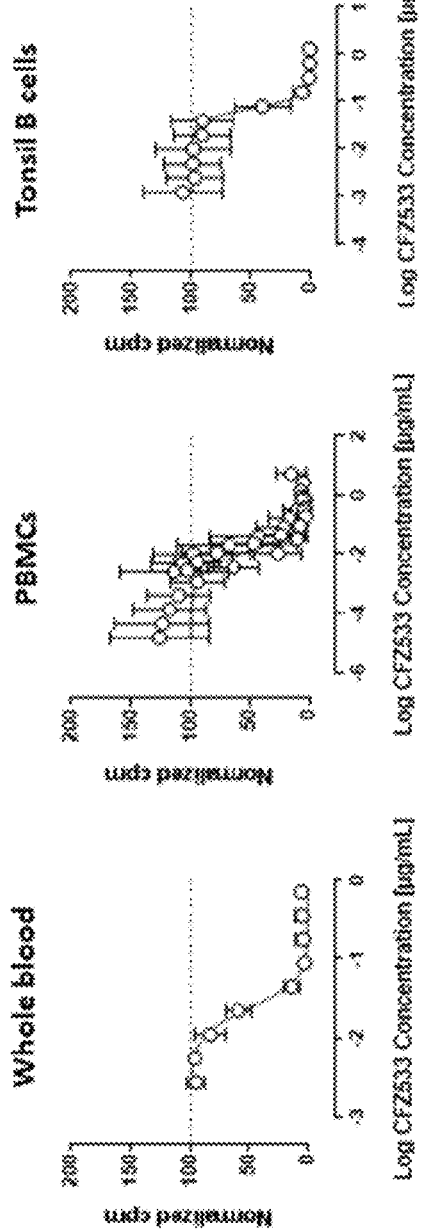
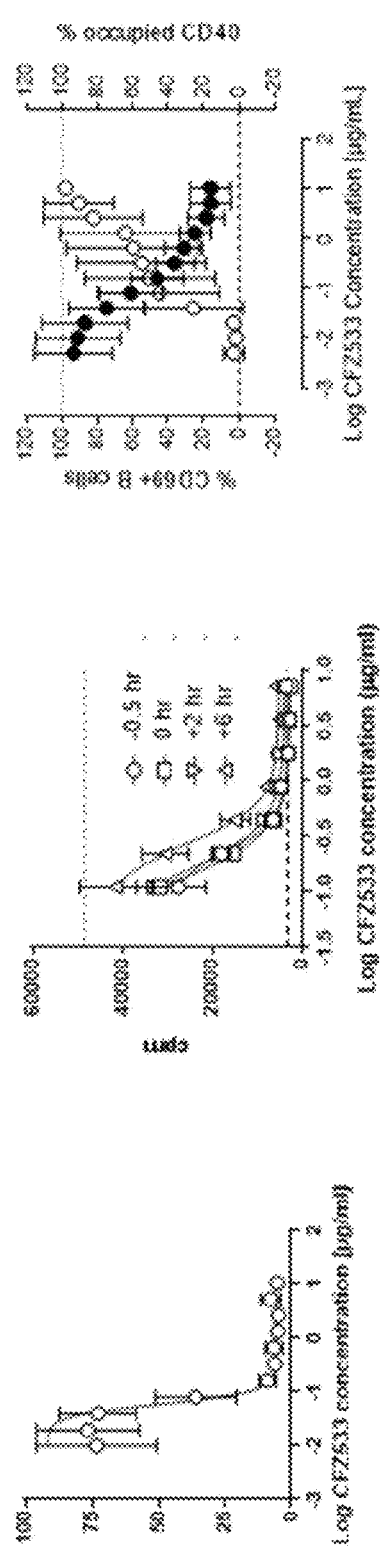
FIG 18A, FIG 18B, FIG 18C, FIG 18D

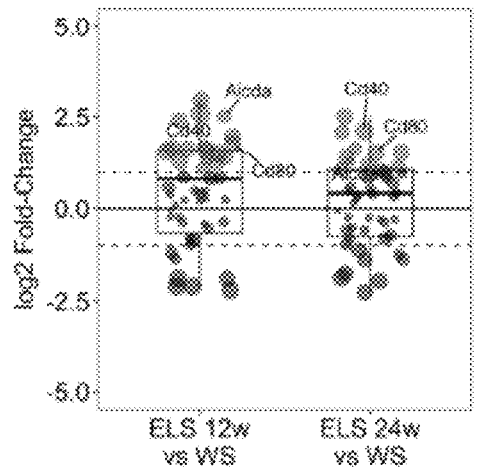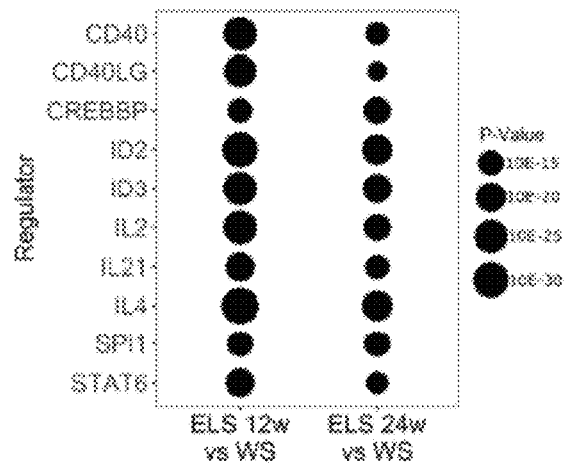
FIG 26A
FIG 26B
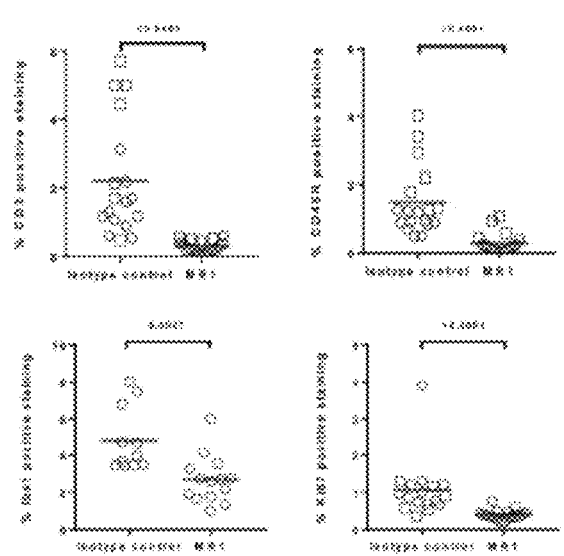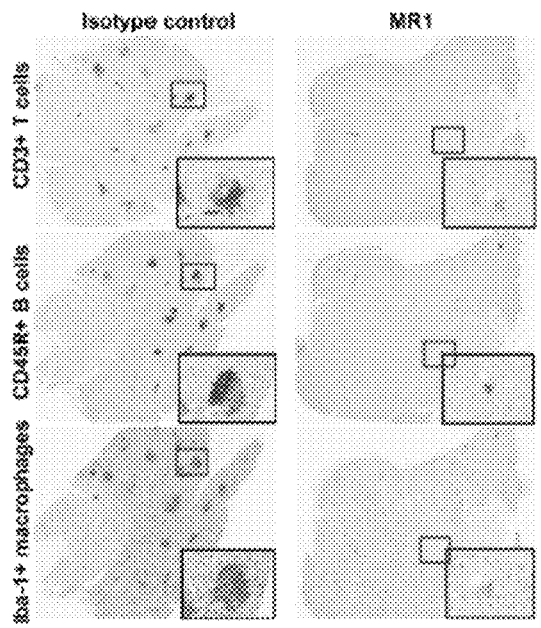
FIG 26C
FIG 26D

```
SEQUENCE LISTING

<160> NUMBER OF SEQ ID NOS: 19

<210> SEQ ID NO 1
<211> LENGTH: 5
<212> TYPE: PRT
<213> ORGANISM: Homo sapiens

<400> SEQUENCE: 1

Ser Tyr Gly Met His
1               5

<210> SEQ ID NO 2
<211> LENGTH: 17
<212> TYPE: PRT
<213> ORGANISM: Homo sapiens

<400> SEQUENCE: 2

Val Ile Ser Tyr Glu Glu Ser Asn Arg Tyr His Ala Asp Ser Val Lys
1               5                   10                  15

Gly

<210> SEQ ID NO 3
<211> LENGTH: 11
<212> TYPE: PRT
<213> ORGANISM: Homo Sapiens

<400> SEQUENCE: 3

Asp Gly Gly Ile Ala Ala Pro Gly Pro Asp Tyr
1               5                   10

<210> SEQ ID NO 4
<211> LENGTH: 16
<212> TYPE: PRT
<213> ORGANISM: Homo sapiens

<400> SEQUENCE: 4
```

Arg Ser Ser Gln Ser Leu Leu Tyr Ser Asn Gly Tyr Asn Tyr Leu Asp
1               5                   10                  15

<210> SEQ ID NO 5
<211> LENGTH: 7
<212> TYPE: PRT
<213> ORGANISM: Homo sapiens

<400> SEQUENCE: 5

Leu Gly Ser Asn Arg Ala Ser
1               5

<210> SEQ ID NO 6
<211> LENGTH: 9
<212> TYPE: PRT
<213> ORGANISM: Homo sapiens

<400> SEQUENCE: 6

Met Gln Ala Arg Gln Thr Pro Phe Thr
1               5

<210> SEQ ID NO 7
<211> LENGTH: 120
<212> TYPE: PRT
<213> ORGANISM: Homo sapiens

<400> SEQUENCE: 7

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Glu Glu Ser Asn Arg Tyr His Ala Asp Ser Val
    50                  55                  60

Lys Gly Arg Phe Thr Ile Ser Arg Asp Asn Ser Lys Ile Thr Leu Tyr
65                  70                  75                  80

Leu Gln Met Asn Ser Leu Arg Thr Glu Asp Thr Ala Val Tyr Tyr Cys
                85                  90                  95

Ala Arg Asp Gly Gly Ile Ala Ala Pro Gly Pro Asp Tyr Trp Gly Gln
            100                 105                 110

Gly Thr Leu Val Thr Val Ser Ser
        115                 120

<210> SEQ ID NO 8
<211> LENGTH: 112
<212> TYPE: PRT
<213> ORGANISM: Homo sapeins

<400> SEQUENCE: 8

Asp Ile Val Met Thr Gln Ser Pro Leu Ser Leu Thr Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Val Leu Ile Ser Leu Gly Ser Asn Arg Ala Ser Gly Val Pro
    50                  55                  60

Asp Arg Phe Ser Gly Ser Gly Ser Gly Thr Asp Phe Thr Leu Lys Ile

```
                65                  70                  75                  80

Ser Arg Val Glu Ala Glu Asp Val Gly Val Tyr Tyr Cys Met Gln Ala
                    85                  90                  95

Arg Gln Thr Pro Phe Thr Phe Gly Pro Gly Thr Lys Val Asp Ile Arg
                100                 105                 110

<210> SEQ ID NO 9
<211> LENGTH: 450
<212> TYPE: PRT
<213> ORGANISM: Homo sapiens

<400> SEQUENCE: 9

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Glu Glu Ser Asn Arg Tyr His Ala Asp Ser Val
        50                  55                  60

Lys Gly Arg Phe Thr Ile Ser Arg Asp Asn Ser Lys Ile Thr Leu Tyr
65                  70                  75                  80

Leu Gln Met Asn Ser Leu Arg Thr Glu Asp Thr Ala Val Tyr Tyr Cys
                85                  90                  95

Ala Arg Asp Gly Gly Ile Ala Ala Pro Gly Pro Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335
```

```
Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 10
<211> LENGTH: 219
<212> TYPE: PRT
<213> ORGANISM: Homo sapiens

<400> SEQUENCE: 10

Asp Ile Val Met Thr Gln Ser Pro Leu Ser Leu Thr Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Val Leu Ile Ser Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Gln Thr Pro Phe Thr Phe Gly Pro Gly Thr Lys Val Asp Ile Arg
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 11
<211> LENGTH: 450
<212> TYPE: PRT
<213> ORGANISM: Homo sapiens
```

<400> SEQUENCE: 11

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Glu Glu Ser Asn Arg Tyr His Ala Asp Ser Val
    50                  55                  60

Lys Gly Arg Phe Thr Ile Ser Arg Asp Asn Ser Lys Ile Thr Leu Tyr
65                  70                  75                  80

Leu Gln Met Asn Ser Leu Arg Thr Glu Asp Thr Ala Val Tyr Tyr Cys
                85                  90                  95

Ala Arg Asp Gly Gly Ile Ala Ala Pro Gly Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Ala Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
```

405                 410                 415
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 12
<211> LENGTH: 219
<212> TYPE: PRT
<213> ORGANISM: Homo sapiens

<400> SEQUENCE: 12

Asp Ile Val Met Thr Gln Ser Pro Leu Ser Leu Thr Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Val Leu Ile Ser Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Gln Thr Pro Phe Thr Phe Gly Pro Gly Thr Lys Val Asp Ile Arg
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 13
<211> LENGTH: 217
<212> TYPE: PRT
<213> ORGANISM: Homo sapiens

<400> SEQUENCE: 13

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu

```
            50                  55                  60
Gln Tyr Ala Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Arg Glu Glu Met
            115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 14
<211> LENGTH: 217
<212> TYPE: PRT
<213> ORGANISM: Homo sapiens

<400> SEQUENCE: 14

Ala Pro Glu Leu Leu Gly Gly Pro Ser Val Phe Leu Phe Pro Pro Lys
  1               5                  10                  15

Pro Lys Asp Thr Leu Met Ile Ser Arg Thr Pro Glu Val Thr Cys Val
                 20                  25                  30

Val Val Ala Val Ser His Glu Asp Pro Glu Val Lys Phe Asn Trp Tyr
             35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Arg Glu Glu Met
            115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205
```

Lys Ser Leu Ser Leu Ser Pro Gly Lys
    210                 215

<210> SEQ ID NO 15
<211> LENGTH: 1350
<212> TYPE: DNA
<213> ORGANISM: Homo sapiens

<400> SEQUENCE: 15

| | | | | |
|---|---|---|---|---|
| caggtgcagc tggtggaatc tggcggcgga gtggtgcagc tggccggtc cctgagactg | | | | 60 |
| tcttgcgccg cctccggctt caccttctcc agctacggca tgcactgggt gcgacaggcc | | | | 120 |
| cctggcaagg gactggaatg ggtggccgtg atctcctacg aggaatccaa cagataccac | | | | 180 |
| gctgactccg tgaagggccg gttcacaatc tcccgggaca actccaagat caccctgtac | | | | 240 |
| ctgcagatga actccctgcg gaccgaggac accgccgtgt actactgcgc cagggacgga | | | | 300 |
| ggaatcgccg ctcctggacc tgattattgg ggccagggca cctggtgac agtgtcctcc | | | | 360 |
| gctagcacca agggcccctc cgtgttccct ctggccccct ccagcaagtc cacctctggc | | | | 420 |
| ggcaccgccg ctctgggctg cctggtgaaa gactacttcc ccgagcccgt gaccgtgtcc | | | | 480 |
| tggaactctg gcgccctgac ctccggcgtg cacacctttc cagccgtgct gcagtcctcc | | | | 540 |
| ggcctgtact ccctgtcctc cgtggtgacc gtgccctcta gctctctggg cacccagacc | | | | 600 |
| tacatctgca acgtgaacca caagccctcc aacaccaagg tggacaagcg ggtggaaccc | | | | 660 |
| aagtcctgcg acaagaccca cacctgtccc cctgccctg cccctgaact gctgggcgga | | | | 720 |
| ccttccgtgt tcctgttccc cccaaagccc aaggacaccc tgatgatctc ccggaccccc | | | | 780 |
| gaagtgacct gcgtggtggt ggacgtgtcc cacgaggacc ctgaagtgaa gttcaattgg | | | | 840 |
| tacgtggacg gcgtggaagt gcacaacgcc aagaccaagc ccagagagga cagtacgcc | | | | 900 |
| tccaccctacc gggtggtgtc tgtgctgacc gtgctgcacc aggactggct gaacggcaaa | | | | 960 |
| gagtacaagt gcaaggtctc caacaaggcc ctgcctgccc catcgaaaa gaccatctcc | | | | 1020 |
| aaggccaagg ccagccccg cgagccacag gtgtacacac tgcccccag ccgggaagag | | | | 1080 |
| atgaccaaga accaggtgtc cctgacctgt ctggtcaaag gcttctaccc ctccgatatc | | | | 1140 |
| gccgtggagt gggagtccaa cggacagccc gagaacaact acaagaccac ccccctgtg | | | | 1200 |
| ctggactccg acggctcatt cttcctgtac tccaagctga ccgtggacaa gtcccggtgg | | | | 1260 |
| cagcagggca acgtgttctc ctgctccgtg atgcacgagg ccctgcacaa ccactacacc | | | | 1320 |
| cagaagtccc tgtccctgag ccccggcaag | | | | 1350 |

<210> SEQ ID NO 16
<211> LENGTH: 657
<212> TYPE: DNA
<213> ORGANISM: Homo sapiens

<400> SEQUENCE: 16

| | | | | |
|---|---|---|---|---|
| gacatcgtga tgacccagtc ccccctgtcc ctgaccgtga cacctggcga gcctgcctct | | | | 60 |
| atctcctgca gatcctccca gtccctgctg tactccaacg gctacaacta cctggactgg | | | | 120 |
| tatctgcaga agcccggcca gtccccacag gtgctgatct ccctgggctc caacagagcc | | | | 180 |
| tctggcgtgc ccgaccggtt ctccggctct ggctctggca ccgacttcac actgaagatc | | | | 240 |
| tcacgggtgg aagccgagga cgtgggcgtg tactactgca tgcaggcccg gcagaccccc | | | | 300 |
| ttcaccttcg gccctggcac caaggtggac atcggcgta cggtggccgc tcccagcgtg | | | | 360 |
| ttcatcttcc cccccagcga cgagcagctg aagagcggca ccgccagcgt ggtgtgcctg | | | | 420 |

| | |
|---|---|
| ctgaacaact tctaccccccg ggaggccaag gtgcagtgga aggtggacaa cgccctgcag | 480 |
| agcggcaaca gccaggagag cgtcaccgag caggacagca aggactccac ctacagcctg | 540 |
| agcagcaccc tgaccctgag caaggccgac tacgagaagc ataaggtgta cgcctgcgag | 600 |
| gtgacccacc agggcctgtc cagccccgtg accaagagct caacaggggg cgagtgc | 657 |

<210> SEQ ID NO 17
<211> LENGTH: 1350
<212> TYPE: DNA
<213> ORGANISM: Homo sapiens

<400> SEQUENCE: 17

| | |
|---|---|
| caggtgcagc tggtggaatc tggcggcgga gtggtgcagc tggccggtc cctgagactg | 60 |
| tcttgcgccg cctccggctt caccttctcc agctacggca tgcactgggt gcgacaggcc | 120 |
| cctggcaagg gactggaatg ggtggccgtg atctcctacg aggaatccaa cagataccac | 180 |
| gctgactccg tgaagggccg gttcacaatc tcccgggaca actccaagat caccctgtac | 240 |
| ctgcagatga actccctgcg gaccgaggac accgccgtgt actactgcgc cagggacgga | 300 |
| ggaatcgccg ctcctggacc tgattattgg ggccagggca ccctggtgac agtgtcctcc | 360 |
| gctagcacca agggcccctc cgtgttccct ctggccccct ccagcaagtc cacctctggc | 420 |
| ggcaccgccg ctctgggctg cctggtgaaa gactacttcc ccgagcccgt gaccgtgtcc | 480 |
| tggaactctg gcgccctgac ctccggcgtg cacacctttc cagccgtgct gcagtcctcc | 540 |
| ggcctgtact ccctgtcctc cgtggtgacc gtgccctcta gctctctggg cacccagacc | 600 |
| tacatctgca acgtgaacca caagccctcc aacaccaagg tggacaagcg gtggaaccc | 660 |
| aagtcctgcg acaagaccca cacctgtccc cctgccctg cccctgaact gctgggcgga | 720 |
| ccttccgtgt tcctgttccc cccaaagccc aaggacaccc tgatgatctc ccggacccc | 780 |
| gaagtgacct gcgtggtggt ggccgtgtcc cacgaggacc ctgaagtgaa gttcaattgg | 840 |
| tacgtggacg gcgtggaagt gcacaacgcc aagaccaagc ccagagagga acagtacaac | 900 |
| tccacctacc gggtggtgtc tgtgctgacc gtgctgcacc aggactggct gaacggcaaa | 960 |
| gagtacaagt gcaaggtctc caacaaggcc ctgcctgccc catcgaaaa gaccatctcc | 1020 |
| aaggccaagg gccagccccg cgagccacag gtgtacacac tgcccccag ccgggaagag | 1080 |
| atgaccaaga accaggtgtc cctgacctgt ctggtcaaag gcttctaccc ctccgatatc | 1140 |
| gccgtggagt gggagtccaa cggacagccc gagaacaact acaagaccac ccccctgtg | 1200 |
| ctggactccg acggctcatt cttcctgtac tccaagctga ccgtggacaa gtcccggtgg | 1260 |
| cagcagggca acgtgttctc ctgctccgtg atgcacgagg ccctgcacaa ccactacacc | 1320 |
| cagaagtccc tgtccctgag ccccggcaag | 1350 |

<210> SEQ ID NO 18
<211> LENGTH: 657
<212> TYPE: DNA
<213> ORGANISM: Homo sapiens

<400> SEQUENCE: 18

| | |
|---|---|
| gacatcgtga tgacccagtc ccccctgtcc ctgaccgtga cacctggcga gcctgcctct | 60 |
| atctcctgca gatcctccca gtccctgctg tactccaacg gctacaacta cctggactgg | 120 |
| tatctgcaga agcccggcca gtccccacag gtgctgatct ccctgggctc caacagagcc | 180 |
| tctggcgtgc ccgaccggtt ctccggctct ggctctggca ccgacttcac actgaagatc | 240 |
| tcacggggtg aagccgagga cgtgggcgtg tactactgca tgcaggcccg gcagaccccc | 300 |

```
ttcaccttcg gccctggcac caaggtggac atccggcgta cggtggccgc tcccagcgtg    360
ttcatcttcc cccccagcga cgagcagctg aagagcggca ccgccagcgt ggtgtgcctg    420
ctgaacaact tctaccccg ggaggccaag gtgcagtgga aggtggacaa cgccctgcag    480
agcggcaaca gccaggagag cgtcaccgag caggacagca aggactccac ctacagcctg    540
agcagcaccc tgaccctgag caaggccgac tacgagaagc ataaggtgta cgcctgcgag    600
gtgacccacc agggcctgtc cagccccgtg accaagagct tcaacagggg cgagtgc      657
```

<210> SEQ ID NO 19
<211> LENGTH: 277
<212> TYPE: PRT
<213> ORGANISM: Homo sapiens

<400> SEQUENCE: 19

```
Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
        275
```

ANTI-CD40 ANTIBODIES FOR USE IN TREATMENT OF SJÖGREN'S SYNDROME

PREVIOUS APPLICATIONS

This application claims priority to U.S. provisional application No. 62/581,212, filed 3 Nov. 2017 and U.S. provisional application No. 62/644,939, filed 19 Mar. 2018, the contents of which are included in their entirety.

TECHNICAL FIELD

The disclosure relates to methods, treatment regimens, uses, kits and therapies for treating Sjögren's syndrome, such as primary Sjögren's syndrome or secondary Sjögren's syndrome, by employing anti-CD40 antibodies, such as CFZ533.

BACKGROUND OF THE DISCLOSURE

Sjögren's syndrome (SS), such as primary Sjögren's syndrome (pSS) or secondary Sjögren's syndrome (sSS) is a common chronic autoimmune disease of unknown etiology.

Hallmarks of the disease in both primary and secondary SS patients include the presence of anti-Ro and anti-La autoantibodies as well as mononuclear cell infiltrates in salivary and lacrimal glands (Bombardieri, et al. 2012). In some instances, these accumulations of T and B lymphocytes form well-organized structures referred to as ectopic lymphoid structures (ELS) that bear morphological and functional similarities to GCs (Voulgarelis et al. 2008). Previous work has reported evidence of ELS in salivary glands from SS patients and from preclinical models of this disease and evidence of ongoing affinity maturation (Jacobi et al. 2002; Stott et al. 1998; Bombardieri et al. 2012), implicating these structures in disease pathology (Bombardieri et al. 2017).

The impact of this disease on quality of life (QoL) measures is substantial and comparative studies indicated that pSS QoL scored quantitatively worse than congestive heart failure or many cancers (Segal et al 2009; Kuenstner et al 2002; Komaroff et al 1996). Moreover, increased B cell activity in SS results in an increased risk for malignant transformation with lymphoma development occurring in 5% of SS patients. Treatment for SS patients is limited to symptomatic care for the mucosal signs and symptoms, and to date no evidence-based, systemic therapy has been available for SS patients.

Glucocorticoids and typical disease-modifying anti-rheumatic drugs (DMARDs) are mostly ineffective, and no pharmacologic intervention is effective against the severe, disabling fatigue. Despite a lack of convincing evidence of efficacy and based on anecdotal evidence as well as experience from similar autoimmune diseases such as systemic lupus erythematosus, antimalarials (Tishler et al 2008), methotrexate (Winzer and Aringer 2010) or azathioprine (Kaufman et al 1999) are sometimes used, in particular for the treatment of extraglandular symptoms such as renal or joint involvement.

Although small trials with the B cell depleting agent rituximab have demonstrated a degree of therapeutic efficacy, no proper, large randomized controlled trials have shown clear efficacy with regard to extra-glandular and glandular disease manifestations. A disease modifying agent that prevents secretory gland destruction and addresses extra-glandular disease manifestations would introduce a game-changing advance for the treatment of SS, such as chronic pSS.

CFZ533 is a human monoclonal antibody directed against human CD40. It belongs to the IgG1 isotype subclass with and comprises an Fc-silencing mutation (N297A) which abolishes FcγR binding and associated effector functions like ADCC and CDC. CFZ533 is disclosed in U.S. Pat. Nos. 8,828,396 and 9,221,913, incorporated herein by reference.

SUMMARY OF THE DISCLOSURE

It has been found that human, anti-CD40 monoclonal antibodies with silenced ADCC activity are suitable for the treatment of Sjögren's syndrome. Particularly, the antibody CFZ533 has in a proof of concept study shown promise of offering a new treatment modality in clinically active pSS.

According to a first aspect of the invention an anti-CD40 antibody for use in the treatment of Sjögren's syndrome is provided. In one embodiment, Sjögren's syndrome is primary Sjögren's syndrome.

The antibody may be selected from the group consisting of:
a. an anti-CD40 antibody comprising an immunoglobulin VH domain comprising the amino acid sequence of SEQ ID NO: 7 and an immunoglobulin VL domain comprising the amino acid sequence of SEQ ID NO: 8;
b. an anti-CD40 antibody comprising an immunoglobulin VH domain comprising the hypervariable regions set forth as SEQ ID NO: 1, SEQ ID NO: 2, and SEQ ID NO: 3 and an immunoglobulin VL domain comprising the hypervariable regions set forth as SEQ ID NO: 4, SEQ ID NO: 5 and SEQ ID NO: 6;
c. an anti-CD40 antibody comprising an immunoglobulin VH domain comprising the amino acid sequence of SEQ ID NO: 7 and an immunoglobulin VL domain comprising the amino acid sequence of SEQ ID NO: 8, and an Fc region of SEQ ID NO: 13;
d. an anti-CD40 antibody comprising an immunoglobulin VH domain comprising the amino acid sequence of SEQ ID NO: 7 and an immunoglobulin VL domain comprising the amino acid sequence of SEQ ID NO: 8, and an Fc region of SEQ ID NO: 14; and
e. an anti-CD40 antibody comprising a silent Fc IgG1 region.

The antibody may comprises the heavy chain amino acid sequence of SEQ ID NO: 9 and the light chain amino acid sequence of SEQ ID NO: 10; or the heavy chain amino acid sequence of SEQ ID NO: 11 and the light chain amino acid sequence of SEQ ID NO: 12.

In one embodiment, a pharmaceutical composition is provided comprising a therapeutically effective amount of the antibody for use according the first aspect and one or more pharmaceutically acceptable carriers.

In one embodiment, the route of administration is subcutaneous or intravenous of the antibody according to the first aspect, or a combination of subcutaneous or intravenous.

The dose may be about 3 mg to about 30 mg active ingredient per kilogram of a human subject. The dose may be given weekly, every two weeks or every four weeks.

In one embodiment, the dose is about 10 mg active ingredient per kilogram of a human subject.

In one embodiment, the dose is about 150 mg to about 600 mg active ingredient. The dose may be given weekly, every two weeks or every four weeks.

In one embodiment, the dose is about 300 mg active ingredient.

In one preferred embodiment, the dose is 150 mg active ingredient. In another preferred embodiment, the dose is 300 mg active ingredient. In yet another preferred embodiment, the dose is 600 mg active ingredient.

In one embodiment, the antibody is administered through a loading dosing and a maintenance dosing.

In one embodiment, the loading dosing is administered via subcutaneous injections of a first dose and the maintenance dosing is administered via subcutaneous injections of a second dose. The first dose may be the same as the second dose or higher than the second dose.

In one embodiment, the first dose is between about 150 mg and about 600 mg active ingredient, such as about 300 mg active ingredient and the second dose is between about 150 mg and about 600 mg active ingredient, such as about 300 mg active ingredient.

In one embodiment, the first dose is 150 mg, 300 mg or 600 mg active ingredient and the second dose is 150 mg, 300 mg or 600 mg active ingredient.

In one embodiment, the loading dosing comprises at least two subcutaneous injections and the maintenance dosing consists of weekly (Q1W), biweekly (Q2W) or monthly (Q4W) subcutaneous injections. In one embodiment, the loading dosing consists of two subcutaneous injections. In another embodiment, the loading dosing consists of three subcutaneous injections.

In one embodiment, the subcutaneous injections of the loading dosing are different doses. In another embodiment, the subcutaneous injections of the loading dosing are the same dose.

According to a second aspect, a method of treating Sjögren's syndrome in a human subject is provided, comprising administering a therapeutically effective dose of anti-CD40 antibody to said subject. In a preferred embodiment, the Sjögren's syndrome is primary Sjögren's syndrome.

In one embodiment the antibody is selected from the group consisting of:
  a. an anti-CD40 antibody comprising an immunoglobulin VH domain comprising the amino acid sequence of SEQ ID NO: 7 and an immunoglobulin VL domain comprising the amino acid sequence of SEQ ID NO: 8;
  b. an anti-CD40 antibody comprising an immunoglobulin VH domain comprising the hypervariable regions set forth as SEQ ID NO: 1, SEQ ID NO: 2, and SEQ ID NO: 3 and an immunoglobulin VL domain comprising the hypervariable regions set forth as SEQ ID NO: 4, SEQ ID NO: 5 and SEQ ID NO: 6;
  c. an anti-CD40 antibody comprising an immunoglobulin VH domain comprising the amino acid sequence of SEQ ID NO: 7 and an immunoglobulin VL domain comprising the amino acid sequence of SEQ ID NO: 8, and an Fc region of SEQ ID NO: 13;
  d. an anti-CD40 antibody comprising an immunoglobulin VH domain comprising the amino acid sequence of SEQ ID NO: 7 and an immunoglobulin VL domain comprising the amino acid sequence of SEQ ID NO: 8, and an Fc region of SEQ ID NO: 14; and
  e. an anti-CD40 antibody comprising a silent Fc IgG1 region.

In one embodiment, the antibody comprises the heavy chain amino acid sequence of SEQ ID NO: 9 and the light chain amino acid sequence of SEQ ID NO: 10; or the heavy chain amino acid sequence of SEQ ID NO: 11 and the light chain amino acid sequence of SEQ ID NO: 12.

In one embodiment, the antibody is administered together with one or more pharmaceutically acceptable carriers.

In one embodiment, the antibody is administered subcutaneously or intravenously, or a combination of subcutaneous or intravenous.

In one embodiment, the antibody is administered as a dose of about 3 mg to about 30 mg active ingredient per kilogram of a human subject.

In one embodiment, the dose is about 10 mg active ingredient per kilogram of the human subject.

In one embodiment, the antibody is administered as a dose of about 150 mg to about 600 mg active ingredient, such as 300 mg active ingredient.

In one preferred embodiment, the dose is 150 mg active ingredient. In another preferred embodiment, the dose is 300 mg active ingredient. In yet another preferred embodiment, the dose is 600 mg active ingredient.

In one embodiment, the antibody is administered with a loading dosing and a maintenance dosing.

In one embodiment, the loading dosing is administered via subcutaneous injections of a first dose and the maintenance dosing is administered via subcutaneous injections of a second dose.

The first dose may be the same as the second dose or higher than the second dose.

In one embodiment, the first dose is between about 150 mg and about 600 mg active ingredient, such as about 300 mg active ingredient and the second dose is between about 150 mg and about 600 mg active ingredient, such as about 300 mg active ingredient.

In one embodiment, the first dose is 150 mg, 300 mg or 600 mg active ingredient and the second dose is 150 mg, 300 mg or 600 mg active ingredient.

In one embodiment, the loading dosing comprises at least two subcutaneous injections and the maintenance dosing consists of weekly (Q1W), biweekly (Q2W) or monthly (Q4W) subcutaneous injections.

In one embodiment, the loading dosing consists of two subcutaneous injections. In another embodiment, the loading dosing consists of three subcutaneous injections In one embodiment, the subcutaneous injections of the loading dosing are different doses. In another embodiment, the subcutaneous injections of the loading dosing are the same dose.

According to a third aspect, use of a liquid pharmaceutical composition comprising an anti-CD40 antibody, a buffer, a stabilizer and a solubilizer, and means for subcutaneously administering the anti-CD40 antibody to a patient having Sjögren's syndrome, for the manufacture of a medicament for the treatment of Sjögren's syndrome is provided, wherein the anti-CD40 antibody:
  a. is to be subcutaneously administered with a first loading dosing; and
  b. thereafter, with a second maintenance dosing, wherein said anti-CD40 antibody is selected from the group consisting of:
    i. an anti-CD40 antibody comprising an immunoglobulin VH domain comprising the amino acid sequence of SEQ ID NO: 7 and an immunoglobulin VL domain comprising the amino acid sequence of SEQ ID NO: 8;
    ii. an anti-CD40 antibody comprising an immunoglobulin VH domain comprising the hypervariable regions set forth as SEQ ID NO: 1, SEQ ID NO: 2, and SEQ ID NO: 3 and an immunoglobulin VL domain comprising the hypervariable regions set forth as SEQ ID NO: 4, SEQ ID NO: 5 and SEQ ID NO: 6;
    iii. an anti-CD40 antibody comprising an immunoglobulin VH domain comprising the amino acid sequence of SEQ ID NO: 7 and an immunoglobulin VL domain comprising the amino acid sequence of SEQ ID NO: 8, and an Fc region of SEQ ID NO: 13;
iv. an anti-CD40 antibody comprising an immunoglobulin VH domain comprising the amino acid sequence of SEQ ID NO: 7 and an immunoglobulin VL domain comprising the amino acid sequence of SEQ ID NO: 8, and an Fc region of SEQ ID NO: 14;
v. an anti-CD40 antibody comprising a silent Fc IgG1 region: and
vi. an anti-CD40 antibody comprising the heavy chain amino acid sequence of SEQ ID NO: 9 and the light chain amino acid sequence of SEQ ID NO: 10; or the heavy chain amino acid sequence of SEQ ID NO: 11 and the light chain amino acid sequence of SEQ ID NO: 12.

In a preferred embodiment, the Sjögren's syndrome is primary Sjögren's syndrome.

BRIEF DESCRIPTION OF THE FIGURES

FIGS. 18A, 18B, 18C and 18D are graphs showing in vitro CFZ533 inhibition of the rCD154-induced pathway activation.

FIGS. 26A, 26B, 26C and 26D show experimental results; CD40 signature in ELS in salivary glands and reduction of tertiary lymphoid organs in salivary glands of NOD mice after 10-week treatment with MR1.

DETAILED DESCRIPTION OF THE DISCLOSURE

Figure 1:
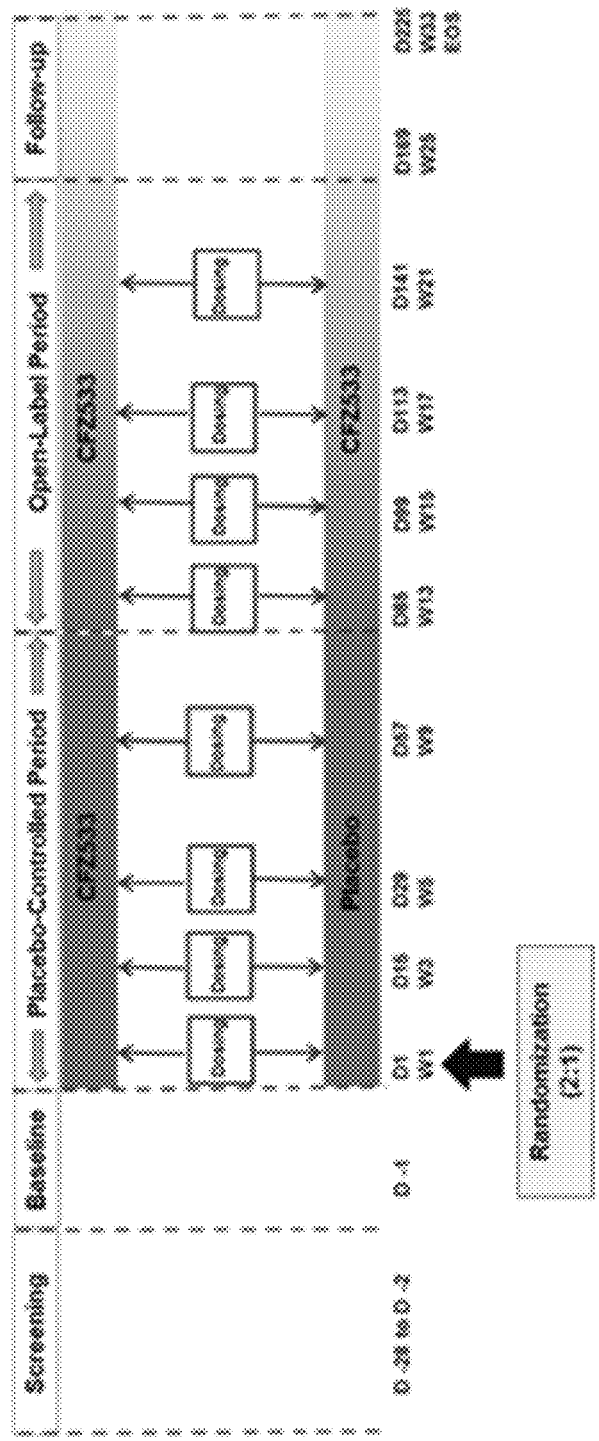
FIG. 1 is a schematic representation of the study design of the first and a second cohort of the proof of concept study for CFZ533 in pSS patients (CCFZ533X2203).

The CD40-CD154 (CD154 is the CD40L) pathway is thought to play an important role in the pathogenesis of Sjögren's syndrome (SS).

Thus, any anti-CD40 monoclonal antibody capable of blocking CD40-CD154 signaling, such as an anti-CD40 antibody with silenced ADCC activity, could be suitable for the treatment of SS, such as primary Sjögren's syndrome (pSS).

Without wishing to be bound by theory, the inventors have identified that sustained plasma concentrations of at least about 40 μg/mL of the CFZ533 antibody during the maintenance regimen was necessary to block the CD40-CD40L pathway in target tissues in SS patients, such as pSS patients. Also, because CFZ533 is subjected to target mediated disposition (which is in relation to target turnover and expression), and SS patients are presenting with high CD40 expression in the body, a loading regimen was necessary at start of treatment to fully saturate CD40 receptors in these patients in conditions where CD40 levels have been enhanced, requiring higher doses or a more frequent regimen at start of treatment. Thus, with a loading dosing regimen providing at start of treatment (2 to 3 weeks) rapid saturation of CD40 receptors, followed by a maintenance dosing regimen providing, throughout the entire treatment period, sustained plasma concentrations at least 40 μg/mL or at least 100 μg/mL, in situations where CD40 expression in affected tissues would be enhanced (severity of the condition), is considered for a therapeutic effect. The observed maximum plasma concentration at steady state was between about 300 and 400 µg/mL (Cohort 3; Study CCFZ533X2203) and was generally safe and well tolerated, with no major signal to suggest increased risk of infection. No thromboembolic event observed.

The appropriate dosage will vary depending upon, for example, the particular CD40 pathway antagonist, e.g. an anti-CD40 antibody or antigen binding fragment thereof (e.g., mAb1, also called CFZ533 herein, mAb2, ASKP1240) or anti-CD40L antibody (e.g. BIIB063) or antigen-binding fragment thereof to be employed, the subject of treatment, the mode of administration and the nature and severity of the condition being treated, and on the nature of prior treatments that the patient has undergone. Ultimately, the attending health care provider will decide the amount of the CD40 pathway antagonist with which to treat each individual patient. In some embodiments, the attending health care provider may administer low doses of the CD40 pathway antagonist and observe the patient's response. In other embodiments, the initial dose(s) of CD40 pathway antagonist administered to a patient are high, and then are titrated downward until signs of relapse occur. Larger doses of the CD40 pathway antagonist may be administered until the optimal therapeutic effect is obtained for the patient, and the dosage is not generally increased further.

In practicing some of the methods of treatment or uses of the present disclosure, a therapeutically effective amount of an CD40 pathway antagonist, e.g. an anti-CD40 antibody or antigen binding fragment thereof (e.g., mAb1, also called CFZ533 herein, mAb2, ASKP1240) or anti-CD40L antibody or antigen-binding fragment thereof is administered to a patient, e.g., a mammal (e.g., a human). While it is understood that the disclosed methods provide for treatment of SS patients using a CD40 pathway antagonist (e.g., mAb1/CFZ533, mAb2, ASKP1240), this does not preclude that, if the patient is to be ultimately treated with a CD40 pathway antagonist, such CD40 pathway antagonist therapy is necessarily a monotherapy. Indeed, if a patient is selected for treatment with a CD40 pathway antagonist, then the CD40 pathway antagonist (e.g., mAb1/CFZ533, mAb2, ASKP1240) may be administered in accordance with the methods of the disclosure either alone or in combination with other agents and therapies.

It will be understood that regimen changes may be appropriate for certain SS patients, such as pSS patients, e.g., patients that display inadequate response to treatment with the CD40 pathway antagonists, e.g. an anti-CD40 antibody or antigen binding fragment thereof (e.g., mAb1, also called CFZ533 herein, mAb2, ASKP1240) or anti-CD40L antibody or antigen-binding fragment thereof to be employed. Thus, administration (e.g mAb1/CFZ533 or mAb2) may be more frequent than monthly dosing, e.g., bi-weekly dosing (every two weeks) or weekly dosing.

Some patients may benefit from a loading regimen (e.g., weekly administrations for several weeks [e.g., 1 to 4 weeks, e.g., dosing at weeks 0, 1, 2, and/or 3, such as 2 weeks, loading dosing regimen at Weeks 0 and 1] followed by a maintenance regimen starting e.g. at Week 3 or 4 where CFZ533 may be administered weekly, bi-weekly or every 4 weeks for several weeks.

For example, an appropriate regimen for mAb1/CFZ533 or mAb2 can be weekly for several weeks [e.g., 1 to 4 weeks, e.g., dosing at weeks 0, 1, 2, and 3] followed by a monthly maintenance regimen.

In another example, an appropriate regimen for mAb1/CFZ533 or mAb2 is weekly for several weeks (e.g., 2 to 8 weeks, such as 3 weeks, e.g., dosing at weeks 0, 1, 2) followed by a bi-weekly maintenance regimen.

It will also be understood that administration (e.g for mAb1/CFZ533 or mAb2) may be less frequent than monthly dosing, e.g., dosing every 6 weeks, every 8 weeks (every two months), quarterly (every three months), etc.

It will be understood that dose escalation may be appropriate for certain SS patients, for example pSS patients, based on severity of the disease, e.g., patients that display inadequate response to treatment with the CD40 pathway antagonists, e.g. an anti-CD40 antibody or antigen binding fragment thereof (e.g., mAb1, also called CFZ533 herein, mAb2, ASKP1240) or anti-CD40L antibody or antigen-binding fragment thereof to be employed. Thus, subcutaneous (s.c.) dosages (loading or maintenance doses) may be greater than about 150 mg to about 900 mg s.c., e.g., about 75 mg, about 100 mg, about 125 mg, about 175 mg, about 200 mg, about 250 mg, about 350 mg, about 400 mg, about 450 mg, about 500 mg, about 600 mg, etc.; similarly, intravenous (i.v.) dosages may be greater than about 10 mg/kg, e.g., about 11 mg/kg, 12 mg/kg, 15 mg/kg, 20 mg/kg, 25 mg/kg, 30 mg/kg, 35 mg/kg, etc. It will also be understood that dose reduction may also be appropriate for certain SS patients, such as pSS patients, e.g., patients that display adverse events or an adverse response to treatment with the CD40 pathway antagonist, e.g. an anti-CD40 antibody or antigen binding fragment thereof (e.g., mAb1, also called CFZ533 herein, mAb2, ASKP1240) or anti-CD40L antibody or antigen-binding fragment thereof). Thus, dosages of the CD40 pathway antagonist (e.g. an anti-CD40 antibody or antigen binding fragment thereof (e.g., mAb1, also called CFZ533 herein, mAb2, ASKP1240) or anti-CD40L antibody or antigen-binding fragment thereof), may be less than about 150 mg to about 900 mg s.c., e.g., about 25 mg, about 50 mg, about 75 mg, about 100 mg, about 125 mg, about 175 mg, about 200 mg, about 250 mg, about 350 mg, about 400 mg, about 450 mg, about 500 mg, about 600 mg, etc.

In some embodiments, the CD40 antagonist, e.g. an anti-CD40 antibody or antigen binding fragment thereof (e.g., mAb1, also called CFZ533 herein, mAb2, ASKP1240) or anti-CD40L antibody or antigen-binding fragment thereof may be administered to the patient at an initial dose of 600 mg delivered s.c., and the dose may be then adjusted to 150 mg or 300 mg delivered s.c. if needed, as determined by a physician.

In some embodiments, the CD40 antagonist, e.g. an anti-CD40 antibody or antigen binding fragment thereof (e.g., mAb1, also called CFZ533 herein, mAb2, ASKP1240) or anti-CD40L antibody or antigen-binding fragment thereof may be administered to the patient at an initial dose of 10 mg/kg delivered i.v., and the dose may be then adjusted to 150 mg or 300 mg delivered s.c. if needed, as determined by a physician.

In a specific embodiment, 3 mg/kg CFZ533 is administered s.c. on day 1 (D1), day 15 (D15), D29, D57, D85, D99, D113, and D141.

In another specific embodiment, 10 mg/kg CFZ533 is administered i.v. on D1, D15, D29, D57, D85, D99, D113, and D141.

In yet another specific embodiment, a loading dose which comprises four unit doses of 600 mg CFZ533 administered s.c. once weekly (Q1W), i.e. 600 mg CFZ533 s.c. on D1, D8, D15 and D22, followed by a maintenance dose which comprises unit doses of 300 mg administered s.c. once weekly (Q1W), i.e. 300 mg CFZ533 s.c. once weekly from D29 to D85.

In a further specific embodiment, a loading dose which comprises one dose of 10 mg CFZ533 per kg of the subject, administered i.v. one time on day 1, followed by a maintenance dose which comprises unit doses of 300 mg administered s.c. once weekly (Q1W), i.e. 300 mg CFZ533 s.c. once weekly from D8 to D85.

CFZ533 may be administered quarterly, monthly, weekly or biweekly e.g. subcutaneously at a dosing of about 75 mg to about 600 mg or about 150 mg to about 300 mg being administered, by subcutaneous injection, at an unit dose of about 75 mg, about 150 mg, about 300 mg, about 450 mg or about 600 mg.

CFZ533 may be administered by subcutaneous injection, weekly, with loading doses of about 150 mg to about 600 mg, wherein the loading doses are administered during 1 to 4 weeks.

The loading dose may also be an i.v. administration of about 10 mg/kg to about 30 mg/kg. Also, the loading doses may be administered subcutaneously weekly or biweekly with doses of about 150 mg, 300 mg and/or 600 mg of the active ingredient.

The loading regimen or dosing of CFZ533 (such as 150/300/600 mg, weekly or bi-weekly) is preferably followed by a maintenance regimen or dosing, administered weekly, biweekly or monthly (every four weeks). The maintenance dose is preferably 300 mg s.c. weekly or bi-weekly, or 600 mg bi-weekly or 600 mg every 4 weeks.

The anti-CD40 antibody or antigen-binding fragment thereof may be CFZ533, a functional derivative thereof or a biosimilar thereof.

As herein defined, "unit dose" refers to a s.c. dose that can be comprised between about 75 mg to 900 mg, e.g. about 150 mg to about 600 mg, e.g. about 150 mg to about 600 mg, e.g. about 300 mg to about 600 mg, or a e.g. about 150 mg to about 300 mg. For example an unit s.c. dose is about 75 mg, about 150 mg, about 300 mg, about 350 mg, about 400 mg, about 450 mg, about 500 mg, about 550 mg, about 600 mg.

Definitions

As used herein, CD40 refers to cluster of differentiation 40, also called tumor necrosis factor receptor superfamily member 5. The term CD40 refers to human CD40, for example as defined in SEQ ID NO: 19, unless otherwise described.

The term "about" in relation to a numerical value x means, for example, +/−10%. When used in front of a numerical range or list of numbers, the term "about" applies to each number in the series, e.g., the phrase "about 1-5" should be interpreted as "about 1-about 5", or, e.g., the phrase "about 1, 2, 3, 4" should be interpreted as "about 1, about 2, about 3, about 4, etc."

The word "substantially" does not exclude "completely," e.g., a composition which is "substantially free" from Y may be completely free from Y. Where necessary, the word "substantially" may be omitted from the definition of the disclosure.

The term "comprising" encompasses "including" as well as "consisting," e.g., a composition "comprising" X may consist exclusively of X or may include something additional, e.g., X+Y.

AUC0-t designates the area under the plasma concentration-time curve from time zero to time 't' where t is a defined time point after administration [mass×time/volume].

AUCtx-ty represents the area under the plasma concentration-time curve from time 'x' to time 'y' where 'time x' and 'time y' are defined time points after administration.

$C_{max}$ is the observed maximum plasma concentration following drug administration [mass/volume].

$C_{min}$ is the observed minimum plasma concentration following drug administration $C_{trough}$ is the observed plasma concentration that is just prior to the beginning of, or at the end of a dosing interval.

$T_{max}$ is the time to reach the maximum concentration after drug administration [time].

ss (subscript) indicate that the parameter is defined at steady state.

The term "antibody" or "anti-CD40 antibody" and the like as used herein refers to whole antibodies that interact with (e.g., by binding, steric hindrance, stabilizing/destabilizing, spatial distribution) a CD40. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FRs). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. The term "antibody" includes for example, monoclonal antibodies, human antibodies, humanized antibodies, camelid antibodies, or chimeric antibodies. The antibodies can be of any isotype (e.g., IgG, IgE, IgM, IgD, IgA and IgY), class (e.g., IgG1, IgG2, IgG3, IgG4, IgA1 and IgA2) or subclass, preferably IgG and most preferably IgG1. Exemplary antibodies include CFZ533 (herein also designated mAb1) and mAb2, as set forth in Table 1.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminus is a variable region and at the C-terminus is a constant region; the CH3 and CL domains actually comprise the carboxy-terminus of the heavy and light chain, respectively. In particular, the term "antibody" specifically includes an IgG-scFv format.

The term "antigen binding portion" of an antibody (or simply "antigen portion"), as used herein, refers to full length or one or more fragments of an antibody, such as a protein, that retain the ability to specifically bind to an antigen or epitope (e.g., a portion of CD40).

The "Complementarity Determining Regions" ("CDRs") are amino acid sequences with boundaries determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273, 927-948 ("Chothia" numbering scheme) and ImMunoGenTics (IMGT) numbering (Lefranc, M.-P., The Immunologist, 7, 132-136 (1999); Lefranc, M.-P. et al., Dev. Comp. Immunol., 27, 55-77 (2003) ("IMGT" numbering scheme). Under IMGT, the CDR regions of an antibody can be determined using the program IMGT/DomainGap Align.

The term "epitope" as used herein refers to any determinant capable of binding with high affinity to an immunoglobulin. An epitope is a region of an antigen that is bound by an antibody that specifically targets that antigen, and when the antigen is a protein, includes specific amino acids that directly contact the antibody. Most often, epitopes reside on proteins, but in some instances, may reside on other kinds of molecules, such as nucleic acids. Epitope determinants may include chemically active surface groupings of molecules such as amino acids, sugar side chains, phosphoryl or sulfonyl groups, and may have specific three dimensional structural characteristics, and/or specific charge characteristics. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., (1988) Science 242:423-426; and Huston et al., (1988) Proc. Natl. Acad. Sci. 85:5879-5883).

The phrase "isolated antibody", as used herein, refers to antibody that is substantially free of other antibodies having different antigenic specificities (e.g., an isolated antibody that specifically binds CD40 is substantially free of antibodies that specifically bind antigens other than CD40). An isolated antibody that specifically binds CD40 may, however, have cross-reactivity to other antigens, such as CD40 molecules from other species. Moreover, an isolated antibody may be substantially free of other cellular material and/or chemicals. The term "monoclonal antibody" or "monoclonal antibody composition" as used herein refer to a preparation of antibody molecules of single molecular composition. The term "human antibody", as used herein, is intended to include antibodies having variable regions in which both the framework and CDR regions are derived from sequences of human origin. A "human antibody" need not be produced by a human, human tissue or human cell. The human antibodies of the disclosure may include amino acid residues not encoded by human sequences (e.g., mutations introduced by random or site-specific mutagenesis in vitro, by N-nucleotide addition at junctions in vivo during recombination of antibody genes, or by somatic mutation in vivo).

"Identity" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent identity, and not considering any conservative substitutions as part of the sequence identity. Neither N- or C-terminal extensions nor insertions shall be construed as reducing identity. Methods and computer programs for the alignment are well known. The percent identity can be determined by standard alignment algorithms, for example, the Basic Local Alignment Search Tool (BLAST) described by Altshul et al. ((1990) J. Mol. Biol., 215: 403 410); the algorithm of Needleman et al. ((1970) J. Mol. Biol., 48: 444 453); or the algorithm of Meyers et al. ((1988) Comput. Appl. Biosci., 4: 11 17). A set of parameters may be the Blosum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

"Amino acid(s)" refer to all naturally occurring L-α-amino acids, e.g., and include D-amino acids. The phrase "amino acid sequence variant" refers to molecules with some differences in their amino acid sequences as compared to the sequences according to the present disclosure. Amino acid sequence variants of an antibody according to the present disclosure, e.g., of a specified sequence, still have the ability to bind the human CD40. Amino acid sequence variants include substitutional variants (those that have at least one amino acid residue removed and a different amino acid inserted in its place at the same position in a polypeptide according to the present disclosure), insertional variants (those with one or more amino acids inserted immediately adjacent to an amino acid at a particular position in a polypeptide according to the present disclosure) and deletional variants (those with one or more amino acids removed in a polypeptide according to the present disclosure).

The term "Fc region" as used herein refers to a polypeptide comprising the CH3, CH2 and at least a portion of the hinge region of a constant domain of an antibody. Optionally, an Fc region may include a CH4 domain, present in some antibody classes. An Fc region, may comprise the entire hinge region of a constant domain of an antibody. In one embodiment, the invention comprises an Fc region and a CH1 region of an antibody. In one embodiment, the invention comprises an Fc region CH3 region of an antibody. In another embodiment, the invention comprises an Fc region, a CH1 region and a $C_{kappa/lambda}$ region from the constant domain of an antibody. In one embodiment, a binding molecule of the invention comprises a constant region, e.g., a heavy chain constant region. In one embodiment, such a constant region is modified compared to a wild-type constant region. That is, the polypeptides of the invention disclosed herein may comprise alterations or modifications to one or more of the three heavy chain constant domains (CH1, CH2 or CH3) and/or to the light chain constant region domain (CL). Example modifications include additions, deletions or substitutions of one or more amino acids in one or more domains. Such changes may be included to optimize effector function, half-life, etc.

As used herein, the term "Affinity" refers to the strength of interaction between antibody and antigen at single antigenic sites. Within each antigenic site, the variable region of the antibody "arm" interacts through weak non-covalent forces with the antigen at numerous sites; the more interactions, the stronger the affinity. As used herein, the term "high affinity" for an IgG antibody or fragment thereof (e.g., a Fab fragment) refers to an antibody having a $K_D$ of $10^{-8}$ M or less, $10^{-9}$ M or less, or $10^{-10}$ M, or $10^{-11}$ M or less, or $10^{-12}$ M or less, or $10^{-13}$ M or less for a target antigen. However, high affinity binding can 10 vary for other antibody isotypes. For example, high affinity binding for an IgM isotype refers to an antibody having a $K_D$ of $10^{-7}$ M or less, or $10^{-8}$ M or less.

As used herein, an antibody or a protein that "specifically binds to CD40 polypeptide" is intended to refer to an antibody or protein that binds to human CD40 polypeptide with a $K_D$ of 100 nM or less, 10 nM or less, 1 nM or less.

An antibody that "cross-reacts with an antigen other than CD40" is intended to refer to an antibody that binds that antigen with a $K_D$ of 1 µM or less, 100 nM or less, 10 nM or less, 1 nM or less. An antibody that "does not cross-react with a particular antigen" is intended to refer to an antibody that binds to that antigen, with a $K_D$ of 100 nM or greater, or a $K_D$ of 1 µM or greater, or a $K_D$ of 10 µM or greater. In certain embodiments, such antibodies that do not cross-react with the antigen exhibit essentially undetectable binding against these proteins in standard binding assays.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction.

The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, or using a biosensor system such as a Biacore® system.

As used herein, the term "ADCC" or "antibody-dependent cellular cytotoxicity" activity refers to cell depleting activity. ADCC activity can be measured by the ADCC assay as well known to a person skilled in the art.

As used herein, the term "silent" antibody refers to an antibody that exhibits no or low ADCC activity as measured in an ADCC assay.

In one embodiment, the term "no or low ADCC activity" means that the silent antibody exhibits an ADCC activity that is below 50% specific cell lysis, for example below 10% specific cell lysis as measured in a standard ADCC assay. No ADCC activity means that the silent antibody exhibits an ADCC activity (specific cell lysis) that is below 1%.

Silenced effector functions can be obtained by mutation in the Fc region of the antibodies and have been described in the art: LALA and N297A (Strohl, W., 2009, Curr. Opin. Biotechnol. vol. 20(6):685-691); and D265A (Baudino et al., 2008, J. Immunol. 181:6664-69; Strohl, W., supra). Examples of silent Fc IgG1 antibodies comprise the so-called LALA mutant comprising L234A and L235A mutation in the IgG1 Fc amino acid sequence. Another example of a silent IgG1 antibody comprises the D265A mutation. Another silent IgG1 antibody comprises the N297A mutation, which results in aglycosylated/non-glycosylated antibodies.

The term "treatment" or "treat" is herein defined as the application or administration of an anti-CD40 antibody or protein according to the invention, for example, mAb1 or mAb2 antibody, to a subject, or application or administration a pharmaceutical composition comprising said anti-CD40 antibody or protein of the invention to an isolated tissue or cell line from a subject, where the subject has an autoimmune disease and/or inflammatory disease, a symptom associated with an autoimmune disease and/or inflammatory disease, or a predisposition toward development of an autoimmune disease and/or inflammatory disease, where the purpose is to alleviate, ameliorate, or improve the autoimmune disease and/or inflammatory disease, any associated symptoms of the autoimmune disease and/or inflammatory disease, or the predisposition toward the development of the autoimmune disease and/or inflammatory disease.

By "treatment" is also intended the application or administration of a pharmaceutical composition comprising an anti-CD40 antibodies or protein of the invention, for example, mAb1 or mAb2 antibody, to a subject, or application or administration of a pharmaceutical composition comprising said anti-CD40 antibody or protein of the invention to an isolated tissue or cell line from a subject, where the subject has an autoimmune disease and/or inflammatory disease, a symptom associated with an autoimmune disease and/or inflammatory disease, or a predisposition toward development of an autoimmune disease and/or inflammatory disease, where the purpose is to alleviate, ameliorate, or improve the autoimmune disease and/or inflammatory disease, any associated symptoms of the autoimmune disease and/or inflammatory disease, or the predisposition toward the development of the autoimmune disease and/or inflammatory disease.

The term "prevent" or "preventing" refer to prophylactic or preventative treatment; it is concerned about delaying the onset of, or preventing the onset of the disease, disorders and/or symptoms associated thereto.

As used herein, a subject is "in need of" a treatment if such subject would benefit biologically, medically or in quality of life from such treatment. The term "pharmaceutically acceptable" means a nontoxic material that does not interfere with the effectiveness of the biological activity of the active ingredient(s).

As used herein, the term "administration" or "administering" of the subject compound means providing a compound of the invention and prodrugs thereof to a subject in need of treatment. Administration "in combination with" one or more further therapeutic agents includes simultaneous (concurrent) and consecutive administration in any order, and in any route of administration. One administration may be a single injection, or multiple injections delivered in conjunction with each other, depending on how much drug substance needs to be administered to achieve therapeutic effect.

As used herein, a "therapeutically effective amount" refers to an amount of an anti-CD40 antibody or antigen binding fragment thereof, e.g., mAb1, that is effective, upon single or multiple dose administration to a patient (such as a human) for treating, preventing, preventing the onset of, curing, delaying, reducing the severity of, ameliorating at least one symptom of a disorder or recurring disorder, or prolonging the survival of the patient beyond that expected in the absence of such treatment. When applied to an individual active ingredient (e.g., an anti-CD40 antibody, e.g., mAb1) administered alone, the term refers to that ingredient alone. When applied to a combination, the term refers to combined amounts of the active ingredients that result in the therapeutic effect, whether administered in combination, serially or simultaneously.

The phrase "therapeutic regimen" means the regimen used to treat an illness, e.g., the dosing protocol used during the treatment of SS, such as pSS. A therapeutic regimen may include an loading regimen (or loading dosing), followed by a maintenance regimen (or maintenance dosing).

The phrase "loading regimen" or "loading period" refers to a treatment regimen (or the portion of a treatment regimen) that is used for the initial treatment of a disease. In some embodiments, the disclosed methods, uses, kits, processes and regimens (e.g., methods of treating SS) employ an loading regimen (or loading dosing). In some cases, the loading period is the period until maximum efficacy is reached. The general goal of an loading regimen is to provide a high level of drug to a patient during the initial period of a treatment regimen. A loading regimen may include administering a greater dose of the drug than a physician would employ during maintenance regimen, administering a drug more frequently than a physician would administer the drug during a maintenance regimen, or both. Dose escalation may occur during or after the loading regimen.

The phrase "maintenance regimen" or "maintenance period" refers to a treatment regimen (or the portion of a treatment regimen) that is used for the maintenance of a patient during treatment of an illness, e.g., to keep the patient in remission for long periods of time (months or years) following the loading regimen or period. In some embodiments, the disclosed methods, uses and regimens employ a maintenance regimen. A maintenance regimen may employ continuous therapy (e.g., administering a drug at a regular intervals, e.g., weekly, bi-weekly or monthly (every 4 weeks), yearly, etc.) or intermittent therapy (e.g., interrupted treatment, intermittent treatment, treatment at relapse, or treatment upon achievement of a particular predetermined criteria [e.g., pain, disease manifestation, etc.]). Dose escalation may occur during a maintenance regimen.

The phrase "means for administering" is used to indicate any available implement for systemically administering a drug to a patient, including, but not limited to, a pre-filled syringe, a vial and syringe, an injection pen, an autoinjector, an i.v. drip and bag, a pump, a patch pump, etc. With such items, a patient may self-administer the drug (i.e., administer the drug on their own behalf) or a physician may administer the drug.

Example 1. Anti-CD40 Antibodies

Anti-CD40 mAbs with silenced ADCC activity have been disclosed in U.S. Pat. Nos. 8,828,396 and 9,221,913, incorporated by reference here in their entirety. Anti-CD40 mAbs with silenced ADCC activity are predicted to have an improved safety profile relative to other anti-CD40 antibodies, and in particular may be more suitable for non-oncologic indications, such as Sjögren's syndrome (SS) and particularly primary Sjögren's syndrome (pSS).

According to a non-binding hypothesis of the inventors, the two mAbs from U.S. Pat. Nos. 8,828,396 and 9,221,913, designated mAb1 and mAb2, are thought to be suitable compounds for treatment of SS. The antibody mAb1, also called CFZ533, is particularly preferred.

mAb1 inhibits CD154-induced activation in vitro and T cell-dependent antibody formation and germinal center formation in vivo. In patients with pSS, CD40 blockade with mAb1 has been shown to offer a new treatment modality (Example 7).

To enable a person skilled in the art to practice the invention, the amino acid and nucleotide sequences of mAb1 and mAb2 are provided in Table 1 below.

Another anti-CD40 mAb known in the art is ASKP1240 from Astellas Pharma/Kyowa Hakko Kirin Co, as described e.g. in U.S. Pat. No. 8,568,725B2, incorporated by reference herein.

Yet another anti-CD40 mAb known in the art is BI655064 from Boehringer Ingelheim, as described e.g. in U.S. Pat. No. 8,591,900, incorporated by reference herein.

A further anti-CD40 mAb known in the art is FFP104 by Fast Forward Pharmaceuticals, as described e.g. in U.S. Pat. No. 8,669,352, incorporated by reference herein.

Another treatment modality might be MEDI4920 from AstraZeneca, which is a Anti-CD40L-Tn3 fusion protein, or the anti-CD40L antibody BIIB063 from Biogen.

Antibodies with the same mode of action as the above mentioned antibodies, so called biosimilars, are also covered by the disclosure, as will be appreciated by a person skilled in the art.

TABLE 1

Sequence table

| SEQ ID NO: | Description of sequence | Detailed amino acid or nucleotide sequences |
|---|---|---|
| 1 | HCDR1 of mAb 1 and mAb2 (Kabat) | SYGMH |
| 2 | HCDR2 of mAb 1 and mAb2 (Kabat) | VISYEESNRYHADSVKG |
| 3 | HCDR3 of mAb 1 and mAb2 (Kabat) | DGGIAAPGPDY |
| 4 | LCDR1 of mAb 1 and mAb2 (Kabat) | RSSQSLLYSNGYNYLD |
| 5 | LCDR2 of mAb 1 and mAb2 (Kabat) | LGSNRAS |
| 6 | LCDR3 of mAb 1 and mAb2 (Kabat) | MQARQTPFT |
| 7 | Variable Heavy chain of mAb1 and mAb2 | QVQLVESGGGVVQPGRSLRLSCAASGFTFSSYGM HWVRQAPGKGLEWVAVISYEESNRYHADSVKGR FTISRDNSKITLYLQMNSLRTEDTAVYYCARDGGI AAPGPDYWGQGTLVTVSS |
| 8 | Variable light chain of mAb1 and mAb2 | DIVMTQSPLSLTVTPGEPASISCRSSQSLLYSNGYN YLDWYLQKPGQSPQVLISLGSNRASGVPDRFSGS GSGTDFTLKISRVEAEDVGVYYCMQARQTPFTFG PGTKVDIR |

TABLE 1-continued

Sequence table

| SEQ ID NO: | Description of sequence | Detailed amino acid or nucleotide sequences |
|---|---|---|
| 9 | Full length heavy chain of mAb1 | QVQLVESGGGVVQPGRSLRLSCAASGFTFSSYGM HWVRQAPGKGLEWVAVISYEESNRYHADSVKGR FTISRDNSKITLYLQMNSLRTEDTAVYYCARDGGI AAPGPDYWGQGTLVTVSSASTKGPSVFPLAPSSKS TSGGTAALGCLVKDYFPEPVTVSWNSGALTSGVH TFPAVLQSSGLYSLSSVVTVPSSSLGTQTYICNVNH KPSNTKVDKRVEPKSCDKTHTCPPCPAPELLGGPS VFLFPPKPKDTLMISRTPEVTCVVVDVSHEDPEVK FNWYVDGVEVHNAKTKPREEQYASTYRVVSVLT VLHQDWLNGKEYKCKVSNKALPAPIEKTISKAKG QPREPQVYTLPPSREEMTKNQVSLTCLVKGFYPSD IAVEWESNGQPENNYKTTPPVLDSDGSFFLYSKLT VDKSRWQQGNVFSCSVMHEALHNHYTQKSLSLS PGK |
| 10 | Full length light chain of mAb1 | DIVMTQSPLSLTVTPGEPASISCRSSQSLLYSNGYN YLDWYLQKPGQSPQVLISLGSNRASGVPDRFSGS GSGTDFTLKISRVEAEDVGVYYCMQARQTPFTFG PGTKVDIRRTVAAPSVFIFPPSDEQLKSGTASVVCL LNNFYPREAKVQWKVDNALQSGNSQESVTEQDS KDSTYSLSSTLTLSKADYEKHKVYACEVTHQGLS SPVTKSFNRGEC |
| 11 | Full length heavy chain of mAb2 | QVQLVESGGGVVQPGRSLRLSCAASGFTFSSYGM HWVRQAPGKGLEWVAVISYEESNRYHADSVKGR FTISRDNSKITLYLQMNSLRTEDTAVYYCARDGGI AAPGPDYWGQGTLVTVSSASTKGPSVFPLAPSSKS TSGGTAALGCLVKDYFPEPVTVSWNSGALTSGVH TFPAVLQSSGLYSLSSVVTVPSSSLGTQTYICNVNH KPSNTKVDKRVEPKSCDKTHTCPPCPAPELLGGPS VFLFPPKPKDTLMISRTPEVTCVVVAVSHEDPEVK FNWYVDGVEVHNAKTKPREEQYNSTYRVVSVLT VLHQDWLNGKEYKCKVSNKALPAPIEKTISKAKG QPREPQVYTLPPSREEMTKNQVSLTCLVKGFYPSD IAVEWESNGQPENNYKTTPPVLDSDGSFFLYSKLT VDKSRWQQGNVFSCSVMHEALHNHYTQKSLSLS PGK |
| 12 | Full length light chain of mAb2 | DIVMTQSPLSLTVTPGEPASISCRSSQSLLYSNGYN YLDWYLQKPGQSPQVLISLGSNRASGVPDRFSGS GSGTDFTLKISRVEAEDVGVYYCMQARQTPFTFG PGTKVDIRRTVAAPSVFIFPPSDEQLKSGTASVVCL LNNFYPREAKVQWKVDNALQSGNSQESVTEQDS KDSTYSLSSTLTLSKADYEKHKVYACEVTHQGLS SPVTKSFNRGEC |
| 13 | Fc region of mAb1 | APELLGGPSVFLFPPKPKDTLMISRTPEVTCVVVD VSHEDPEVKFNWYVDGVEVHNAKTKPREEQYAS TYRVVSVLTVLHQDWLNGKEYKCKVSNKALPAPI EKTISKAKGQPREPQVYTLPPSREEMTKNQVSLTC LVKGFYPSDIAVEWESNGQPENNYKTTPPVLDSD GSFFLYSKLTVDKSRWQQGNVFSCSVMHEALHN HYTQKSLSLSPGK |
| 14 | Fc region of mAb2 | APELLGGPSVFLFPPKPKDTLMISRTPEVTCVVVA VSHEDPEVKFNWYVDGVEVHNAKTKPREEQYNS TYRVVSVLTVLHQDWLNGKEYKCKVSNKALPAPI EKTISKAKGQPREPQVYTLPPSREEMTKNQVSLTC LVKGFYPSDIAVEWESNGQPENNYKTTPPVLDSD GSFFLYSKLTVDKSRWQQGNVFSCSVMHEALHN HYTQKSLSLSPGK |
| 15 | DNA encoding Full length heavy chain of mAb1 | CAGGTGCAGCTGGTGGAATCTGGCGGCGGAGTG GTGCAGCCTGGCCGGTCCCTGAGACTGTCTTGC GCCGCCTCCGGCTTCACCTTCTCCAGCTACGGC ATGCACTGGGTGCGACAGGCCCCTGGCAAGGG ACTGGAATGGGTGGCCGTGATCTCCTACGAGGA ATCCAACAGATACCACGCTGACTCCGTGAAGGG CCGGTTCACAATCTCCCGGGACAACTCCAAGAT CACCCTGTACCTGCAGATGAACTCCCTGCGGAC CGAGGACACCGCCGTGTACTACTGCGCCAGGGA CGGAGGAATCGCCGCTCCTGGACCTGATTATTG GGGCCAGGGCACCCTGGTGACAGTGTCCTCCGC TAGCACCAAGGGCCCCTCCGTGTTCCCTCTGGC |

TABLE 1-continued

Sequence table

| SEQ ID NO: | Description of sequence | Detailed amino acid or nucleotide sequences |
|---|---|---|
| | | CCCCTCCAGCAAGTCCACCTCTGGCGGCACCGC
CGCTCTGGGCTGCCTGGTGAAAGACTACTTCCC
CGAGCCCGTGACCGTGTCCTGGAACTCTGGCGC
CCTGACCTCCGGCGTGCACACCTTTCCAGCCGT
GCTGCAGTCCTCCGGCCTGTACTCCCTGTCCTCC
GTGGTGACCGTGCCCTCTAGCTCTCTGGGCACC
CAGACCTACATCTGCAACGTGAACCACAAGCCC
TCCAACACCAAGGTGGACAAGCGGGTGGAACC
CAAGTCCTGCGACAAGACCCACACCTGTCCCCC
CTGCCCTGCCCCTGAACTGCTGGGCGGACCTTC
CGTGTTCCTGTTCCCCCCAAAGCCCAAGGACAC
CCTGATGATCTCCCGGACCCCCGAAGTGACCTG
CGTGGTGGTGGACGTGTCCCACGAGGACCCTGA
AGTGAAGTTCAATTGGTACGTGGACGGCGTGGA
AGTGCACAACGCCAAGACCAAGCCCAGAGAGG
AACAGTACGCCTCCACCTACCGGGTGGTGTCTG
TGCTGACCGTGCTGCACCAGGACTGGCTGAACG
GCAAAGAGTACAAGTGCAAGGTCTCCAACAAG
GCCCTGCCTGCCCCCATCGAAAAGACCATCTCC
AAGGCCAAGGGCCAGCCCCGCGAGCCACAGGT
GTACACACTGCCCCCCAGCCGGGAAGAGATGAC
CAAGAACCAGGTGTCCCTGACCTGTCTGGTCAA
AGGCTTCTACCCCTCCGATATCGCCGTGGAGTG
GGAGTCCAACGGACAGCCCGAGAACAACTACA
AGACCACCCCCCCTGTGCTGGACTCCGACGGCT
CATTCTTCCTGTACTCCAAGCTGACCGTGGACA
AGTCCCGGTGGCAGCAGGGCAACGTGTTCTCCT
GCTCCGTGATGCACGAGGCCCTGCACAACCACT
ACACCCAGAAGTCCCTGTCCCTGAGCCCCGGCA
AG |
| 16 | DNA encoding Full length light chain of mAb1 | GACATCGTGATGACCCAGTCCCCCCCTGTCCCTG
ACCGTGACACCTGGCGAGCCTGCCTCTATCTCC
TGCAGATCCTCCCAGTCCCTGCTGTACTCCAAC
GGCTACAACTACCTGGACTGGTATCTGCAGAAG
CCCGGCCAGTCCCCACAGGTGCTGATCTCCCTG
GGCTCCAACAGAGCCTCTGGCGTGCCCGACCGG
TTCTCCGGCTCTGGCTCTGGCACCGACTTCACAC
TGAAGATCTCACGGGTGGAAGCCGAGGACGTG
GGCGTGTACTACTGCATGCAGGCCCGGCAGACC
CCCTTCACCTTCGGCCCTGGCACCAAGGTGGAC
ATCCGGCGTACGGTGGCCGCTCCCAGCGTGTTC
ATCTTCCCCCCCAGCGACGAGCAGCTGAAGAGC
GGCACCGCCAGCGTGGTGTGCCTGCTGAACAAC
TTCTACCCCCGGGAGGCCAAGGTGCAGTGGAAG
GTGGACAACGCCCTGCAGAGCGGCAACAGCCA
GGAGAGCGTCACCGAGCAGGACAGCAAGGACT
CCACCTACAGCCTGAGCAGCACCCTGACCCTGA
GCAAGGCCGACTACGAGAAGCATAAGGTGTAC
GCCTGCGAGGTGACCCACCAGGGCCTGTCCAGC
CCCGTGACCAAGAGCTTCAACAGGGGCGAGTGC |
| 17 | DNA encoding Full length heavy chain of mAb2 | CAGGTGCAGCTGGTGGAATCTGGCGGCGGAGTG
GTGCAGCCTGGCCGGTCCCTGAGACTGTCTTGC
GCCGCCTCCGGCTTCACCTTCTCCAGCTACGGC
ATGCACTGGGTGCGACAGGCCCCTGGCAAGGG
ACTGGAATGGGTGGCCGTGATCTCCTACGAGGA
ATCCAACAGATACCACGCTGACTCCGTGAAGGG
CCGGTTCACAATCTCCCGGGACAACTCCAAGAT
CACCCTGTACCTGCAGATGAACTCCCTGCGGAC
CGAGGACACCGCCGTGTACTACTGCGCCAGGGA
CGGAGGAATCGCCGCTCCTGGACCTGATTATTG
GGGCCAGGGCACCCTGGTGACAGTGTCCTCCGC
TAGCACCAAGGGCCCCTCCGTGTTCCCTCTGGC
CCCCTCCAGCAAGTCCACCTCTGGCGGCACCGC
CGCTCTGGGCTGCCTGGTGAAAGACTACTTCCC
CGAGCCCGTGACCGTGTCCTGGAACTCTGGCGC
CCTGACCTCCGGCGTGCACACCTTTCCAGCCGT
GCTGCAGTCCTCCGGCCTGTACTCCCTGTCCTCC
GTGGTGACCGTGCCCTCTAGCTCTCTGGGCACC
CAGACCTACATCTGCAACGTGAACCACAAGCCC
TCCAACACCAAGGTGGACAAGCGGGTGGAACC
CAAGTCCTGCGACAAGACCCACACCTGTCCCCC
CTGCCCTGCCCCTGAACTGCTGGGCGGACCTTC |

TABLE 1-continued

Sequence table

| SEQ ID NO: | Description of sequence | Detailed amino acid or nucleotide sequences |
|---|---|---|
| | | CGTGTTCCTGTTCCCCCCAAAGCCCAAGGACAC<br>CCTGATGATCTCCCGGACCCCCGAAGTGACCTG<br>CGTGGTGGTGGCCGTGTCCCACGAGGACCCTGA<br>AGTGAAGTTCAATTGGTACGTGGACGGCGTGGA<br>AGTGCACAACGCCAAGACCAAGCCCAGAGAGG<br>AACAGTACAACTCCACCTACCGGGTGGTGTCTG<br>TGCTGACCGTGCTGCACCAGGACTGGCTGAACG<br>GCAAAGAGTACAAGTGCAAGGTCTCCAACAAG<br>GCCCTGCCTGCCCCCATCGAAAAGACCATCTCC<br>AAGGCCAAGGGCCAGCCCCGCGAGCCACAGGT<br>GTACACACTGCCCCCCAGCCGGGAAGAGATGAC<br>CAAGAACCAGGTGTCCCTGACCTGTCTGGTCAA<br>AGGCTTCTACCCCTCCGATATCGCCGTGGAGTG<br>GGAGTCCAACGGACAGCCCGAGAACAACTACA<br>AGACCACCCCCCCTGTGCTGGACTCCGACGGCT<br>CATTCTTCCTGTACTCCAAGCTGACCGTGGACA<br>AGTCCCGGTGGCAGCAGGGCAACGTGTTCTCCT<br>GCTCCGTGATGCACGAGGCCCTGCACAACCACT<br>ACACCCAGAAGTCCCTGTCCCTGAGCCCCGGCA<br>AG |
| 18 | DNA encoding Full length light chain of mAb2 | GACATCGTGATGACCCAGTCCCCCCTGTCCCTG<br>ACCGTGACACCTGGCGAGCCTGCCTCTATCTCC<br>TGCAGATCCTCCCAGTCCCTGCTGTACTCCAAC<br>GGCTACAACTACCTGGACTGGTATCTGCAGAAG<br>CCCGGCCAGTCCCCACAGGTGCTGATCTCCCTG<br>GGCTCCAACAGAGCCTCTGGCGTGCCCGACCGG<br>TTCTCCGGCTCTGGCTCTGGCACCGACTTCACAC<br>TGAAGATCTCACGGGTGGAAGCCGAGGACGTG<br>GGCGTGTACTACTGCATGCAGGCCCGGCAGACC<br>CCCTTCACCTTCGGCCCTGGCACCAAGGTGGAC<br>ATCCGGCGTACGGTGGCCGCTCCCAGCGTGTTC<br>ATCTTCCCCCCCAGCGACGAGCAGCTGAAGAGC<br>GGCACCGCCAGCGTGGTGTGCCTGCTGAACAAC<br>TTCTACCCCGGGAGGCCAAGGTGCAGTGGAAG<br>GTGGACAACGCCCTGCAGAGCGGCAACAGCCA<br>GGAGAGCGTCACCGAGCAGGACAGCAAGGACT<br>CCACCTACAGCCTGAGCAGCACCCTGACCCTGA<br>VGCAAGGCCGACTACGAGAAGCATAAGGTGTAC<br>GCCTGCGAGGTGACCCACCAGGGCCTGTCCAGC<br>CCCGTGACCAAGAGCTTCAACAGGGGCGAGTGC |
| 19 | Amino acid sequence of human CD40 | MVRLPLQCVLWGCLLTAVHPEPPTACREKQYLIN<br>SQCCSLCQPGQKLVSDCTEFTETECLPCGESEFLD<br>TWNRETHCHQHKYCDPNLGLRVQQKGTSETDTIC<br>TCEEGWHCTSEACESCVLHRSCSPGFGVKQIATG<br>VSDTICEPCPVGFFSNVSSAFEKCHPWTSCETKDL<br>VVQQAGTNKTDVVCGPQDRLRALVVIPIIFGILFAI<br>LLVLVFIKKVAKKPTNKAPHPKQEPQEINFPDDLP<br>GSNTAAPVQETLHGCQPVTQEDGKESRISVQERQ |

In one embodiment, an anti-CD40 antibody is provided, said antibody comprising an immunoglobulin VH domain comprising the hypervariable regions set forth as SEQ ID NO: 1, SEQ ID NO: 2, and SEQ ID NO: 3 and an immunoglobulin VL domain comprising the hypervariable regions set forth as SEQ ID NO: 4, SEQ ID NO: 5 and SEQ ID NO: 6.

In one embodiment, an anti-CD40 antibody is provided, said antibody comprising an immunoglobulin VH domain comprising the amino acid sequence of SEQ ID NO: 7 and an immunoglobulin VL domain comprising the amino acid sequence of SEQ ID NO: 8, and an Fc region of SEQ ID NO: 13.

In one embodiment, an anti-CD40 antibody is provided, said antibody comprising an immunoglobulin VH domain comprising the amino acid sequence of SEQ ID NO: 7 and an immunoglobulin VL domain comprising the amino acid sequence of SEQ ID NO: 8, and an Fc region of SEQ ID NO: 14.

In one embodiment, an anti-CD40 antibody is provided, said antibody comprising a silent Fc IgG1 region.

In a preferred embodiment, an anti-CD40 antibody designated mAb1 is provided. Specifically, mAb1 comprises the heavy chain amino acid sequence of SEQ ID NO: 9 and the light chain amino acid sequence of SEQ ID NO: 10; and mAb2 comprises the heavy chain amino acid sequence of SEQ ID NO: 11 and the light chain amino acid sequence of SEQ ID NO: 12.

1. Expression Systems

For expression of the light and heavy chains, the expression vector(s) encoding the heavy and light chains are transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is theoretically possible to express the antibodies of the invention in either prokaryotic or eukaryotic host cells. Expression of antibodies in eukaryotic cells, for example mammalian host cells, yeast or filamentous fungi, is discussed because such eukaryotic cells, and in particular mammalian cells, are more likely than prokaryotic cells to assemble and secrete a properly folded and immunologically active antibody.

Particularly a cloning or expression vector can comprise either at least one of the following coding sequences (a)-(b), operatively linked to suitable promoter sequences:
  (a) SEQ ID NO: 15 and SEQ ID NO: 16 encoding respectively the full length heavy and light chains of mAb1; or
  (b) SEQ ID NO: 17 and SEQ ID NO: 18 encoding respectively the full length heavy and light chains of mAb2.

Mammalian host cells for expressing the recombinant antibodies of the invention include Chinese Hamster Ovary (CHO cells) (including dhfr-CHO cells, described Urlaub and Chasin, 1980 Proc. Natl. Acad. Sci. USA 77:4216-4220 used with a DHFR selectable marker, e.g., as described in R. J. Kaufman and P. A. Sharp, 1982 Mol. Biol. 159:601-621), CHOK1 dhfr+ cell lines, NSO myeloma cells, COS cells and SP2 cells. In particular, for use with NSO myeloma cells, another expression system is the GS gene expression system shown in PCT Publications WO 87/04462, WO 89/01036 and EP0338841.

When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods (See for example Abhinav et al. 2007, Journal of Chromatography 848: 28-37).

The host cells may be cultured under suitable conditions for the expression and production of mAb1 or mAb2.

2. Pharmaceutical Compositions

Therapeutic antibodies are typically formulated either in aqueous form ready for administration or as lyophilisate for reconstitution with a suitable diluent prior to administration. An anti-CD40 antibody may be formulated either as a lyophilisate, or as an aqueous composition, for example in pre-filled syringes. The formulation is also called drug product (DP).

Suitable formulation can provide an aqueous pharmaceutical composition or a lyophilisate which can be reconstituted to give a solution with a high concentration of the antibody active ingredient and a low level of antibody aggregation for delivery to a patient. High concentrations of antibody are useful as they reduce the amount of material which must be delivered to a patient. Reduced dosing volumes minimize the time taken to deliver a fixed dose to the patient. The aqueous compositions of the invention with high concentration of anti-CD40 antibodies are particularly suitable for subcutaneous administration.

Thus the invention provides an aqueous pharmaceutical composition, suitable for administration in a subject, e.g., for subcutaneous administration, comprising an anti-CD40 antibody such as mAb1 or mAb2.

The anti-CD40 antibody may be used as a pharmaceutical composition when combined with a pharmaceutically acceptable carrier. Such a composition may contain, in addition to an anti-CD40 antibody such as mAb1 or mAb2, carriers, various diluents, fillers, salts, buffers, stabilizers, solubilizers, and other materials well known in the art. The characteristics of the carrier will depend on the route of administration. The pharmaceutical compositions for use in the disclosed methods may also contain additional therapeutic agents for treatment of the particular targeted disorder.

In one specific embodiment the composition, also called drug product (DP) is a lyophilized formulation prepared from an aqueous formulation having a pH of 6.0 and comprising:
  (i) 150 mg/mL mAb1 or mAb2
  (ii) 270 mM sucrose as a stabilizer,
  (iii) 30 mM L-histidine as a buffering agent, and
  (iv) 0.06% Polysorbate 20 as a surfactant.

In another specific embodiment the pharmaceutical composition, also called drug product (DP), is an aqueous pharmaceutical composition has a pH of 6.0 and comprising:
  (i) 150 mg/mL mAb1 or mAb2
  (ii) 270 mM sucrose as a stabilizer,
  (iii) 30 mM L-histidine as a buffering agent, and
  (iv) 0.06% Polysorbate 20 as a surfactant.

3. Route of Administration

Typically, the antibodies or proteins are administered by injection, for example, either intravenously, intraperitoneally, or subcutaneously. Methods to accomplish this administration are known to those of ordinary skill in the art. It may also be possible to obtain compositions that may be topically or orally administered, or which may be capable of transmission across mucous membranes. As will be appreciated by a person skilled in the art, any suitable means for administering can be used, as appropriate for a particular selected route of administration.

Examples of possible routes of administration include parenteral, (e.g., intravenous (I.V. or IV), intramuscular (IM), intradermal, subcutaneous (S.C. or SC), or infusion), oral and pulmonary (e.g., inhalation), nasal, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

An anti-CD40 therapy can be initiated by administering a loading regimen or loading dosing of the antibody or protein of the invention to the subject in need of anti-CD40 therapy. By "loading dose(s)" is intended an initial dosing of the anti-CD40 antibody or protein of the invention that is administered to the subject one or several times, where the dose of the antibody or protein of the invention administered falls within the higher dosing range (i.e., from about 10 mg/kg to about 50 mg/kg, such as about 30 mg/kg intravenously, or about 600 mg, or about 300 mg or about 150 mg weekly, bi-weekly for up to 4 weeks). The "loading regimen" can be administered as a single administration or multiple administrations, for example, a single or multiple intravenous infusion(s), or as multiple subcutaneous administrations combined in a "loading dosing" regimen depending on the severity of the disease). Following administration of the "loading regimen", the subject is then administered one or more additional therapeutically effective doses of the anti-CD40 antibody or protein of the invention. Subsequent therapeutically effective doses can be administered, for example, according to a weekly dosing schedule, or once every two weeks (bi-weekly), once every three weeks, or once every four weeks. In such embodiments, the subsequent therapeutically effective doses generally fall within the lower dosing range (i.e. about 0.003 mg/kg to about 30 mg/kg, such as about 10 mg/kg, e.g 10 mg/kg IV or about 150 mg, about 300 mg or about 600 mg administered weekly, bi-weekly or every 4 weeks subcutaneously).

Alternatively, in some embodiments, following the "loading regimen", the subsequent therapeutically effective doses of the anti-CD40 antibody or protein of the invention are administered according to a "maintenance schedule", wherein the therapeutically effective dose of the antibody or protein of the invention is administered once a month, once every 6 weeks, once every two months, once every 10 weeks, once every three months, once every 14 weeks, once every four months, once every 18 weeks, once every five months, once every 22 weeks, once every six months, once every 7 months, once every 8 months, once every 9 months, once every 10 months, once every 11 months, or once every 12 months. In such embodiments, the therapeutically effective doses of the anti-CD40 antibody or protein of the invention fall within the lower dosing range (i.e. about 0.003 mg/kg to about 30 mg/kg, such as about 10 mg/kg, e.g. 10 mg/kg), particularly when the subsequent doses are administered at more frequent intervals, for example, weekly, once every two weeks to once every four weeks, or within the higher dosing range (i.e., from 10 mg/kg to 50 mg/kg, such as 30 mg/kg), particularly when the subsequent doses are administered at less frequent intervals, for example, where subsequent doses are administered one month to 12 months apart.

The timing of dosing is generally measured from the day of the first dose of the active compound (e.g., mAb1), which is also known as "baseline". However, different health care providers use different naming conventions.

Notably, week zero may be referred to as week 1 by some health care providers, while day zero may be referred to as day one by some health care providers. Thus, it is possible that different physicians will designate, e.g., a dose as being given during week 3/on day 21, during week 3/on day 22, during week 4/on day 21, during week 4/on day 22, while referring to the same dosing schedule. For consistency, the first week of dosing will be referred to herein as week 0, while the first day of dosing will be referred to as day 1. However, it will be understood by a skilled artisan that this naming convention is simply used for consistency and should not be construed as limiting, i.e., weekly dosing is the provision of a weekly dose of the anti-CD40 antibody, e.g., mAb1, regardless of whether the physician refers to a particular week as "week 1" or "week 2". Example of dosage regimes as noted herein are found in FIGS. 1 and 2. It will be understood that a dose need not be provided at an exact time point, e.g., a dose due approximately on day 29 could be provided, e.g., on day 24 to day 34, e.g., day 30, as long as it is provided in the appropriate week.

As used herein, the phrase "container having a sufficient amount of the anti-CD40 antibody to allow delivery of [a designated dose]" is used to mean that a given container (e.g., vial, pen, syringe) has disposed therein a volume of an anti-CD40 antibody (e.g., as part of a pharmaceutical composition) that can be used to provide a desired dose. As an example, if a desired dose is 500 mg, then a clinician may use 2 ml from a container that contains an anti-CD40 antibody formulation with a concentration of 250 mg/ml, 1 ml from a container that contains an anti-CD40 antibody formulation with a concentration of 500 mg/ml, 0.5 ml from a container contains an anti-CD40 antibody formulation with a concentration of 1000 mg/ml, etc. In each such case, these containers have a sufficient amount of the anti-CD40 antibody to allow delivery of the desired 500 mg dose.

As used herein, the phrase "formulated at a dosage to allow [route of administration] delivery of [a designated dose]" is used to mean that a given pharmaceutical composition can be used to provide a desired dose of an anti-CD40 antibody, e.g., mAb1, via a designated route of administration (e.g., s.c. or i.v.). As an example, if a desired subcutaneous dose is 500 mg, then a clinician may use 2 ml of an anti-CD40 antibody formulation having a concentration of 250 mg/ml, 1 ml of an anti-CD40 antibody formulation having a concentration of 500 mg/ml, 0.5 ml of an anti-CD40 antibody formulation having a concentration of 1000 mg/ml, etc. In each such case, these anti-CD40 antibody formulations are at a concentration high enough to allow subcutaneous delivery of the anti-CD40 antibody. Subcutaneous delivery typically requires delivery of volumes of less than about 2 ml, preferably a volume of about 1 ml or less. However, higher volumes may be delivered over time using, e.g, a patch/pump mechanism.

Disclosed herein is the use of an anti-CD40 antibody (e.g., mAb1) for the manufacture of a medicament for the treatment of Sjögren's syndrome in a patient, wherein the medicament is formulated to comprise containers, each container having a sufficient amount of the anti-CD40 antibody to allow delivery of at least about 75 mg, 150 mg, 300 mg or 600 mg anti-CD40 antibody or antigen binding fragment thereof (e.g., mAb1) per unit dose.

Disclosed herein is the use of an anti-CD40 antibody (e.g., mAb1) for the manufacture of a medicament for the treatment of Sjögren's syndrome in a patient, wherein the medicament is formulated at a dosage to allow systemic delivery (e.g., i.v. or s.c. delivery) 75 mg, 150 mg, 300 mg of 600 mg anti-CD40 antibody or antigen binding fragment thereof (e.g., mAb1) per unit dose.

4. Kits

The disclosure also encompasses kits for treating a patient with Sjögren's syndrome (as the case may be) with an anti-CD40 antibody or antigen binding fragment thereof, e.g., mAb1. Such kits comprise an anti-CD40 antibody or antigen binding fragment thereof, e.g., mAb1 (e.g., in liquid or lyophilized form) or a pharmaceutical composition comprising the anti-CD40 antibody (described supra). Additionally, such kits may comprise means for administering the anti-CD40 antibody (e.g., a syringe and vial, a prefilled syringe, a prefilled pen, a patch/pump) and instructions for use. The instructions may disclose providing the anti-CD40 antibody (e.g., mAb1) to the patient as part of a specific dosing regimen. These kits may also contain additional therapeutic agents (described supra) for treating psoriasis, e.g., for delivery in combination with the enclosed anti-CD40 antibody, e.g., mAb1.

The phrase "means for administering" is used to indicate any available implement for systemically administering a drug top a patient, including, but not limited to, a pre-filled syringe, a vial and syringe, an injection pen, an autoinjector, an i.v. drip and bag, a pump, patch/pump, etc. With such items, a patient may self-administer the drug (i.e., administer the drug on their own behalf) or a care-giver or a physician may administer the drug.

Disclosed herein are kits for the treatment of a patient having Sjögren's syndrome, comprising: a) a pharmaceutical composition comprising a therapeutically effective amount of an anti-CD40 antibody or antigen binding fragment thereof; b) means for administering the anti-CD40 antibody or antigen binding fragment thereof to the patient; and c) instructions providing subcutaneously administering an anti-CD40 antibody or antigen binding fragment thereof to a patient in need thereof as a dose of about 3 to about 30 mg active ingredient per kilogram of a human subject, three times, once every other week, followed by monthly dosing of about 3 to about 30 mg, such as 10 mg, active ingredient per kilogram of a human subject, or at about 150 mg, about 300 mg or about 600 mg, weekly, bi-weekly or monthly during a maintenance regimen.

In one specific embodiment, a use is provided, of a) a liquid pharmaceutical composition comprising an anti-CD40 antibody, a buffer, a stabilizer and a solubilizer, and b) means for subcutaneously administering the anti-CD40 antibody to a patient having Sjögren's syndrome, for the manufacture of a medicament for the treatment of Sjögren's syndrome, wherein the anti-CD40 antibody:
  i) is to be intravenously administered to the patient with a dose of about 3 to about 30 mg, such as 10 mg, active ingredient per kilogram of a human subject, three times, once every other week; and
  ii) thereafter, is to be intravenously administered to the patient as monthly doses of about 3 to about 30 mg, such as 10 mg, active ingredient per kilogram of a human subject, wherein said anti-CD40 antibody is selected from the group consisting of:
  a) an anti-CD40 antibody comprising an immunoglobulin VH domain comprising the amino acid sequence of SEQ ID NO: 7 and an immunoglobulin VL domain comprising the amino acid sequence of SEQ ID NO: 8;
  b) an anti-CD40 antibody comprising an immunoglobulin VH domain comprising the hypervariable regions set forth as SEQ ID NO: 1, SEQ ID NO: 2, and SEQ ID NO: 3 and an immunoglobulin VL domain comprising the hypervariable regions set forth as SEQ ID NO: 4, SEQ ID NO: 5 and SEQ ID NO: 6;
  c) an anti-CD40 antibody comprising an immunoglobulin VH domain comprising the amino acid sequence of SEQ ID NO: 7 and an immunoglobulin VL domain comprising the amino acid sequence of SEQ ID NO: 8, and an Fc region of SEQ ID NO: 13;
  d) an anti-CD40 antibody comprising an immunoglobulin VH domain comprising the amino acid sequence of SEQ ID NO: 7 and an immunoglobulin VL domain comprising the amino acid sequence of SEQ ID NO: 8, and an Fc region of SEQ ID NO: 14;
  e) an anti-CD40 antibody comprising a silent Fc IgG1 region: and
  f) an anti-CD40 antibody comprising the heavy chain amino acid sequence of SEQ ID NO: 9 and the light chain amino acid sequence of SEQ ID NO: 10; or the heavy chain amino acid sequence of SEQ ID NO: 11 and the light chain amino acid sequence of SEQ ID NO: 12.

In another specific embodiment, a use is provided, of a) a liquid pharmaceutical composition comprising an anti-CD40 antibody, a buffer, a stabilizer and a solubilizer, and b) means for subcutaneously administering the anti-CD40 antibody to a patient having Sjögren's syndrome, for the manufacture of a medicament for the treatment of Sjögren's syndrome, wherein the anti-CD40 antibody:
  i) is to be subcutaneously administered to the patient with a dose of about 150 mg active substance, about 300 mg active substance or about 600 mg active substance (weekly or bi-weekly); and
  ii) thereafter, is to be subcutaneously administered to the patient as weekly, biweekly or monthly (every four weeks) doses of about 150 mg active substance, about 300 mg active substance or about 600 mg active substance, wherein said anti-CD40 antibody is selected from the group consisting of:
  a) an anti-CD40 antibody comprising an immunoglobulin VH domain comprising the amino acid sequence of SEQ ID NO: 7 and an immunoglobulin VL domain comprising the amino acid sequence of SEQ ID NO: 8;
  b) an anti-CD40 antibody comprising an immunoglobulin VH domain comprising the hypervariable regions set forth as SEQ ID NO: 1, SEQ ID NO: 2, and SEQ ID NO: 3 and an immunoglobulin VL domain comprising the hypervariable regions set forth as SEQ ID NO: 4, SEQ ID NO: 5 and SEQ ID NO: 6;
  c) an anti-CD40 antibody comprising an immunoglobulin VH domain comprising the amino acid sequence of SEQ ID NO: 7 and an immunoglobulin VL domain comprising the amino acid sequence of SEQ ID NO: 8, and an Fc region of SEQ ID NO: 13;
  d) an anti-CD40 antibody comprising an immunoglobulin VH domain comprising the amino acid sequence of SEQ ID NO: 7 and an immunoglobulin VL domain comprising the amino acid sequence of SEQ ID NO: 8, and an Fc region of SEQ ID NO: 14;
  e) an anti-CD40 antibody comprising a silent Fc IgG1 region: and
  f) an anti-CD40 antibody comprising the heavy chain amino acid sequence of SEQ ID NO: 9 and the light chain amino acid sequence of SEQ ID NO: 10; or the heavy chain amino acid sequence of SEQ ID NO: 11 and the light chain amino acid sequence of SEQ ID NO: 12.

Example 2. Pharmacology

1. Primary Pharmacology mAb1 binds to human CD40 with high affinity ($K_d$ of 0.3 nM). However, it does not bind to Fcγ receptors (including CD16) or mediate antibody-dependent cellular cytotoxicity or complement-dependent cytotoxicity. mAb1 inhibits recombinant CD154 (rCD154)-induced activation of human leukocytes, but does not induce PBMC proliferation or cytokine production by monocyte-derived dendritic cells (DCs). mAb1 binds human and non-human primate CD40 with very similar affinities.

In vivo, mAb1 blocks primary and secondary T cell-dependent antibody responses (TDAR), and can prolong survival of kidney allografts in non-human primates (Cordoba et al 2015). In addition, mAb1 can disrupt established germinal centers (GCs) in vivo.

The CD40 receptor occupancy and functional activity were simultaneously assessed in vitro using human whole blood cultures. Functional activity was quantified via CD154-induced expression of CD69 (the activation marker) on CD20 positive cells (B cells) and CD40 occupancy was monitored using fluorescently labeled mAb1. Almost complete CD40 occupancy by mAb1 was required for full inhibition of rCD154-induced CD69 expression.

2. Secondary Pharmacology

The effects of mAb1 on platelet function and blood hemostasis were investigated, indicating that mAb1 does not induce platelet aggregation responses, rather displays certain mild inhibitory effects on platelet aggregation at high concentrations.

Example 3. Non-Clinical Toxicology and Safety Pharmacology

Toxicology studies with mAb1 did not reveal any significant organ toxicities, including no evidence of thromboembolic events as reported in clinical trials with anti-CD154 mAbs (Kawai et al 2000). In a 13-week GLP rhesus monkey study (weekly dosing at 10, 50 and 150 mg/kg), increased lymphoid cellularity was noted in 5/22 animals which was considered to be due to ongoing infection, an observation consistent with the pharmacology of mAb1. Inflammatory lesions in the kidneys and lungs of 2 animals at 50 mg/kg were noted, and in one of the two animals, lesions in the eyes and trachea were also noted. While a direct effect of mAb1 on the kidney and lung cannot be excluded, the weight of evidence including confirmation of opportunistic pathogens, suggests these findings are likely secondary to mAb1-mediated immunosuppression and of an infectious origin. In view of these inflammatory findings, the No Observed Adverse Effect Level (NOAEL) for the 13-week toxicity study was set at 10 mg/kg. In a 26-week chronic toxicity study in cynomolgus monkeys, no adverse, mAb1-related findings were discovered. Based on these data, the NOAEL was set at 150 mg/kg (26-week). The mean (all animals) $C_{max,ss}$ was 44, 3235, and 9690 μg/mL at 1, 50, and 150 (NOAEL) mg/kg S.C. weekly, respectively. The NOAEL derived from the 26-week cynomolgus monkey study is considered the most relevant for supporting the clinical dosing regimen.

Post-mortem histological and immuno-histological evaluation revealed a decrease in GCs in cortical B-cell areas of the spleen and lymphatic tissues. The recovery animals showed some cases of increased lymph node cellularity with normal T cell areas and increased B cell areas, which is consistent with reconstitution of GCs after drug withdrawal. Recovery animals were able to mount primary TDAR to keyhole limpet hemocyanin (KLH) immediately after blood levels of mAb1 dropped below the level necessary for full receptor occupancy.

Because of the complete inhibition of T cell-dependent antibody responses (TDAR), KLH, the formation of anti-drug antibodies (ADA) to mAb1 is not expected and therefore ADA-related side effects are considered unlikely when concentrations of mAb1 are maintained continuously at pharmacological levels.

Tissue cross-reactivity studies revealed that CD40 is not only present on immune cells, but also in various tissues. This is mainly due to its expression on endothelial and epithelial cells, where CD40 is involved in signaling such as responding to wound healing processes, upregulation of virus-defense, and inflammatory-related mediators. An antagonistic anti-CD40 monoclonal antibody like mAb1 is not expected to contribute to inflammatory processes, which was confirmed by in vitro studies using human umbilical vein endothelial cells (HUVEC).

Full guideline-conform reproductive toxicity studies have not been conducted thus far. However, a dose-range finding, embryo-fetal development (EFD) study in rabbits has been conducted in order to confirm the rabbit as relevant reproductive toxicology species. No effects on embryo-fetal development were seen and there was no treatment-related fetal external malformation in any group.

In conclusion, the nonclinical data support the first multiple dose studies in patients with primary Sjögren's syndrome.

Example 4. Non-Clinical Pharmacokinetics and Pharmacodynamics

1. Pharmacokinetics (PK)

Typical for IgG immunoglobulins, the primary route of elimination of mAb1 is likely via proteolytic catabolism, occurring at sites that are in equilibrium with plasma. In addition, binding and internalization of mAb1-CD40 complexes resulted in rapid and saturable clearance routes. This was illustrated by non-linear mAb1 serum concentration-time profiles showing an inflection point at about 10-20 μg/mL. The contribution of the CD40-mediated clearance to the overall clearance depends on mAb1 concentration, together with levels of CD40 expression, internalization and receptor turnover rates. For serum concentrations of mAb1 >10-20 μg/mL, linear kinetics are expected, while non-linear kinetics emerged at lower concentrations.

2. Pharmacodynamics (PD)

In a PK/PD study in cynomolgus monkeys, the inflection point (about 10 μg/mL) in the PK profiles was associated with a drop of CD40 saturation, as determined in an independent lymphocyte target saturation assay. As such this inflection point is viewed as a marker for the level of saturation of CD40, and an evidence for target engagement.

The link between CD40 occupancy and pharmacodynamic activity was further demonstrated in rhesus monkeys immunized with KLH. Monkeys were immunized with KLH three times (the first was about 3 weeks prior to dosing, the second was 2 weeks after mAb1 administration, and the third was after complete wash-out of mAb1). CD40 occupancy by mAb1 at plasma concentrations >40 μg/mL at the time of the second KLH vaccination completely prevented recall antibody responses. Once mAb1 was cleared, all animals mounted a full memory antibody response to the third KLH. These results suggest that the function of pre-existing memory B cells were not affected. After complete elimination of mAb1, immunization with tetanus toxoid (TTx) led to anti-TTx-IgG/IgM titers similar to non-treated animals and demonstrated that full TDAR was regained after mAb1 elimination.

3. Immunogenicity

As expected from an immunosuppressive drug, immunogenicity data in rhesus monkey (single dose) are in agreement with the results from the KLH-TDAR experience and confirmed that no immune response against mAb1 could be mounted under full CD40 occupancy by mAb1.

4. Therapeutic Regimens

Based on the pharmacokinetics and pharmacodynamic profiles of mAb1, and the result from pre-clinical and clinical studies of mAb1, the following therapeutic regimens may be used.

Figure 24A:
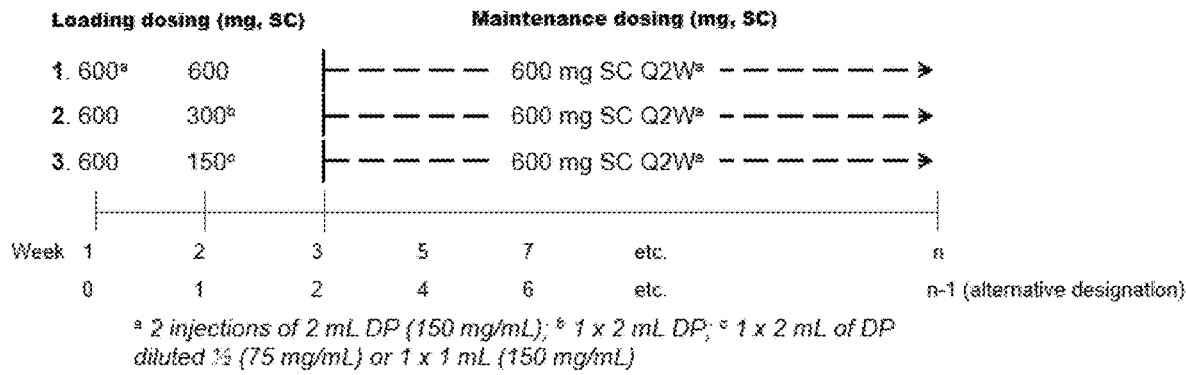
FIGS. 24A, 24B and 24C are graphical representations of possible weekly loading doses of the active ingredient given subcutaneously followed by bi-weekly maintenance regimen of the active ingredient (subcutaneously).

In one embodiment (cf. FIG. 24A, 1), the mAb1 therapeutic regimen consists of a loading dosing consisting of two doses of 600 mg mAb1, administered with one week between the two doses, followed by a maintenance dosing consisting of doses of 600 mg mAb1, administered every 2 weeks (Q2W). The 600 mg dose is preferably administered subcutaneously; through 2 injections of 2 mL drug product (150 mg/mL).

In another embodiment (cf. FIG. 24A, 2), the mAb1 therapeutic regimen consists of a loading dosing consisting of a first dose of 600 mg mAb1, and a second dose of 300 mg mAb1, wherein the second dose is administered one week after the first dose, followed by a maintenance dosing consists of doses of 600 mg mAb1, administered every 2 weeks (Q2W). The 300 mg dose is preferably administered subcutaneously; through 1 injection of 2 mL drug product (150 mg/mL). The 600 mg dose is preferably administered subcutaneously; through 2 injections of 2 mL drug product (150 mg/mL).

In yet another embodiment (cf. FIG. 24A, 3), the mAb1 therapeutic regimen consists of a loading dosing consisting of a first dose of 600 mg mAb1, and a second dose of 150 mg mAb1, wherein the second dose is administered one week after the first dose, followed by a maintenance dosing consists of doses of 600 mg mAb1, administered every 2 weeks (Q2W). The 150 mg dose is preferably administered subcutaneously; through 1 injection of 1 mL drug product (150 mg/mL), alternatively through 1 injection of 2 mL drug product diluted ½ times (75 mg/mL). The 600 mg dose is preferably administered subcutaneously; through 2 injections of 2 mL drug product (150 mg/mL).

Figure 24B:
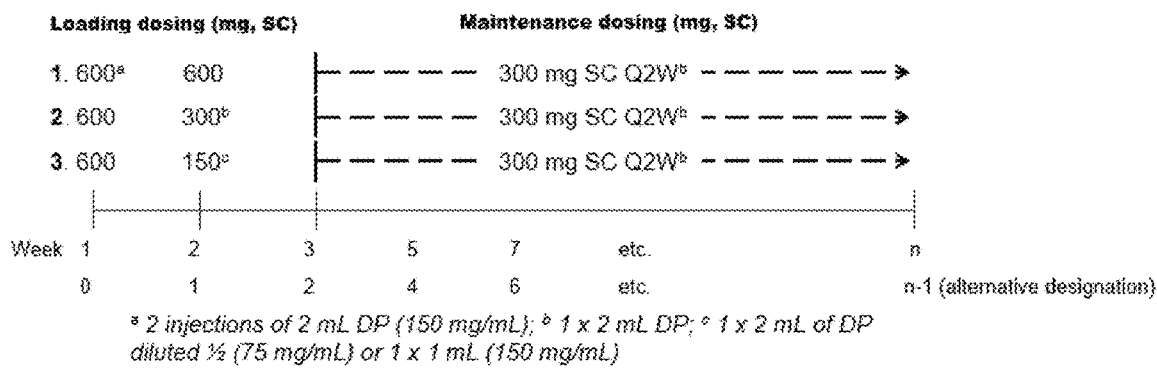

In one embodiment (cf. FIG. 24B, 1), the mAb1 therapeutic regimen consists of a loading dosing consisting of two doses of 600 mg mAb1, administered with one week between the two doses, followed by a maintenance dosing consisting of doses of 300 mg mAb1, administered every 2 weeks (Q2W). The 600 mg dose is preferably administered subcutaneously; through 2 injections of 2 mL drug product (150 mg/mL). The 300 mg dose is preferably administered subcutaneously; through 1 injection of 2 mL drug product (150 mg/mL).

In another embodiment (cf. FIG. 24B, 2), the mAb1 therapeutic regimen consists of a loading dosing consisting of a first dose of 600 mg mAb1, and a second dose of 300 mg mAb1, wherein the second dose is administered one week after the first dose, followed by a maintenance dosing consists of doses of 300 mg mAb1, administered every 2 weeks (Q2W). The 300 mg dose is preferably administered subcutaneously; through 1 injection of 2 mL drug product (150 mg/mL). The 600 mg dose is preferably administered subcutaneously; through 2 injections of 2 mL drug product (150 mg/mL).

In yet another embodiment (cf. FIG. 24B, 3), the mAb1 therapeutic regimen consists of a loading dosing consisting of a first dose of 600 mg mAb1, and a second dose of 150 mg mAb1, wherein the second dose is administered one week after the first dose, followed by a maintenance dosing consists of doses of 300 mg mAb1, administered every 2 weeks (Q2W). The 150 mg dose is preferably administered subcutaneously; through 1 injection of 1 mL drug product (150 mg/mL), alternatively through 1 injection of 2 mL drug product diluted ½ times (75 mg/mL). The 600 mg dose is preferably administered subcutaneously; through 2 injections of 2 mL drug product (150 mg/mL). The 300 mg dose is preferably administered subcutaneously; through 1 injection of 2 mL drug product (150 mg/mL).

Figure 24C:
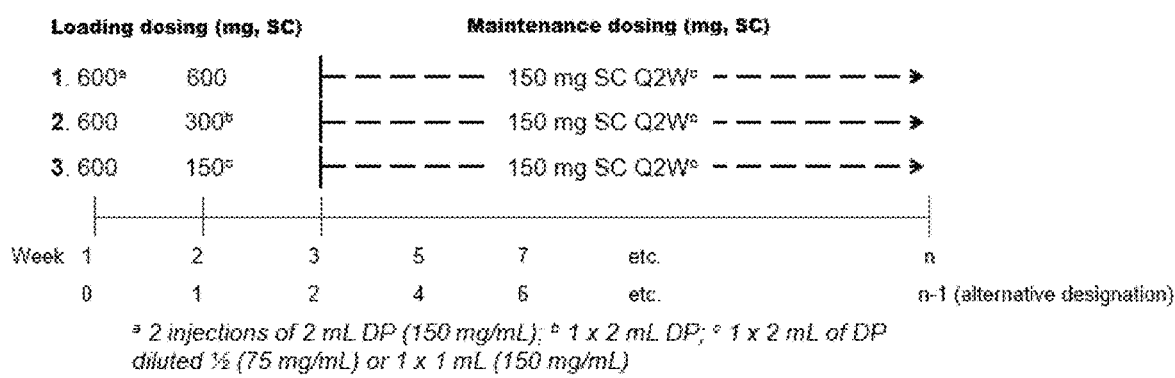

In one embodiment (cf. FIG. 24C, 1), the mAb1 therapeutic regimen consists of a loading dosing consisting of two doses of 600 mg mAb1, administered with one week between the two doses, followed by a maintenance dosing consisting of doses of 150 mg mAb1, administered every 2 weeks (Q2W). The 600 mg dose is preferably administered subcutaneously; through 2 injections of 2 mL drug product (150 mg/mL). The 150 mg dose is preferably administered subcutaneously; through 1 injection of 1 mL drug product (150 mg/mL), alternatively through 1 injection of 2 mL drug product diluted 12 times (75 mg/mL).

In another embodiment (cf. FIG. 24C, 2), the mAb1 therapeutic regimen consists of a loading dosing consisting of a first dose of 600 mg mAb1, and a second dose of 300 mg mAb1, wherein the second dose is administered one week after the first dose, followed by a maintenance dosing consists of doses of 150 mg mAb1, administered every 2 weeks (Q2W). The 300 mg dose is preferably administered subcutaneously; through 1 injection of 2 mL drug product (150 mg/mL). The 600 mg dose is preferably administered subcutaneously; through 2 injections of 2 mL drug product (150 mg/mL). The 150 mg dose is preferably administered subcutaneously; through 1 injection of 1 mL drug product (150 mg/mL), alternatively through 1 injection of 2 mL drug product diluted 12 times (75 mg/mL).

In yet another embodiment (cf. FIG. 24C, 3), the mAb1 therapeutic regimen consists of a loading dosing consisting of a first dose of 600 mg mAb1, and a second dose of 150 mg mAb1, wherein the second dose is administered one week after the first dose, followed by a maintenance dosing consists of doses of 150 mg mAb1, administered every 2 weeks (Q2W). The 150 mg dose is preferably administered subcutaneously; through 1 injection of 1 mL drug product (150 mg/mL), alternatively through 1 injection of 2 mL drug product diluted ½ times (75 mg/mL). The 600 mg dose is preferably administered subcutaneously; through 2 injections of 2 mL drug product (150 mg/mL). The 300 mg dose is preferably administered subcutaneously; through 1 injection of 2 mL drug product (150 mg/mL).

Figure 25A:
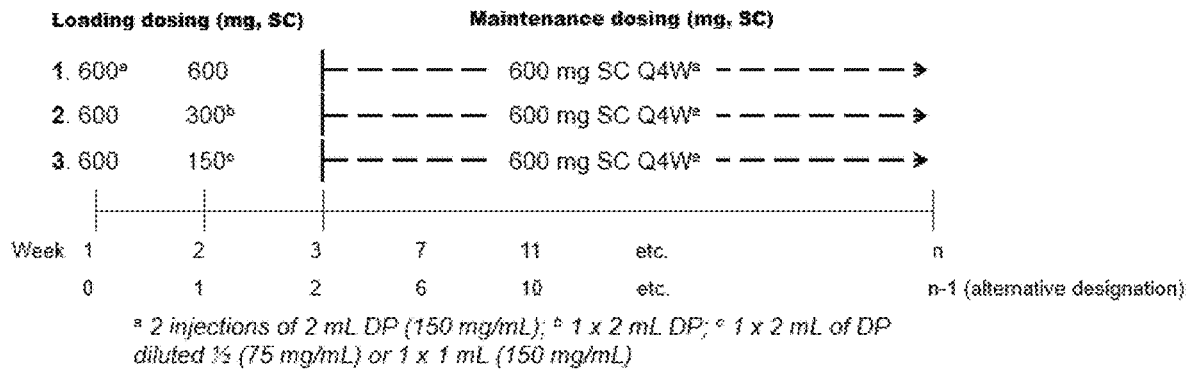
FIG. 25A, is a graphical representation of possible weekly loading doses of the active ingredient given subcutaneously followed by every 4 weeks administration of the active ingredient (subcutaneously)

In a further embodiment, (cf. FIG. 25A, 1), the mAb1 therapeutic regimen consists of a loading dosing consisting of two doses of 600 mg mAb1, administered with one week between the two doses, followed by a maintenance dosing consisting of doses of 600 mg mAb1, administered every 4 weeks (Q4W). The 600 mg dose is preferably administered subcutaneously; through 2 injections of 2 mL drug product (150 mg/mL).

In another embodiment (cf. FIG. 25A, 2), the mAb1 therapeutic regimen consists of a loading dosing consisting of a first dose of 600 mg mAb1, and a second dose of 300 mg mAb1, wherein the second dose is administered one week after the first dose, followed by a maintenance dosing consists of doses of 600 mg mAb1, administered every 4 weeks (Q4W). The 300 mg dose is preferably administered subcutaneously; through 1 injection of 2 mL drug product (150 mg/mL). The 600 mg dose is preferably administered subcutaneously; through 2 injections of 2 mL drug product (150 mg/mL).

In yet another embodiment (cf. FIG. 25A, 3), the mAb1 therapeutic regimen consists of a loading dosing consisting of a first dose of 600 mg mAb1, and a second dose of 150 mg mAb1, wherein the second dose is administered one week after the first dose, followed by a maintenance dosing consists of doses of 600 mg mAb1, administered every 4 weeks (Q4W). The 150 mg dose is preferably administered subcutaneously; through 1 injection of 1 mL drug product (150 mg/mL), alternatively through 1 injection of 2 mL drug product diluted ½ times (75 mg/mL). The 600 mg dose is preferably administered subcutaneously; through 2 injections of 2 mL drug product (150 mg/mL).

Figure 25B:
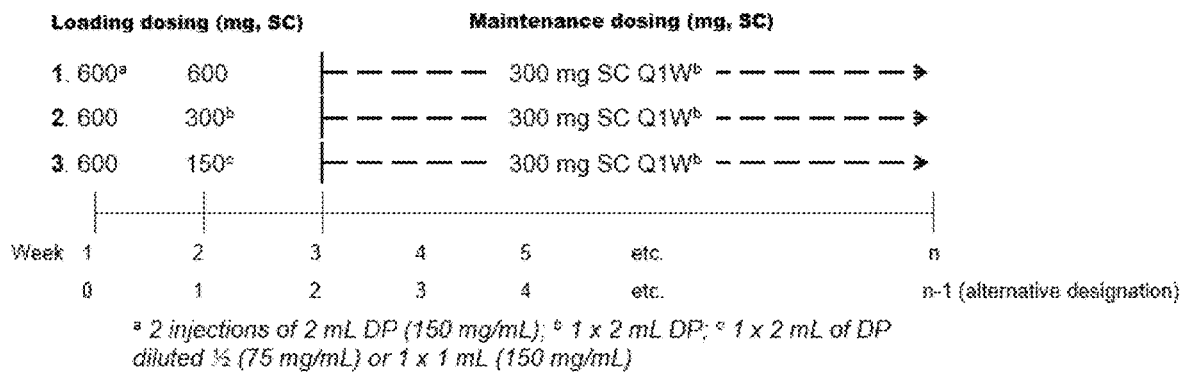
FIG. 25B is a graphical representation of possible weekly loading doses of the active ingredient given subcutaneously followed by every week administration of the active ingredient (subcutaneously).

In a further embodiment, (cf. FIG. 25B, 1), the mAb1 therapeutic regimen consists of a loading dosing consisting of two doses of 600 mg mAb1, administered with one week between the two doses, followed by a maintenance dosing consisting of doses of 300 mg mAb1, administered every week (Q1W). The 600 mg dose is preferably administered subcutaneously; through 2 injections of 2 mL drug product (150 mg/mL). The 300 mg dose is preferably administered subcutaneously; through 1 injection of 2 mL drug product (150 mg/mL).

In another embodiment (cf. FIG. 25B, 2), the mAb1 therapeutic regimen consists of a loading dosing consisting of a first dose of 600 mg mAb1, and a second dose of 300 mg mAb1, wherein the second dose is administered one week after the first dose, followed by a maintenance dosing consists of doses of 300 mg mAb1, administered every week (Q1W). The 300 mg dose is preferably administered subcutaneously; through 1 injection of 2 mL drug product (150 mg/mL). The 600 mg dose is preferably administered subcutaneously; through 2 injections of 2 mL drug product (150 mg/mL).

In yet another embodiment (cf. FIG. 25B, 3), the mAb1 therapeutic regimen consists of a loading dosing consisting of a first dose of 600 mg mAb1, and a second dose of 150 mg mAb1, wherein the second dose is administered one week after the first dose, followed by a maintenance dosing consists of doses of 300 mg mAb1, administered every week (Q1W). The 150 mg dose is preferably administered subcutaneously; through 1 injection of 1 mL drug product (150 mg/mL), alternatively through 1 injection of 2 mL drug product diluted ½ times (75 mg/mL). The 300 mg dose is preferably administered subcutaneously; through 1 injection of 2 mL drug product (150 mg/mL). The 600 mg dose is preferably administered subcutaneously; through 2 injections of 2 mL drug product (150 mg/mL).

An advantage of having a therapeutic regimen divided into a loading dosing part and a maintenance dosing part is that it allows for optimal therapeutic effect.

For all therapeutic regimens described herein, the purpose of the loading dosing is to achieve target saturation (plasma concentrations close to 40 µg/mL) and thus onset of therapeutic effect, and the purpose of the maintenance dosing is to sustain efficacy.

Example 5. Human Safety and Tolerability Data

The safety, tolerability, PK and PD activity of mAb1 are being assessed in an ongoing, randomized, double-blind, placebo-controlled, single-ascending dose study of mAb1 in healthy subjects and patients with rheumatoid arthritis (RA). A total of 48 subjects have been enrolled: 36 healthy subjects who received single doses of mAb1 up to 3 mg/kg IV or S.C., and 12 patients with RA, 6 of whom received single doses of mAb1 at 10 mg/kg IV. Overall, single doses up to 3 mg/kg mAb1 in healthy volunteers and a single of 10 mg/kg mAb1 in RA patients have been safe and well tolerated and no suspected serious adverse events (SAEs) have occurred. An investigation of the 30 mg/kg IV dose is ongoing in RA patients. As this study is still ongoing, all clinical data are preliminary in nature and based on interim analyses conducted up to a dose of 10 mg/kg in RA patients.

Example 6. Human Pharmacokinetics and Pharmacodynamics (Healthy Volunteers and Rheumatoid Arthritis Patients)

In healthy subjects as well as in patients with rheumatoid arthritis, after single IV or SC administration, CFZ533 PK profiles were consistent with target mediated disposition resulting in non-linear PK profiles and more rapid clearance when CD40 receptor occupancy dropped below approximately 90%.

Despite some inter-individual variability in the PK profiles from the Chinese subjects, the disposition of CFZ533 in Chinese subjects was generally similar as for non-Chinese subjects, and the target engagement was also similar (about 4 weeks) after 3 mg/kg IV CFZ533. At this dose level, similar PK/PD profiles were demonstrated through free CFZ533 profiles in plasma, CD40 occupancy on peripheral B cells measuring free CD40 and total CD40, and total sCD40 concentrations in plasma.

After SC administration in healthy subjects, CFZ533 was rapidly absorbed and distributed in line with what is expected for a typical IgG1 antibody in human. At 3 mg/kg SC, CFZ533 generally peaked at 3 days post-dose (7 days for 2 subjects), and 1 week after dosing plasma concentrations were in the same range as for after IV. At 3 mg/kg SC, duration of target engagement was also about 4 weeks.

In patients with rheumatoid arthritis at 10 mg/kg IV, as measured by free CD40 on whole blood B cells compared to mean pre-dose, and total sCD40 profiles in plasma, full CD40 occupancy was generally maintained for 8 weeks. At 30 mg/kg IV, PK and total sCD40 profiles in plasma are consistent with duration of target engagement of 16 weeks.

In healthy subjects CD40 engagement by CFZ533 generally led to a decrease in total CD40 on peripheral B cells by about 50%, tracking CD40 occupancy on B cells as measured by free CD40 on B cells. This is likely due to internalization and/or shedding of the membrane bound CD40 upon binding to CFZ533. In patients with rheumatoid arthritis the decrease in total CD40 on peripheral B cells was not confirmed.

The relationship between CFZ533 in plasma and CD40 occupancy on whole blood B cells (free CD40 on B cells) was defined, and CFZ533 concentrations of 0.3-0.4 µg/mL were associated with full (defined as ≥90%) CD40 occupancy on whole blood B cells.

More generally, non-specific and specific elimination pathways have been identified for CFZ533. The non-specific and high capacity pathway mediated by FcRn receptors is commonly shared by endogenous IgGs. The specific target mediated disposition of CFZ533 led to the formation of CFZ533-CD40 complexes that were partially internalized (with subsequent lysosomal degradation) and/or shed from the membrane. Target-mediated processes resulted in saturable and nonlinear disposition of CFZ533. The formation of CFZ533-CD40 complexes was dose/concentration-dependent, with saturation occurring at high concentrations of CFZ533.

Overall, the disposition of CFZ533 is dependent on the relative contribution of the specific (target mediated) and non-specific elimination pathways to the overall clearance of CFZ533. Nonlinear PK behavior was observed when CFZ533 concentrations were lower than that of the target, while at higher concentrations with CD40 receptors being saturated, the non-specific pathways predominate and the elimination of CFZ533 was linear.

As expected for a typical IgG1 antibody targeting a membrane bound receptor and demonstrating target mediated disposition, the extent of exposure of CFZ533 (AUClast) increased more than the increase in dose (hyperproportionality). Consequently, this is expected to be associated with a decrease in the volume of distribution and clearance of CFZ533 at higher doses.

One subject at 1 mg/kg IV CFZ533 (1 week full CD40 occupancy) developed specific antibodies to CFZ533 detected 6 weeks after CFZ533 plasma concentrations were below the limit of quantification, and definitively too low to block any CD40 pathway-relevant effects in tissue. The presence of anti-drug antibodies (ADAs) in this subject did not compromised exposure, and was not associated with an immune related safety signal. This corresponds to an ADA incidence of 2% in this study.

A single dose of 3 mg/kg (IV and SC) of CFZ533 transiently suppressed anti-KLH responses to the first KLH immunization, at CFZ533 concentrations corresponding to full (≥90%) receptor occupancy (for about 3-4 weeks). Anti-KLH primary responses were detected in all subjects as CFZ533 concentration, and accompanying receptor occupancy, declined. All subjects were able to mount recall responses to a second KLH immunization (administered after loss of receptor occupancy was anticipated).

Data suggest that CD40 engagement by CFZ533 prevented recombinant human CD154 (rCD154) mediated B cell activation in human whole blood. The rCD154-induced-CD69 expression on B cells was generally suppressed during a period corresponding to full CD40 occupancy on B cells. When CD40 occupancy was incomplete, the functional activity of rCD154 was restored.

There was no evidence of any effect of CFZ533 on immunophenotyping data.

Example 7. A Multi-Center, Randomized, Double-Blind, Placebo-Controlled, Parallel Group study to assess the safety, tolerability, pharmacokinetics and preliminary efficacy of CFZ533 in patients with primary Sjögren's syndrome To assess the suitability of utilizing a human, anti-CD40 monoclonal antibodies with silenced ADCC activity in treatment of Sjögren's syndrome, a clinical study was designed and conducted using the antibody CFZ533, herein also called mAb1.

Sjögren syndrome (SS) may be primary or is often associated with other autoimmune diseases such as systemic lupus erythematosus (SLE) or rheumatoid arthritis (RA). In this case, SS is called secondary. Patients with secondary Sjögren's syndrome have been excluded from the CFZ533 clinical trials because the primary disease (e.g. RA or SLE) and its concomitant treatments would significantly interfere with assessing primary SS. For example, joint involvement/damage in RA would make the arthralgia domain of ESS-DAI non-interpretable or anti-TNF treatment would not be compatible with the use of CFZ533. However, as the pathogenesis of secondary SS is driven by the same pathobiological events as in pSS, such as germinal center formation and autoantibody formation mediated by the abnormal activation of the CD40-CD154 pathway, treatment with CFZ533 is expected to be beneficial in secondary SS, warranting dedicated clinical trials.

Primary Sjögren's syndrome (pSS) is a systemic, progressive autoimmune disease characterized by formation of ectopic germinal centers in exocrine glands and secretory gland dysfunction. A subset of patients also develops extraglandular manifestations. CFZ533 is a novel monoclonal antibody that potently and selectively blocks CD40, a costimulatory pathway receptor essential for germinal center reactions and other immune mediated functions implicated in pSS pathogenesis. A randomized, double-blind, placebo-controlled, multi-centric, partial cross-over Phase IIa Proof of Concept (PoC) study was conducted to evaluate the safety, tolerability and efficacy of CFZ533 in patients with pSS.

Several lines of evidence suggest that disease pathology driven by or closely related to the CD40-CD154 pathway is essential in pSS. Hallmark diagnostic features of pSS include B cell hyper-reactivity such as formation of germinal center like structures in salivary glands (observed in 18-59% of patients) and autoantibodies (Vossenkamper et al 2012). In pSS lesions, activated T cells predominate and are capable of provoking B cell hyperactivity, Ig secretion and facilitating destruction of glands (Manganelli and Fietta 2003). In addition, T and B cell infiltrates in these patients' salivary glands show upregulation of CD40 and CD154. CD40-CD154 mediated tissue inflammation may also contribute to pSS pathogenesis.

Furthermore, CD40-CD154 mediated tissue inflammation may also contribute to Pss pathogenesis. Epithelial cell lines derived from pSS patients have constitutively upregulated surface CD40 (Dimitriou et al 2002). Increased levels of micro-particles derived from platelets and also from leukocytes together with elevated sCD154 concentrations have been reported in pSS sera (Sellam et al 2009).

1. Design of the Proof of Concept Study CCFZ533X2203 in SS

This is a double-blind followed by open-label, randomized, placebo-controlled, parallel-group, non-confirmatory study to assess the safety, tolerability, pharmacokinetics, and preliminary clinical efficacy of multiple doses of CFZ533 in the following Cohorts 1 and 2:

Cohort 1: 3 mg/kg CFZ533 administered subcutaneously in patients with pSS, in a double-blind and placebo-controlled fashion, followed by open-label treatment;

Cohort 2: 10 mg/kg CFZ533 administered by intravenous infusion in patients with pSS, in a double-blind and placebo-controlled fashion, followed by open label treatment.

These cohorts were followed by an open label, randomized, parallel group, non-confirmatory part of Cohort 3:

Cohort 3: In treatment arm 1, CFZ533 was given at 600 mg s.c. weekly on 4 occasions (loading regimen), followed by 300 mg s.c. weekly on 9 occasions (maintenance regimen starting on study Day 29).

In treatment arm 2, the loading regimen was a single i.v. dose of 10 mg/kg CFZ533 (on study Day 1), followed by 300 mg s.c. weekly on 12 occasions (maintenance regimen starting on study Day 8).

In Cohorts 1 and 2, randomization will be stratified by baseline intake of oral corticosteroids (yes/no). There will be no stratification in Cohort 3.

The study comprises three periods for Cohort 1 and Cohort 2:

1. placebo-controlled period (from Day 1, Week 1 to completion of pre-dose assessments on Day 85, Week 13), during which 4 doses of CFZ533 or placebo were administered on top of the standard of care therapy, (e.g., low dose corticosteroid) that is necessary to treat pSS;
2. open-label period (from dosing on Day 85, Week 13 to completion of assessments on Day 169, Week 25), when all patients received 4 doses of open-label CFZ533 treatment, and
3. follow-up period (Weeks 25-32), when patients are followed up without study medication.

FIG. 1 is a schematic representation of the study design of Cohorts 1 and 2.

Cohort 3 comprises two periods:

1. open-label treatment period (from dosing on Day 1, Week 1 to last dose and completion of assessments on Day 85, Week 13),
2. follow-up period (from Week 13 after completion of last dose to Day 141, Week 21), when patients are followed up for 8 weeks without study medication.

In the open-label treatment period, treatment arm 1 dosing starts with CFZ533 600 mg s.c. once weekly for 4 weeks; in treatment arm 2, dosing starts with CFZ533 10 mg/kg i.v. on Day 1.

Following that, dosing continues with CFZ533 300 mg s.c. once weekly for 4 weeks (treatment arm 1) and 9 weeks (treatment arm 2), respectively.

Figure 2:
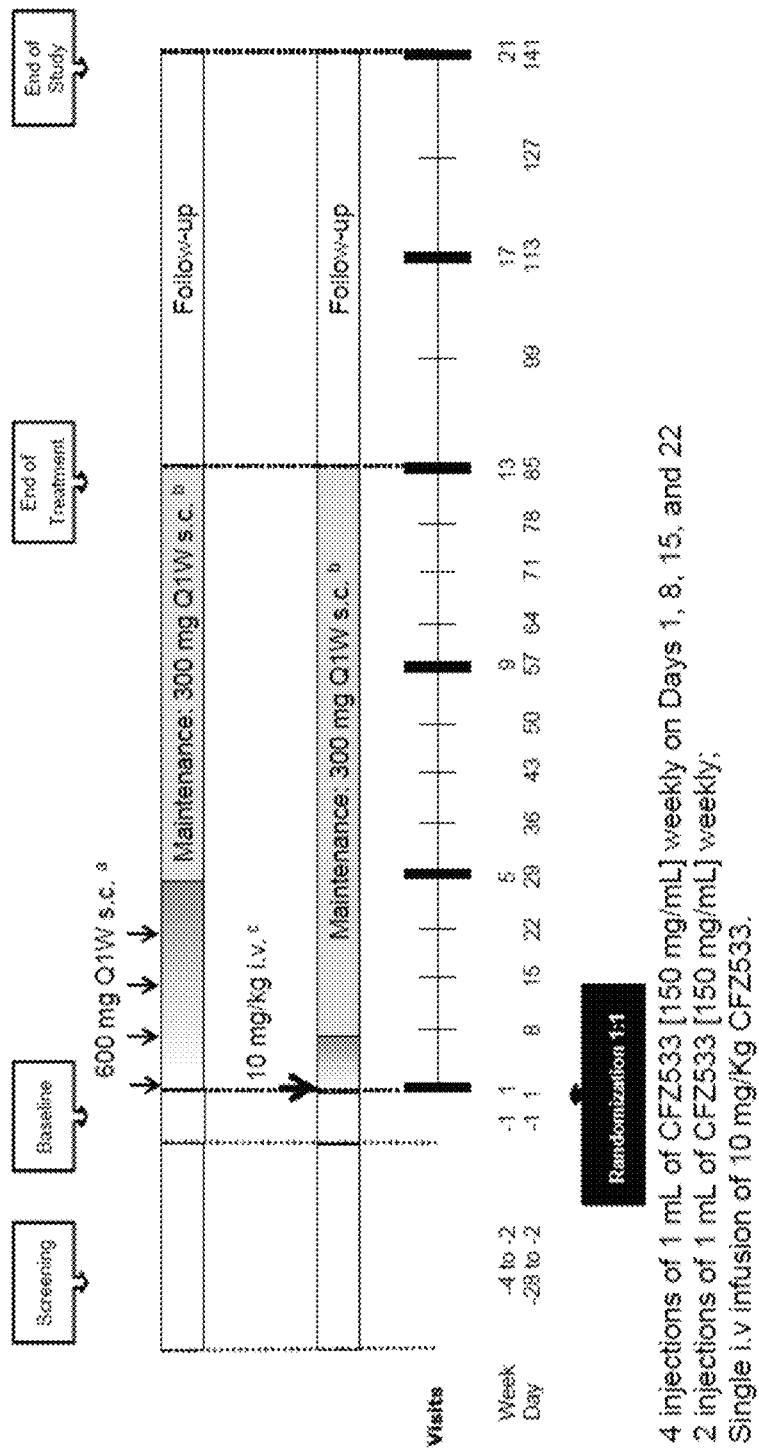
FIG. 2 is a schematic representation of the study design of the third cohort of the proof of concept study for CFZ533 in pSS patients (CCFZ533X2203).

FIG. 2 is a schematic representation of the study design of Cohort 3.

Cohort 1

This cohort randomized approximately 12 patients. For each patient, there was a screening period from Day −28 to Day −2. Patients who met the eligibility criteria at screening were admitted to baseline evaluations. Baseline evaluations were started from Day −6 to allow completion of assessments on Day −1 prior to the treatment on Day 1.

All baseline safety evaluation results were available prior to dosing and meeting eligibility criteria. Eligible patients entered the placebo-controlled period on Day 1 (Week 1) and were randomized at a 2:1 ratio to receive treatment with either CFZ533 or placebo. On Day 1, a dose of 3 mg/kg CFZ533 or placebo was administered by subcutaneous injection (s.c.), followed by PK, pharmacodynamics (PD) and safety assessments for up to 6 hours. Patients were discharged from the site on the same day after completion of all assessments provided there were no safety concerns.

Patients returned to the study center to receive three s.c. doses of either CFZ533 or placebo (same as they have received on Day 1) on Day 15 (Week 3), Day 29 (Week 5) and Day 57 (Week 9) respectively. Safety and efficacy assessments were conducted in these visits, PK and biomarker samples were collected.

On Day 85 (Week 13), after safety and other assessments that are assessments for the end of placebo-controlled period, all patients entered the open-label period and received an open-label s.c. dose of 3 mg/kg CFZ533. This was followed by three open-label s.c. doses of CFZ533 (3 mg/kg each) on Day 99 (Week 15), Day 113 (Week 17) and Day 141 (Week 21) respectively. Safety and efficacy assessments were conducted in these visits, PK and biomarker samples were collected. The blind of the controlled period was maintained for the investigator and the patient until the end of the study.

On Day 169 (Week 25), patients had assessments for the end of open-label period and entered follow-up period with no study medication administered. Patients returned to the study center for safety monitoring during this period.

The end of study visit occurred on Day 225 (Week 33), which included study completion evaluations followed by discharge from the study.

Cohort 2

When approximately 12 subjects had been enrolled in Cohort 1, Cohort 2 began enrollment to randomize approximately 30 patients to have approximately 24 patients completing 12 weeks treatment. The study design for Cohort 2 was identical as Cohort 1 with the exception of the dosing regimen which included multiple intravenous dosing of 10 mg/kg CFZ533 followed by PK, pharmacodynamics (PD) and safety assessments for up to 2 hours after the end of the infusion. Additionally, body weight was measured at every dosing visit to calculate the drug dosage according to the subject's actual weight (in Cohort 1, subject's baseline weight was used throughout study).

Cohort 3

Cohort 3 randomizes approximately 24 patients to have approximately 20 patients (10 in treatment arm 1, 10 in treatment arm 2) completing a 12-week treatment.

Patients can remain on their standard of care therapies provided that the treatments are maintained at a constant level during the study.

Safety assessments include physical examinations, ECGs, vital signs, standard clinical laboratory evaluations (hematology, blood chemistry, urinalysis, pregnancy test, blood coagulation), adverse event and serious adverse event monitoring.

All s.c. injections and i.v. infusions take place in a monitored facility. Patients are monitored closely for at least 6 hour after s.c. injection in Cohort 1, 2 hours after completion of i.v. infusion in Cohort 2. In Cohort 3, the patients are monitored for at least 1 hour after the completion of i.v. infusion and 30 minutes after s.c. injection, or longer at the discretion of the Investigator for vital signs, and signs or symptoms of adverse events including development of an injection reaction. Pharmacokinetic, pharmacodynamic, and safety assessments were made for up to 6 hours after s.c. injection in Cohort 1, 2 hours after the completion of i.v. infusion in Cohort 2, or 1 hour after the completion of the i.v. infusion and 30 minutes after the s.c. injection in Cohort 3. Subjects were discharged after these assessments, at the discretion of the Investigator, following satisfactory review of safety data.

PK assessment includes measurements of free CFZ533 in plasma.

Concurrent PD markers: CD40 saturation on peripheral blood B cells (free CD40 and total CD40 on B cells, Cohorts 1 and 2 only), total soluble CD40, and total soluble CD154 (optional, Cohorts 1 and 2 only) are measured in plasma of patients to allow PK/PD modeling. Additionally, autoantibodies are investigated as well as some exploratory biomarkers. Immunogenicity is assessed via the quasi-quantitative analysis of anti-CFZ533 antibodies.

In Cohort 1 and Cohort 2, optional labial biopsy is taken at baseline and at the end of the placebo controlled period (Day 85, Week 13).

An interim analysis (1st IA) is performed including approximately 12 patients who had completed the 12 weeks treatment period in Cohort 1. For these patients, key safety and tolerability data and preliminary efficacy is assessed.

Further safety and efficacy interim analyses is conducted to support decision making concerning the current clinical study, the Sponsor's clinical development projects in general or in case of any safety concerns.

2. Rationale of Study Design

Cohorts 1 and 2

Two different doses (3 mg/kg s.c. and 10 mg/kg i.v.) of CFZ533 were assessed in two separate cohorts.

A randomized, placebo-controlled, double-blind approach was used to eliminate potential bias in reporting safety and clinical efficacy data in this first, exploratory study in pSS patients.

Patients were randomized to CFZ533 or placebo in a 2:1 ratio in order to minimize exposure to placebo and to gather more data on CFZ533. Stratified randomization was done in order to limit imbalances between active and placebo arms in baseline intake of oral corticosteroids.

The open-label period administer CFZ533 to all patients including those who were administered placebo in the placebo-controlled period. This provides potential treatment benefit to these patients, and collect further safety and efficacy data for CFZ533 in pSS patients. After the open-label period, patients entered a follow up period for which a duration of 8 weeks (12 weeks after the last dosing with CFZ533) was chosen to allow sufficient time for monitoring safety and exploring duration of response.

In addition to safety, efficacy estimated by the European League Against Rheumatism (EULAR) Sjögren's Syndrome Disease Activity Index (ESSDAI) was chosen as a key endpoint of the study. The ESSDAI metric is well known to a person skilled in the art (see e.g. Seror et al. 2011a). The ESSDAI has been shown to be responsive in a retrospective analysis of a randomized controlled trial on rituximab, and was suggested to be a sensitive tool to assess efficacy of rituximab treatment (Moerman et al 2014). The authors reported a significant lower ESSDAI in the rituximab group compared to the placebo group at week 12 and week 24, demonstrating some effectiveness in reducing disease activity in this small study.

Similarly, the EULAR Sjögren's Syndrome Patient Reported Index (ESSPRI) is used in the study (see e.g. Seror et al. 2011b)

Cohort 3

Because of the key objective of this cohort, no placebo control is required, and open-label treatment is justified. In Cohort 3, two treatment arms are implemented to assess whether two loading regimens (multiple s.c. doses in treatment arm 1, or single i.v. administration in treatment arm 2), followed by a maintenance regimen (multiple s.c. doses, both arms), are set to 12 weeks (Day 1 to Day 85) to establish steady state conditions for CFZ533 concentrations in plasma at a level similar to trough concentrations observed in Cohort 2 (10 mg/kg i.v. regimen).

The follow-up period is set to 8 weeks (Day 85 to Day 141),
  (i) to follow the elimination of CFZ533 under conditions where the target is fully saturated (slow elimination), and under incomplete CD40 saturation (rapid elimination), and
  (ii) to characterize the capacity of the target mediated elimination pathway for CFZ533 after 12-week treatment.

3. Rationale of Dose/Regimen, Duration of Treatment

There is no previous experience with an anti-CD40 blocking agent exists in human primary Sjögren's syndrome. However, evidence points to involvement of CD40-dependent immune processes in the pathophysiology of the disease including the presence of lymphoid aggregates and germinal center-like structures in salivary glands of affected individuals, disease-specific autoantibodies and glandular expression of CD40 and its ligand. Pre-clinical and first-in-man study results suggest that complete CD40 receptor occupancy is required for full suppression of the T cell-dependent B cell function as well as blockade of the parenchymal CD40-related functions, and would be required to achieve maximal therapeutic benefit. For example, results from the 26-week toxicity study indicated that at 1 mg/kg CFZ533 weekly, full CD40 occupancy on peripheral B cells was measured but an incomplete pharmacological effect was observed in some animals (3/6), manifesting as a partial reduction in germinal centers.

This indicated that doses of greater than 1 mg/kg (weekly) of CFZ533 would be required for complete suppression of CD40-CD154 interactions and subsequent signaling events in tissue.

Cohort 1 (Subcutaneous, 3 mg/kg)

The highest subcutaneous dose of CFZ533 that has been tested in healthy volunteers is currently 3 mg/kg, and proved to be safe and well tolerated as a single dose to healthy volunteers. Doses of 1 and 3 mg/kg i.v. were associated with 1 and 4 weeks of full (defined as >90%) CD40 occupancy on peripheral blood B cells, respectively. Furthermore, ex vivo CD154 induced CD69 expression was suppressed for approximately 4 weeks using PBMC from healthy volunteers who had received 3 mg/kg CFZ533 i.v. CD40 occupancy was 90% (mean n=6; range 73-97%) at 4 weeks after a single subcutaneous dose of 3 mg/kg CFZ533.

Taken together, 3 mg/kg s.c. was chosen for the present Cohort 1 as this dosing has been safe and well tolerated in healthy volunteers and could result in the desired pharmacological and pharmacodynamic effect.

The 2-week dosing interval at the start was meant to ensure full CD40 saturation on peripheral B cells as well as complete suppression of CD40-CD154 interaction in tissues after subcutaneous administration. By the end of the 12-week treatment period, clinically meaningful changes in the primary endpoint and in other key efficacy and biomarker readouts were expected to occur. Based on published results with a single cycle of rituximab, significant clinical responses in pSS patients can be detected as early as at week 5, with maximum effect shown at week 12 (Meijer et al 2010). During the additional 12-week open label extension period, further data regarding longer term efficacy and safety of CFZ533 was collected.

Cohort 2 (Intravenous, 10 mg/kg)

The 10 mg/kg i.v. regimen was introduced to offer higher plasma exposures throughout the treatment period, in order to ensure complete and sustained CD40 pathway blockade in target tissues, in conditions where higher CD40 expression is likely. This regimen is supported by safety data in humans, adequate safety ratios from preclinical toxicological studies, relevant PD effects in tissues in non-human primates, and recently published data from ASKP1240.

Safety and Tolerability Confirmed in Humans:

A Phase 1 study (CCFZ533X2101), testing Single ascending doses (0.03 to 30 mg/kg) of CFZ533 i.v. and 3 mg/kg s.c., was completed and did not reveal major safety concern up to the highest dose tested (10 mg/kg i.v.). Based on clinical experience so far, the 10 mg/kg i.v. dosing regimen is anticipated to be safe and tolerable in pSS patients.

Figure 3:
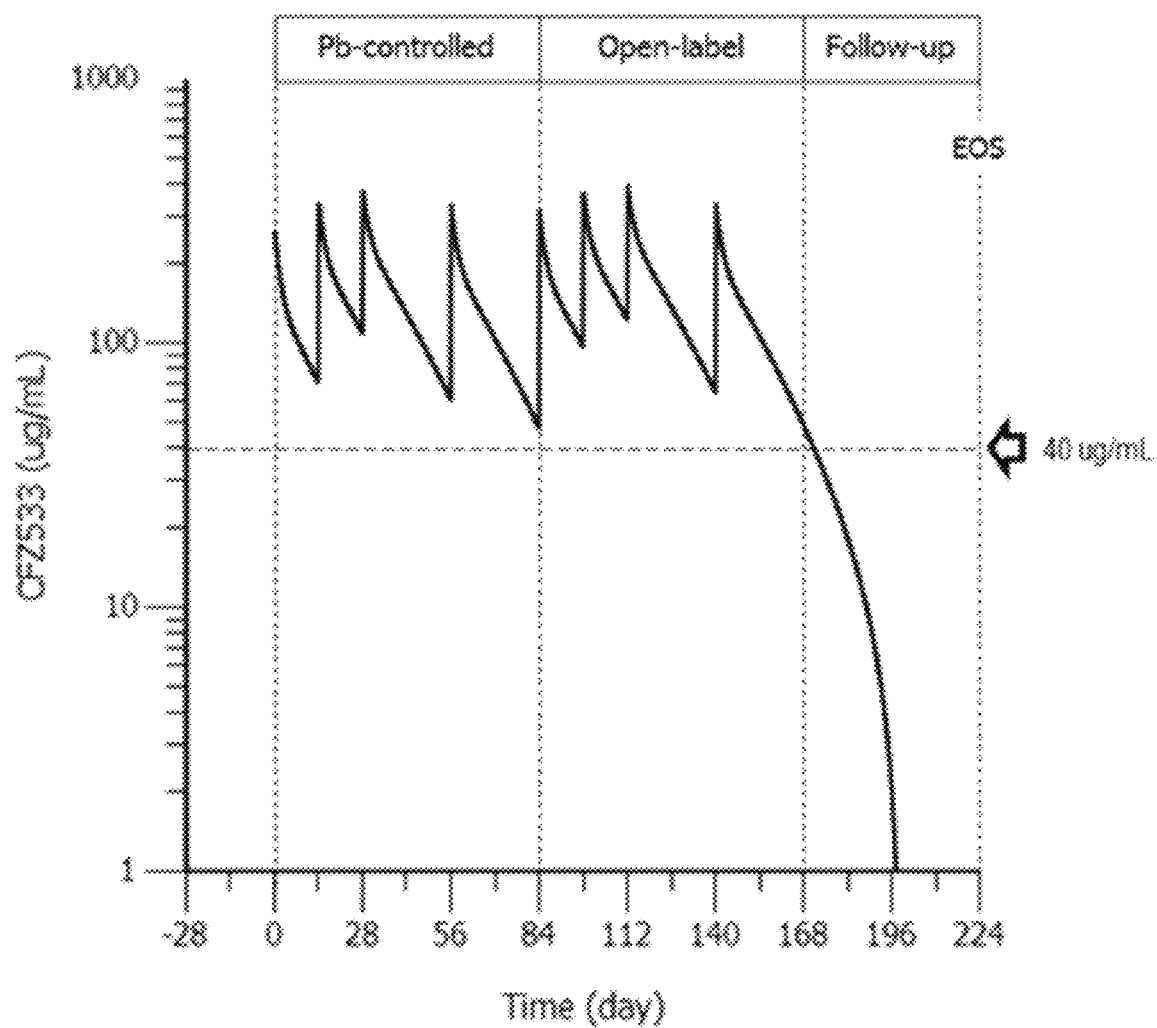
FIG. 3 is a graph showing preliminary simulated pharmacokinetics profiles before the proof of concept study CCFZ533X2203 started.

Adequate Safety Margin from Preclinical Toxicological Studies:

GLP toxicology studies to date have tested CFZ533 at (i) weekly s.c. dosing for 13 weeks at 10, 50, and 150 mg/kg (s.c. and i.v.) in rhesus monkeys, and (ii) weekly s.c. dosing for 26 weeks at 1, 50, and 150 mg/kg in cynomolgus monkeys. These studies did not reveal any major finding that would prevent the use of CFZ533 at the proposed intravenous regimen for 12 weeks or 24 weeks. In the 26-week toxicity study in cynomolgus monkey, at steady state, an average concentration of 8300 µg/mL (Cav,ss) was obtained after weekly dosing at 150 mg/kg (NOAEL). The corresponding systemic exposure (AUC, steady state conditions) over a 1-month period would be 232400 day*µg/mL, which is about 57-fold higher than the predicted systemic plasma exposure over the first month (AUC0-28 days; FIG. 3). In the 26-week toxicology study, at NOAEL, Cmax,ss was 9495 µg/mL, which is 24-fold higher than the expected $C_{max}$ (about 400 µg/mL) for the proposed intravenous regimen in pSS patients (FIG. 3).

FIG. 3 shows predicted mean plasma concentration-time profile for CFZ533 given intravenously at 10 mg/kg (Cohort 2). Mean PK profiles were simulated for 10 mg/kg i.v. CFZ533 given at Study Day 1, 15, 29 and 57 (placebo controlled period), and Study Day 85, 99, 113 and 141 (open-label period). A Michaelis-Menten model was applied using parameters obtained from a preliminary model-based population analysis of Cohort 5 (3 mg/kg i.v.) PK data from FIH study CCFZ533X2101 in healthy subjects. No previous experience with an anti-CD40 blocking agent existed in human pSS, and any potential differences in the biology of CD40 (expression, turnover) between healthy subjects and pSS patients was no known. The proposed i.v. regimen was expected to provide, throughout the entire treatment period, sustained plasma concentrations above 40 μg/mL, to anticipate for an increased CD40 expression in target tissues in pSS patients. The horizontal dotted line at 40 μg/mL is representing plasma concentration above which it is expected full CD40 occupancy and pathway blockade in target tissues (based on PD data from 26-week toxicology study in cynomolgus monkey—dose group 1 mg/kg). The expected systemic exposure for the first month (higher dosing frequency) is 4087 day*μg/mL (57-fold lower than the observed systemic plasma exposure over one month at steady state in the 26-week toxicology study in cynomolgus—NOAEL at 150 mg/kg weekly), the expected $C_{max}$ is about 400 μg/mL.

Relevant PD Effects in Tissues in Non-Human Primates:

In the 26-week toxicological study (1 mg/kg dose group) animals with average steady state plasma concentrations ≥38 μg/mL had a complete suppression of germinal centers in cortical B cell areas of lymph nodes. The 10 mg/kg i.v. regimen was expected to provide, throughout the entire treatment period (placebo-controlled and open-label, see FIG. 3), sustained plasma concentrations above 40 μg/mL, to anticipate for higher CD40 expression in pSS patients, and incomplete PD effects in target tissue due to loss of target saturation.

Data from ASKP1240, a Monoclonal Antibody Blocking CD40:

A recent analysis of disclosed PK/efficacy data from Astellas' anti-CD40 antibody ASKP1240 in solid organ transplantation (Harland et al 2015) demonstrated that efficient target mediated antibody clearance in tissue, could result in loss of CD40 blockade and likely loss of efficacy, as a consequence of a significant increase of target expression in target tissues. The proposed intravenous regimen is aiming to saturate, throughout the entire treatment period, CD40 elimination pathways, in conditions where higher CD40 expression is likely. In house data suggest overexpression of CD40 in tissues obtained from patients with primary Sjögren's syndrome (data on file), and the original subcutaneous regimen may not provide complete and sustained CD40 pathway blockade in target tissues, in these conditions.

Cohort 3

Based on results from Cohorts 1 and 2, an efficient dosing regimen in patients with pSS was thought to require a loading regimen (i.v. or s.c.), providing early full CD40 saturation and minimal target mediated disposition (TMDD) followed by a s.c. maintenance regimen.

In Cohort 3, the dose/regimen in treatment arm 1 and in treatment arm 2 are set to assess whether a loading regimen (i.v. or s.c.), followed by a s.c. maintenance regimen is able to deliver steady state plasma concentrations similar to the i.v. regimen tested in Cohort 2, and had the ability to overcome target mediated disposition of CFZ533 via the s.c. route.

Treatment Arm 1:

CFZ533 is given at 600 mg s.c. (4 injections of 1 mL) weekly on 4 occasions (loading), followed by 300 mg s.c. (2 injections of 1 mL) weekly on 9 occasions (maintenance; starting on study Day 29). During the loading phase, the rate of saturation of the CD40 pool as well as the bioavailability of the s.c. doses, are unknowns. Nevertheless, it is expected that a cumulative dose of 2700 mg over the 1st month (up to Day 29) had the ability to overcome TMDD (the cumulative dose was 630 and 2100 mg at Day 29 in Cohort 1 and Cohort 2, respectively). The 600 mg weekly loading regimen followed by a maintenance regimen of 300 mg weekly is expected to deliver steady state conditions by Day 85, because when target saturation would be achieved, the bioavailability of the subcutaneous doses are expected to be ≥75%, as for healthy volunteers. In treatment arm 1, the cumulative dose up to Day 85 (last dose) would be 5100 mg, as compared to 1050 and 3500 mg, in Cohort 1 and Cohort 2, respectively).

Treatment Arm 2:

the loading regimen consists of a single i.v. dose of 10 mg/kg CFZ533 (on study day 1), followed by 300 mg s.c. weekly on 12 occasions (maintenance regimen starting on study day 8). In Cohort 3 treatment arm 2, as already demonstrated in Cohort 2 i.v., a single i.v. dose of 10 mg/kg (Day 1) is expected to provide plasma concentrations ≥100 μg/mL by study Day 8 (start of the maintenance regimen) and full CD40 saturation conditions. In treatment arm 2 the weekly s.c. maintenance regimen is assessed in the absence of a significant target mediated disposition and first-pass effect (s.c. route).

In Cohort 3, all subcutaneous administrations (300 mg or 600 mg weekly) are given as flat doses (not adjusted to body weight) to facilitate administration and improve convenience, as each vial of the drug product is presented with 150 mg/mL CFZ533.

In Cohort 1 (3 mg/kg s.c. regimen), at interim analysis, the mean bodyweight is 70.7 kg (range 50.0-91.1 kg), corresponding to 212.2 mg flat dose (range 150-273.3 mg). In Cohort 2 (10 mg/kg i.v. regimen), the mean bodyweight is 72.6 kg (range 50.0-107.2 kg), corresponding to 726 mg flat dose (range 500-1072 mg). In Cohort 3, the subcutaneous doses of 300 mg or 600 mg on each occasion, are within the range of doses already applied in Cohort 1 and 2, and are unlikely to have an impact on safety and tolerability. The way bodyweight influences the disposition of CFZ533 is not fully characterized, but for both arms, throughout the entire treatment period it is expected that the mean maximum plasma concentration ($C_{max}$) will be below ca. 300 μg/mL (assuming all subcutaneous doses are 100% bioavailable for sake of safety, and a mean bodyweight of 70 kg for pSS patients), and is not expected to exceed the mean $C_{max}$ observed in Cohort 2 (about 386 μg/mL, fifth dose on Day 85 of the Cohort 2 placebo-controlled Period 1). This would be 32-fold lower than $C_{max}$ values (mean of 9495 μg/mL) in the 26-week toxicology study in cynomolgus monkey, at NOAEL (150 mg/kg s.c. weekly).

PK/PD and immunogenicity endpoints are being assessed during the treatment and follow-up periods. Table 2 provides a protocol synopsis for the study.

TABLE 2

Protocol synopsis

| | |
|---|---|
| Purpose and rationale | This study is designed to evaluate the safety, tolerability, pharmacokinetics, pharmacodynamics, and preliminary therapeutic efficacy of multiple doses of CFZ533 monoclonal antibody in patients with primary Sjögren's syndrome (pSS), |

TABLE 2-continued

Protocol synopsis

| | |
|---|---|
| Primary Objectives | To assess the safety and tolerability of multiple intravenous infusions of CFZ533 in patients with primary Sjögren's syndrome as measured by adverse events (AEs). To compare the effect of multiple intravenous infusions of CFZ533 versus placebo on the clinical disease activity of primary Sjögren's syndrome patients as measured by the |
| Secondary Objectives | To assess the safety and tolerability of multiple subcutaneous doses of CFZ533 in patients with primary Sjögren's syndrome as measured by adverse events (AEs). To compare the effect of multiple subcutaneous doses of CFZ533 versus placebo on the clinical disease activity of primary Sjögren's syndrome patients as measured by the change of the EULAR Sjögren's Syndrome Disease Activity Index (ESSDAI) after 12 weeks treatment. To assess the pharmacokinetics of multiple subcutaneous doses and multiple intravenous infusions of CFZ533 in primary Sjögren's syndrome patients. To evaluate the effect of multiple subcutaneous doses and multiple intravenous infusions of CFZ533 versus placebo on self-reported outcomes in primary Sjögren's syndrome patients after 12 weeks treatment as measured by the EULAR Sjögren's Syndrome Patient Reported Intensity (ESSPRI), the Short Form (36) Health Survey (SF-36) and the |
| Study design | Randomized, double-blind, placebo-controlled, non-confirmatory study in approximately 12 patients in Cohort 1 and 30 patients in Cohort 2, and open- label randomized study in approximately 24 |
| Population | Male and female patients with primary Sjögren's syndrome, age 18 to 75 years (inclusive). |
| Inclusion criteria | Diagnosis of primary Sjögren's syndrome according to revised EU/US consensus criteria (Vitali et al 2002) Moderate to severe disease activity with ESSDAI score ≥6 Presence of autoantibodies at screening as determined by any of the following: Elevated serum titers of ANA (≥1:160) and positive rheumatoid factor (RF), or, Positive anti-SSA Stimulated whole salivary flow rate >0 mL/min for Cohort 1 and 2; and unstimulated whole salivary flow rate >0 mL/min for Cohort 3. If the patient is on oral glucocorticoid treatment at screening, the dose must NOT exceed 10 mg prednisone or equivalent per day, and must be stable for at least 2 weeks prior to randomization and for the duration of the study; If the patient is on chloroquine or hydroxychloroquine at screening, the dose must be stable for at least 4 weeks prior |
| Exclusion criteria | Secondary Sjögren's syndrome Use other investigational drugs at the time of enrollment, or is within five half-lives of using other investigational drugs or longer if required by local regulations, at the time of enrollment History of hypersensitivity to study drug or to drugs of similar chemical classes Patients have received treatment with: Cyclosphosphamide within 6 months; Corticosteroid bolus i.v. dose >1 mg/kg within 3 months Rituximab within 12 months Belimumab within 6 months; Any other biologic within 1 month or five times the half-life Any other immunosuppressives such as cyclosporine A or mycophenolate within 3 months Patients where the primary cause of sicca symptoms is attributable to a medication used regularly or intermittently rather than to primary Sjögren's syndrome At significant risk for thromboembolic events |
| Investigational and reference therapy | Cohort 1: CFZ533 150 mg Powder for Solution for injection and matching placebo CFZ533: 3 mg/kg administered subcutaneously. Control: CFZ533 placebo Cohort 2: CFZ533 150 mg Powder for Solution for injection and matching placebo CFZ533: 10 mg/kg administered by intravenous infusion. Control: CFZ533 placebo Cohort 3: CFZ533 150 mg Liquid in Vial for injection |

TABLE 2-continued

| Protocol synopsis | |
|---|---|
| Efficacy and pharmacodynamic assessments | EULAR Sjögren's Syndrome Disease Activity Index (ESSDAI) Total soluble CD40 in plasma, total soluble CD154 in plasma, CD40 occupancy on peripheral bold B cells |
| Safety assessments | All Cohorts: Physical examination Vital signs Laboratory evaluations: hematology, clinical chemistry, urinalysis Electrocardiogram (ECG) Pregnancy testing Adverse event Serious adverse event Immunogenicity (anti-CFZ533 antibodies) |
| Other assessments | All Cohorts: Pharmacokinetics of CFZ533 Soluble biomarkers (e.g., CXCL13) EULAR Sjögren's Syndrome Patient Reported Intensity (ESSPRI) Physician's and Patient's assessment of global disease activity (VAS) Cohorts 1 and 2: |
| Data analysis | Cohorts 1 and 2: A longitudinal model describing ESSDAI change from baseline over time will be fitted for the controlled part of the study (up to Week 13) with the following covariates: baseline ESSDAI, baseline prednisone dose, treatment (placebo, CFZ533 3 mg/kg s.c. or CFZ533 10 mg/kg i.v), time as a continuous factor and a quadratic time effect, as well as a random intercept, a random slope and a random quadratic effect for subject. The change from baseline in ESSDAI at Week 13 will be estimated from the model for all treatments. Inference will be made in the frequentist framework. The results from the primary analysis will be assessed against the following efficacy criteria to support internal decision making: a statistically significant reduction in ESSDAI at Week 13 in the CFZ533 group compared to placebo, at the one-sided 10% significance level, and, an estimated mean reduction in ESSDAI in the CFZ533 |

4. Results
Cohort 1&2

Forty-four patients were enrolled: 8 patients received 3 mg/kg s.c. CFZ533 and 4 placebo in Cohort 1 and 21 received 10 mg/kg i.v. CFZ533 and 11 placebo in Cohort 2. While PK/PD was as expected in the CFZ533 10 mg/kg i.v. cohort based on data from the first in human trial, CFZ533 exposure appeared lower than expected in the 3 mg/kg s.c. cohort, likely due to efficient target mediated disposition (first pass effect) in conditions were CD40 expression is likely to have been enhanced. Overall, CFZ533 was safe and well tolerated, and the majority of AEs were mild or moderate. There was a single serious AE (bacterial conjunctivitis) in the 3 mg/kg s.c. cohort that was not related to study drug. In Cohort 1, ESSDAI was observed to improve by approximately 2 points from mean baseline scores of approximately 12 in both placebo and 3 mg/kg s.c. groups, with therefore no evidence of treatment difference (AESSDAI=0.68, 95% CI=-4.71-6.46). However in Cohort 2, the improvement in ESSDAI from mean baselines of approximately 11 was observed to be 6.35 in the 10 mg/kg i.v. group compared to 1.27 in the placebo group, with the modelled difference between groups of AESSDAI=5.2 (95% CI=1.02-10.58) strongly favoring the CFZ533 i.v. treatment. Improvements in other measures such as ESSPRI, MFI, Physician's Global Assessment, and Patient's Global Assessment and decreases in the germinal center-related serum biomarker CXCL13 were also observed in the 10 mg/kg i.v. CFZ533 group.

Figure 4:
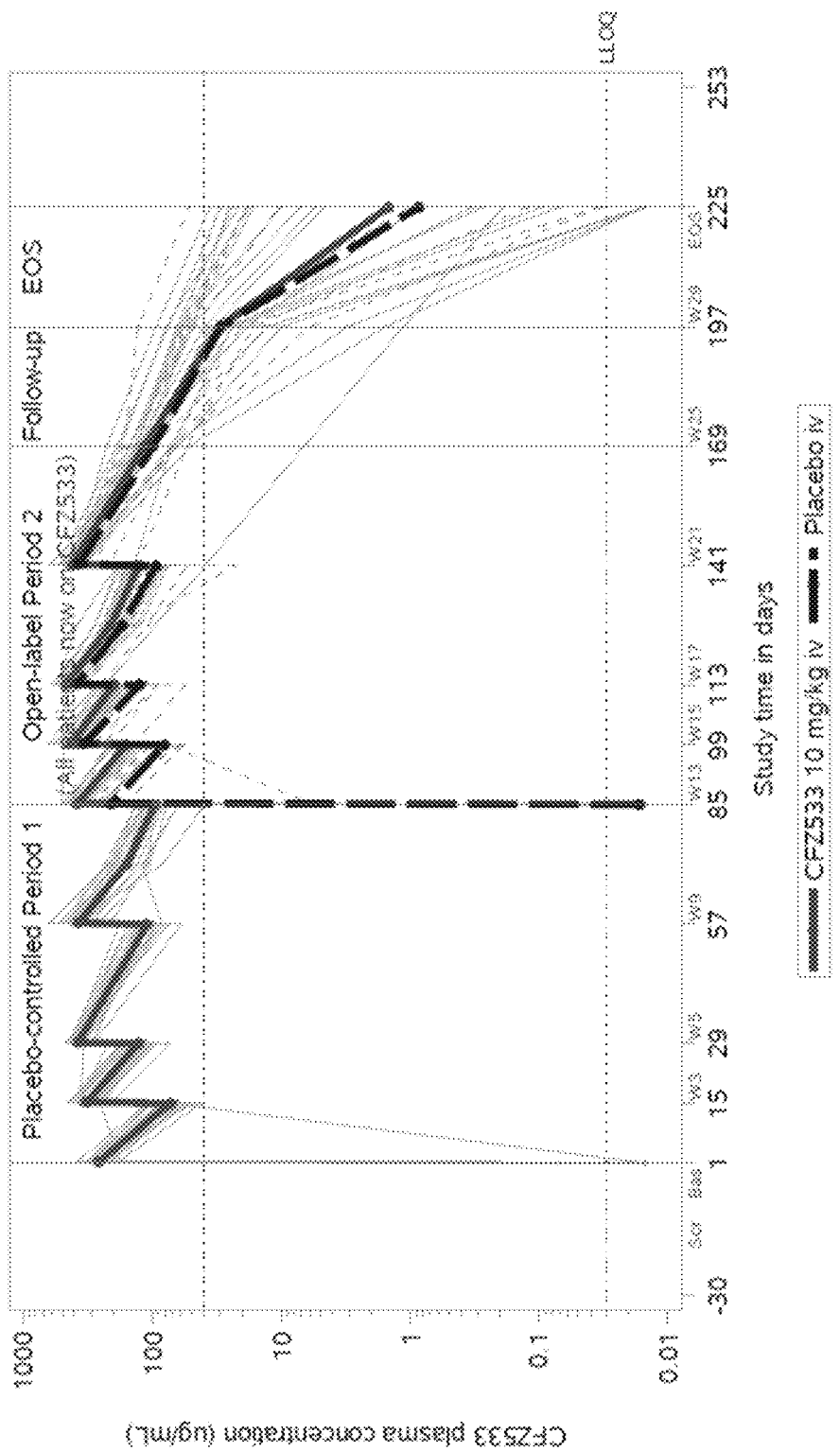
FIG. 4 is a graph showing pharmacokinetic profiles after intravenous administration (Cohort 2 of Study CCFZ533X2203; interim analysis).

FIG. 4 is a graph showing pharmacokinetics of CFZ533—10 mg/kg IV. IV regimen provided full target saturation and complete CD40 pathway blockade in target tissues. CD40 pathway blockade in tissue expected with plasma concentration >40 µg/mL (suppression of GC development and T dependent antigen response), dotted line in the graph. After 12/24 weeks of treatment, emerging signs that CD40 expression was down-modulated in some pSS patients.

Figure 5:
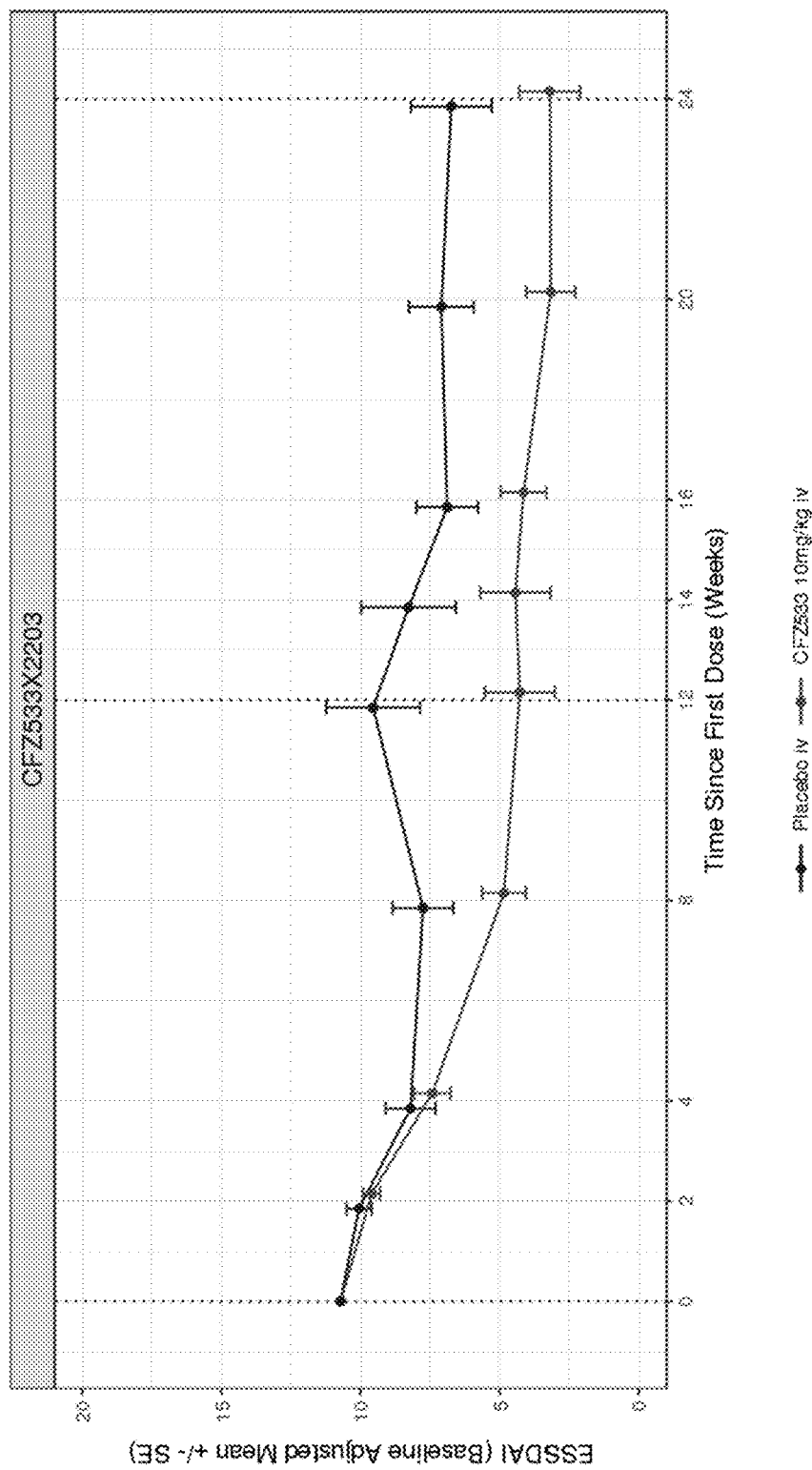
FIG. 5 is a graph showing clinical scores (ESSDAI) after IV administration (Cohort 2; Study CCFZ533X2203).

FIG. 5 shows the baseline adjusted ESSDAI total score—10 mg/kg IV. The upper line is Placebo iv and the lower line is CFZ533 10 mg/kg iv. As can be seen, there was a clear improvement (mean delta=5.6 by week 12) in CFZ533 group vs placebo.

Figure 6:
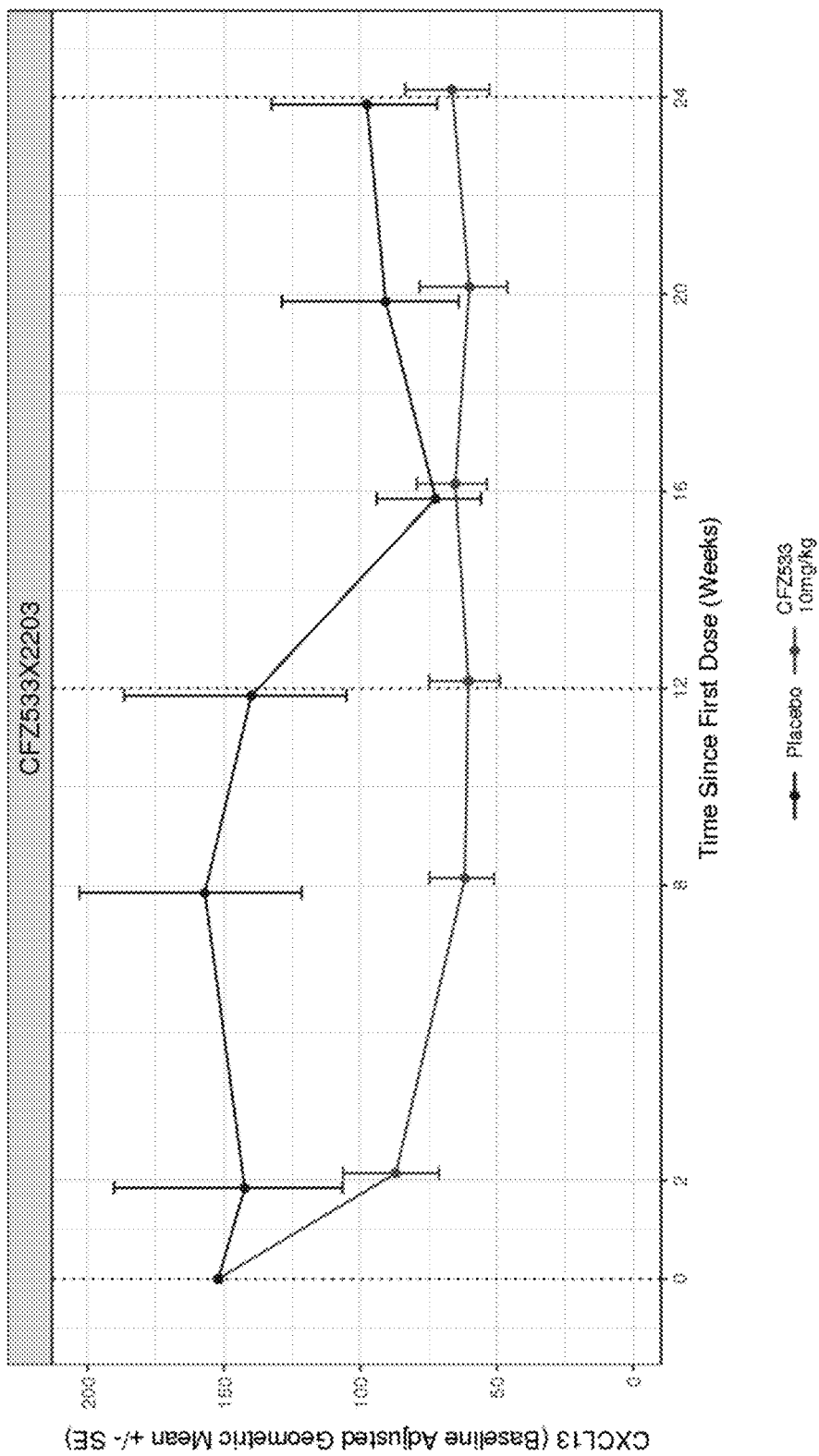
FIG. 6 is a graph showing biomarker levels (CXCL13) after IV administration (Cohort 2; Study CCFZ533X2203).

FIG. 6 shows the baseline adjusted CXCL13—10 mg/kg IV. The upper line is placebo iv and the lower line is CFZ533 10 mg/kg iv.

Figure 7:
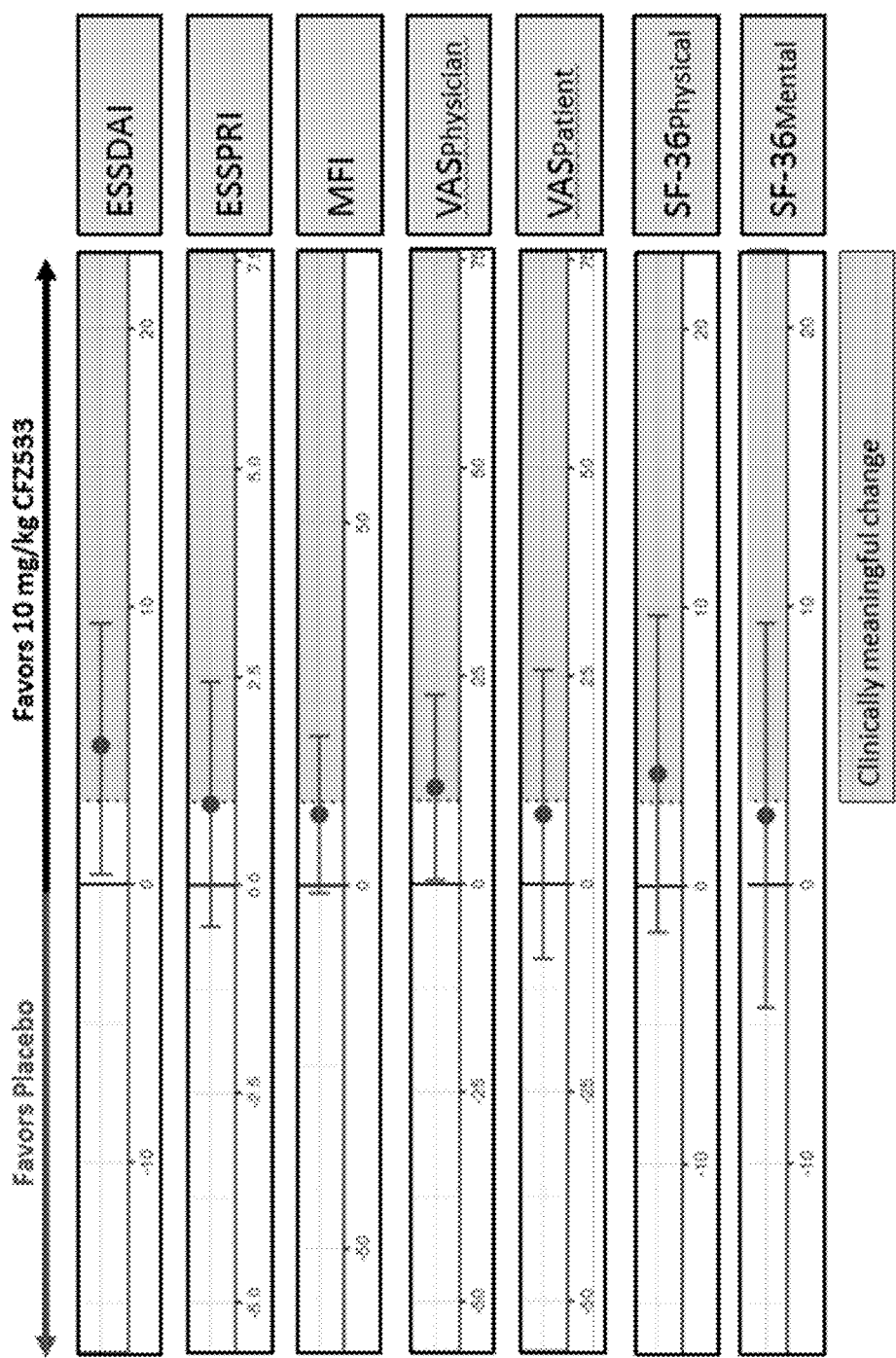
FIG. 7 is a schematic representation showing treatment results for different clinical endpoints after IV administration (Cohort 2; Study CCFZ533X2203).

FIG. 7 shows treatment group difference in various endpoints for 10 mg/kg CFZ533 vs placebo at Week 13 (after 12 weeks of treatment—Period 1).

It can be concluded that there are clear improvements in ESSDAI and Physician's Global assessment (VAS). Also, trends in most secondary endpoints favor CFZ533. ESSDAI changes were sustained in the open label period. Some improvement in Placebo group when switched to 10 mg/kg IV CFZ533 with significant decreases in CXCL13 levels following the same pattern.

In this proof of concept study, testing a blocking, non-depleting anti-CD40 antibody for the first time in primary Sjögren's syndrome, results suggest that CFZ533 may offer a new treatment modality in clinically active pSS.

Figure 8:
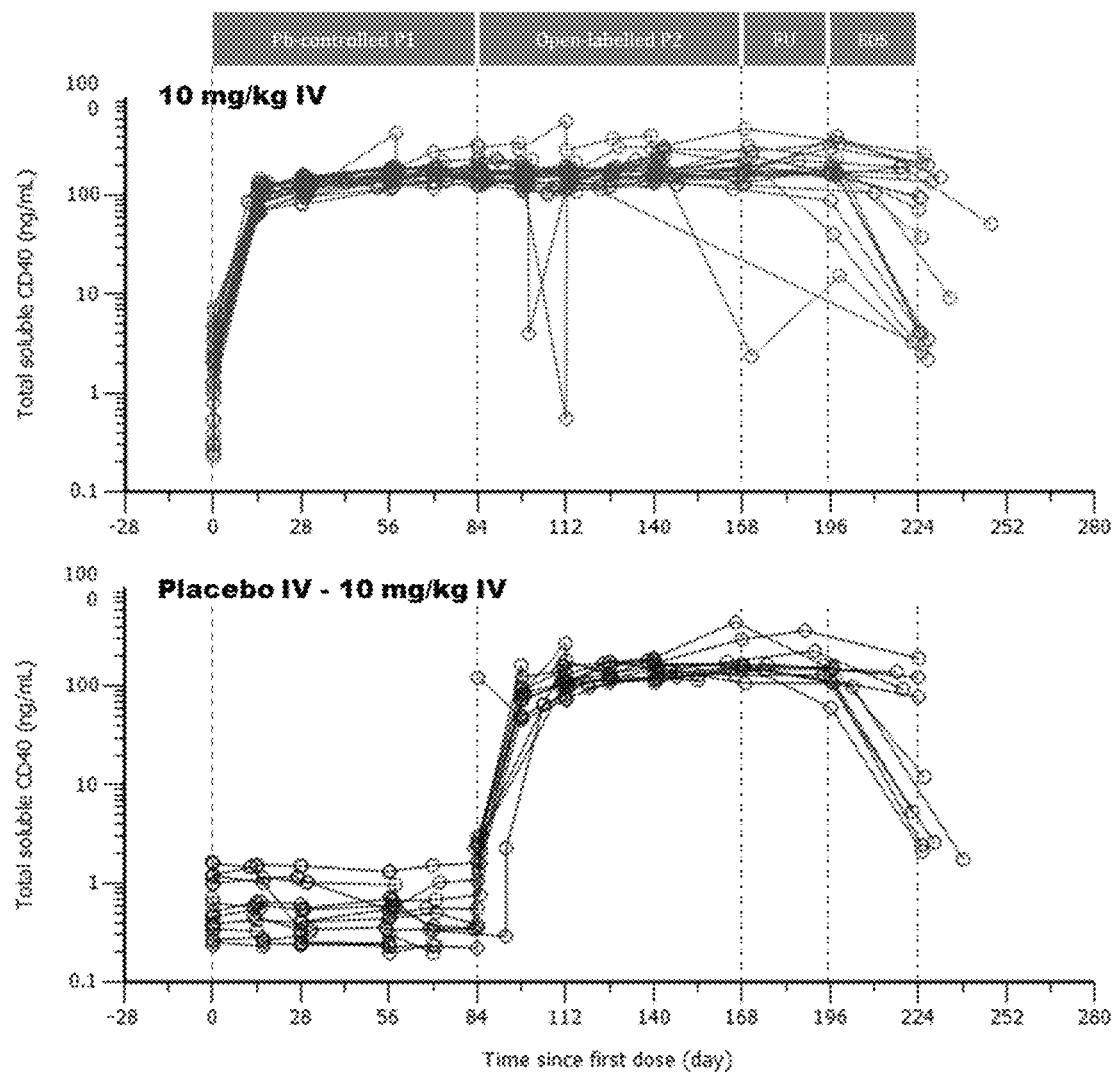
FIG. 8 is a graph showing pharmacodynamic profiles (total soluble CD40 in plasma after IV administration; Cohort 2; Study CCFZ533X2203).

In addition, FIG. 8 shows pharmacodynamics/target engagement (10 mg/kg IV). In total soluble CD40 in plasma—Sustained target engagement during treatment and follow-up period. After 12/24 weeks of treatment, there are emerging signs that CD40 expression was down-modulated in some pSS patients.

Figure 9:
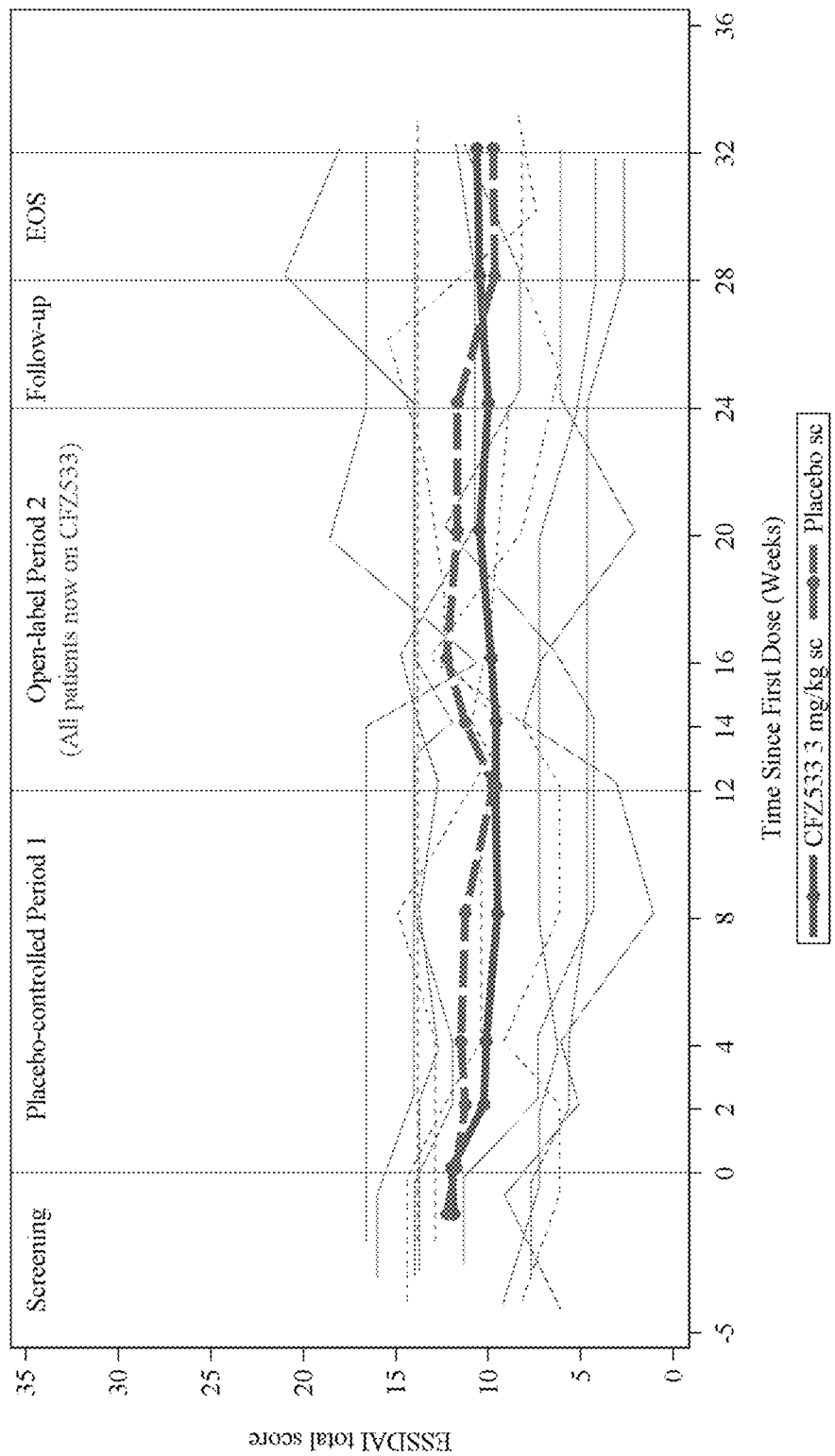
FIG. 9 is a graph showing clinical scores (ESSDAI) after subcutaneous administration (Cohort 1; Study CCFZ533X2203).

FIG. 9 shows profile plot of ESSDAI total score—Cohort 1: 3 mg/kg SC.

Figure 10:
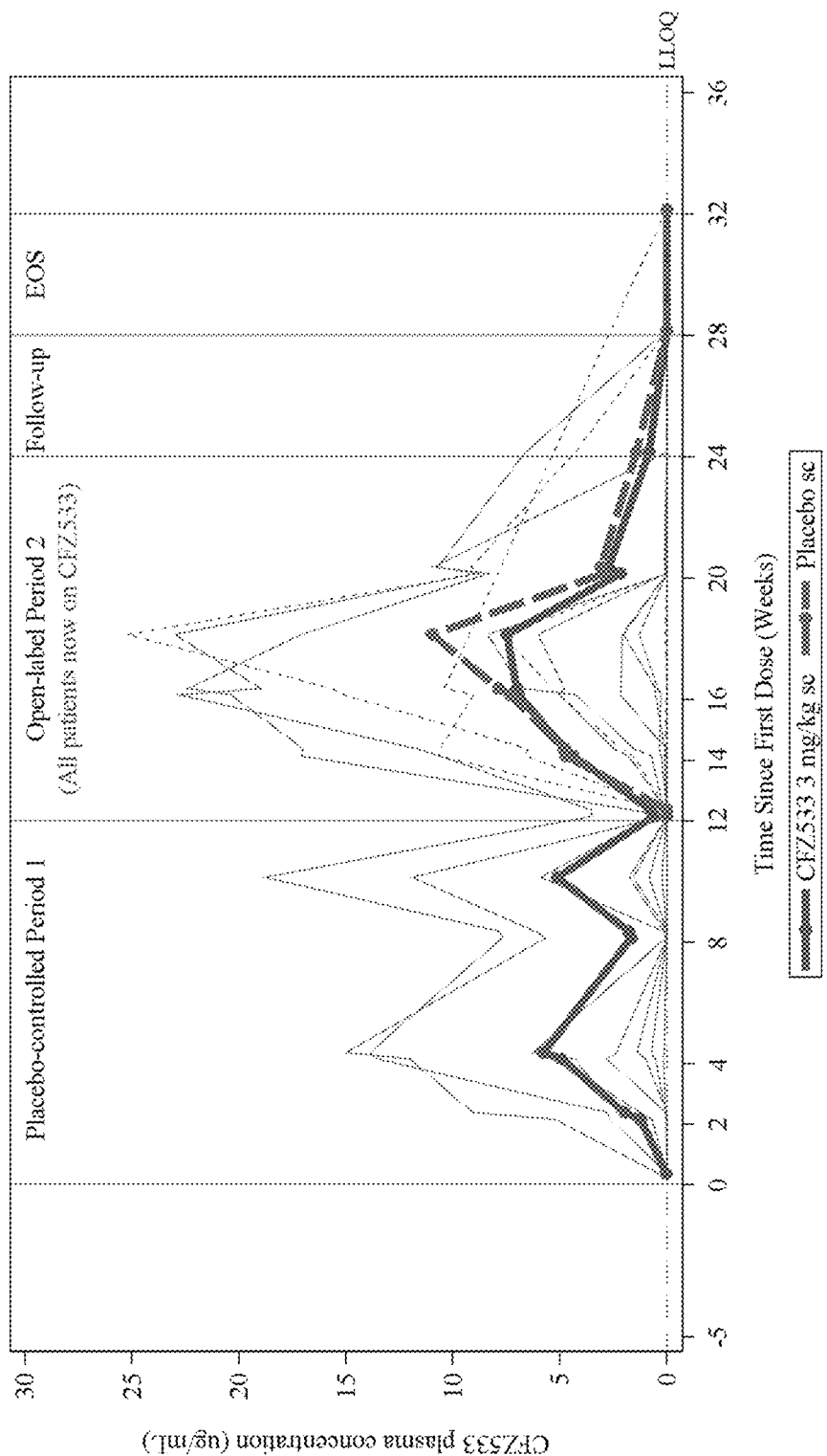
FIG. 10 is a graph showing pharmacokinetic profiles after subcutaneous administration (Cohort 1; Study CCFZ533X2203).

FIG. 10 shows pharmacokinetics: free CFZ533—Cohort 1: 3 mg/kg SC. As can be seen, there is efficient pre-systemic target-mediated clearance (first pass effect; likely due to elevated CD40 expression)—CD40 pathway blockade in tissues not achieved (CFZ533 <40 ug/mL).

Figure 11:
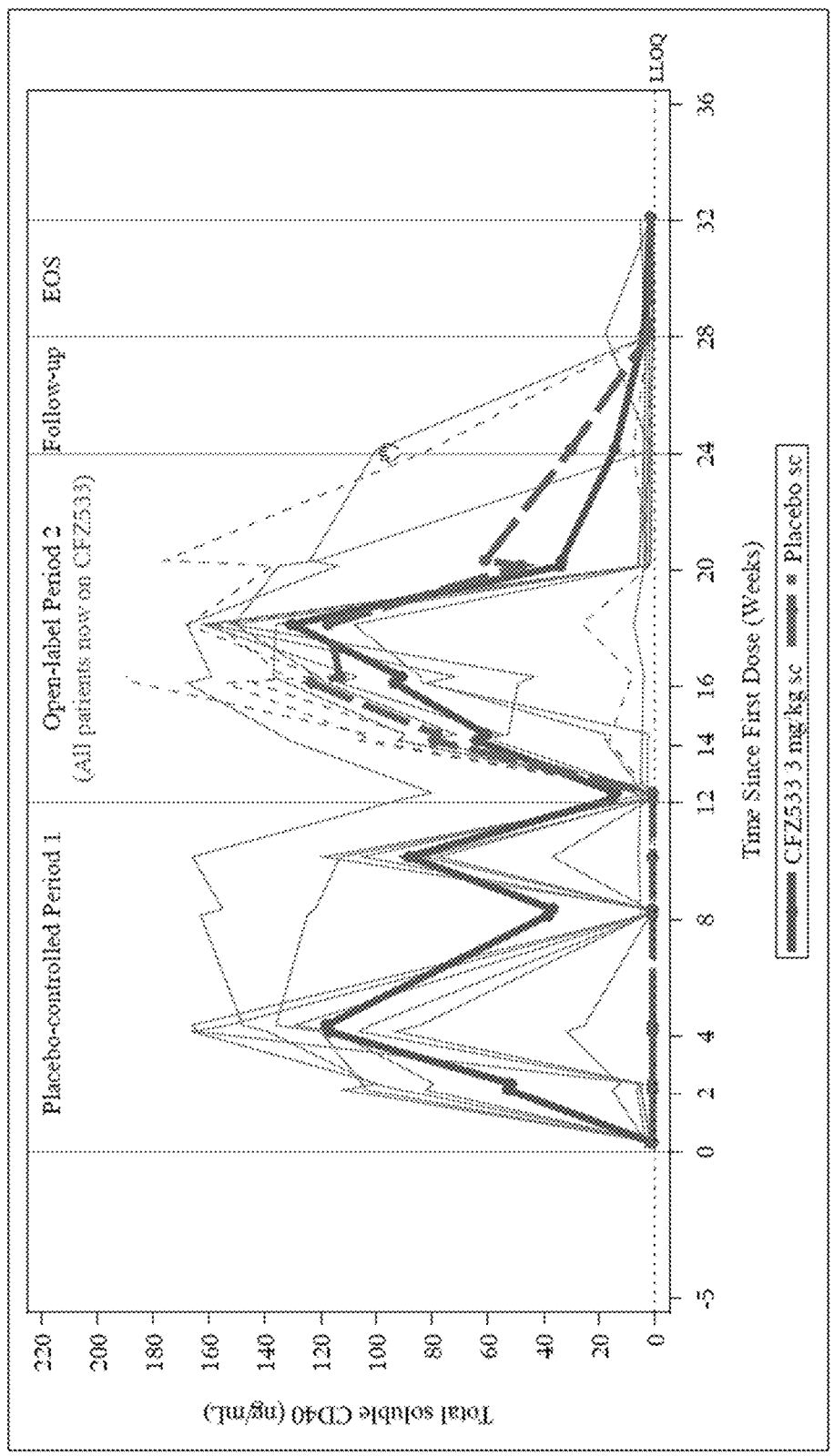
FIG. 11 is a graph showing pharmacodynamic profiles (total soluble CD40) after SC administration (Cohort 1; Study CCFZ533X2203).

FIG. 11 shows pharmacodynamics/target engagement: Total soluble CD40 in plasma—Cohort 1: 3 mg/kg SC. As can be seen, target engagement was not sustained due to target mediated elimination in conditions were CD40 expression was likely enhanced.

Figure 12:
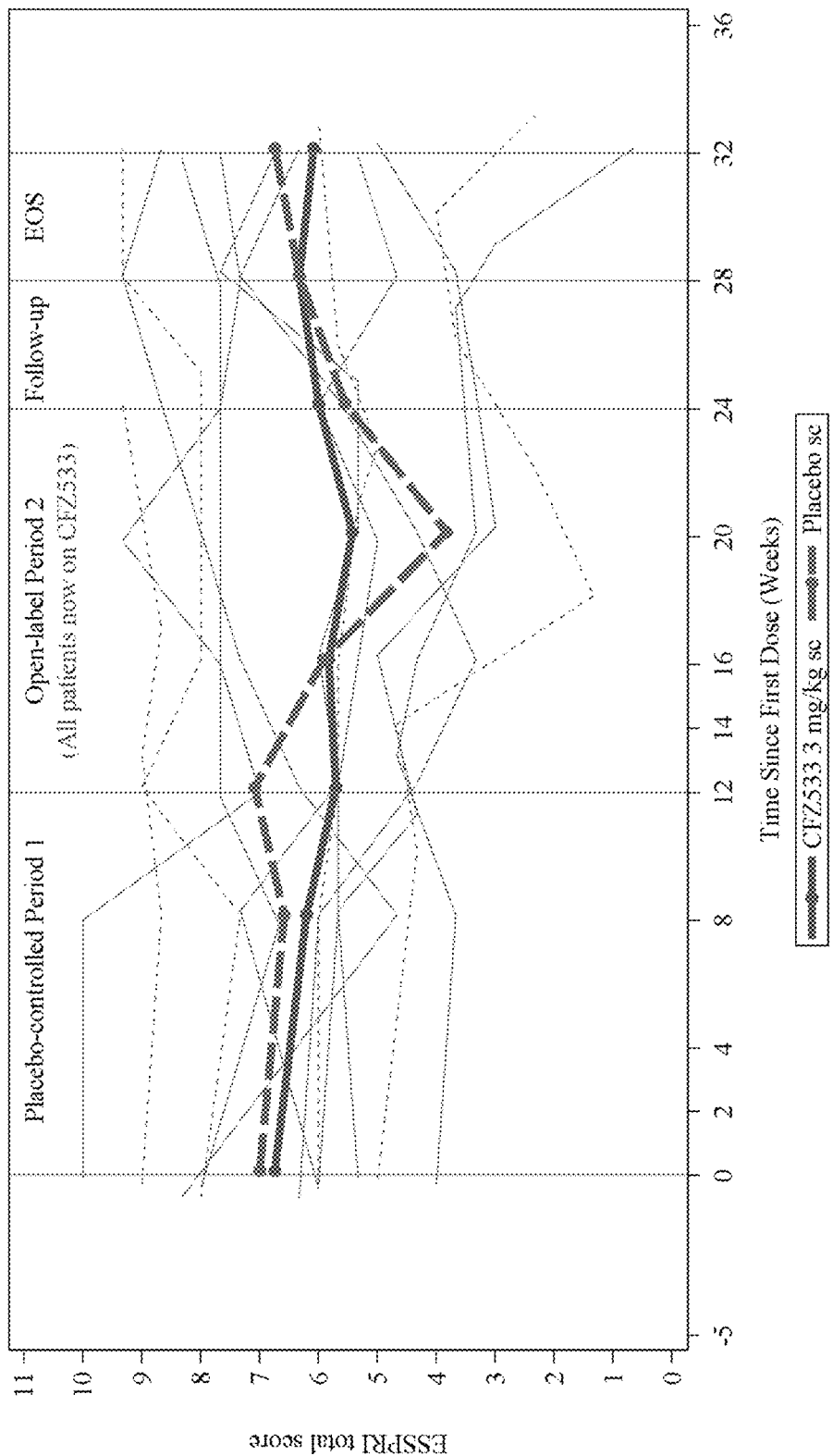
FIG. 12 is a graph showing clinical scores (ESSPRI) after SC administration (Cohort 1; Study CCFZ533X2203).

FIG. 12 shows profile plot of ESSPRI total score—Cohort 1: 3 mg/kg SC.

Figure 13:
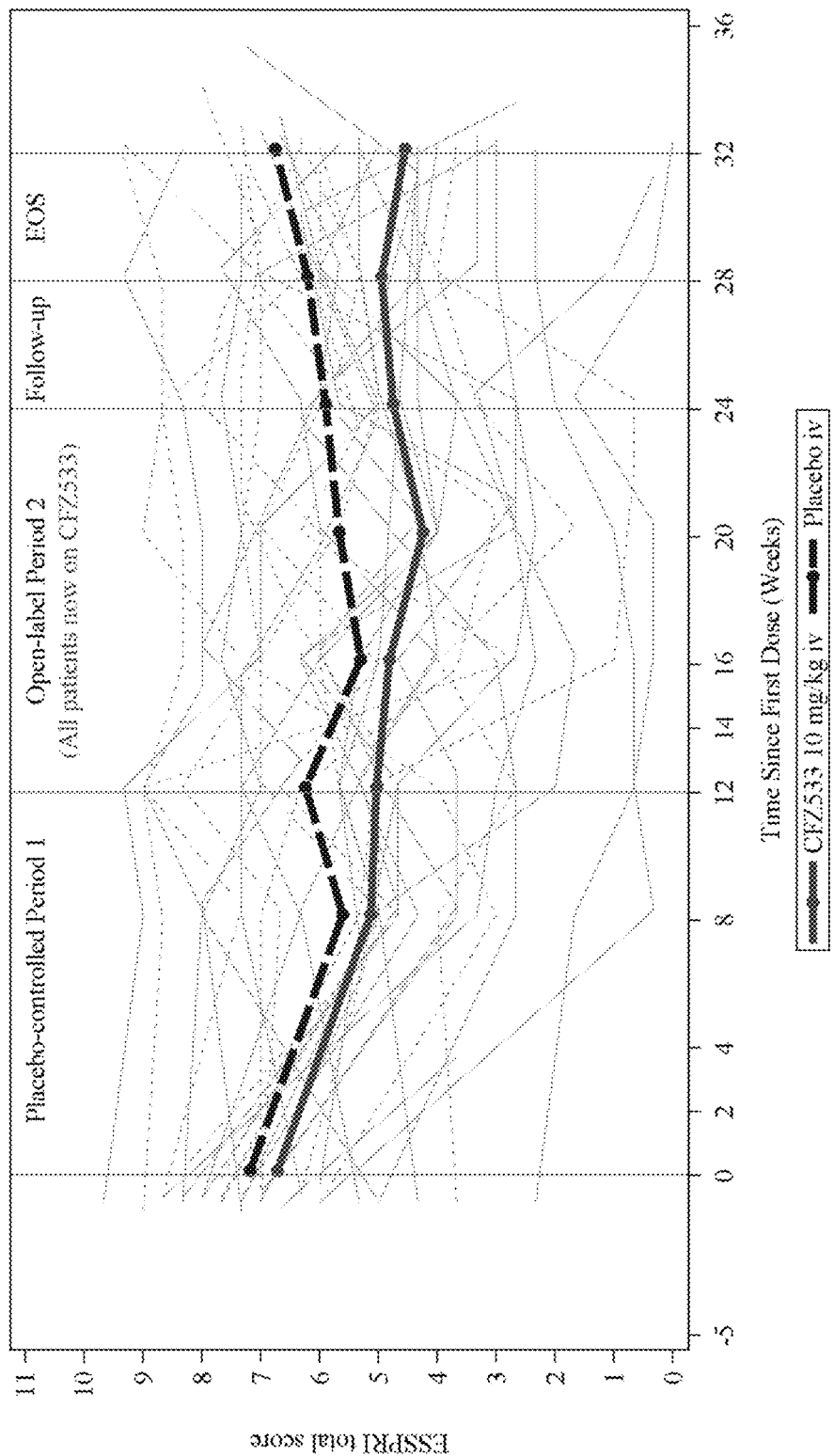
FIG. 13 is a graph showing clinical scores (ESSPRI) after IV administration (Cohort 2; Study CCFZ533X2203).

FIG. 13 shows profile plot of ESSPRI total score—Cohort 2: 10 mg/kg IV.

Figure 14:
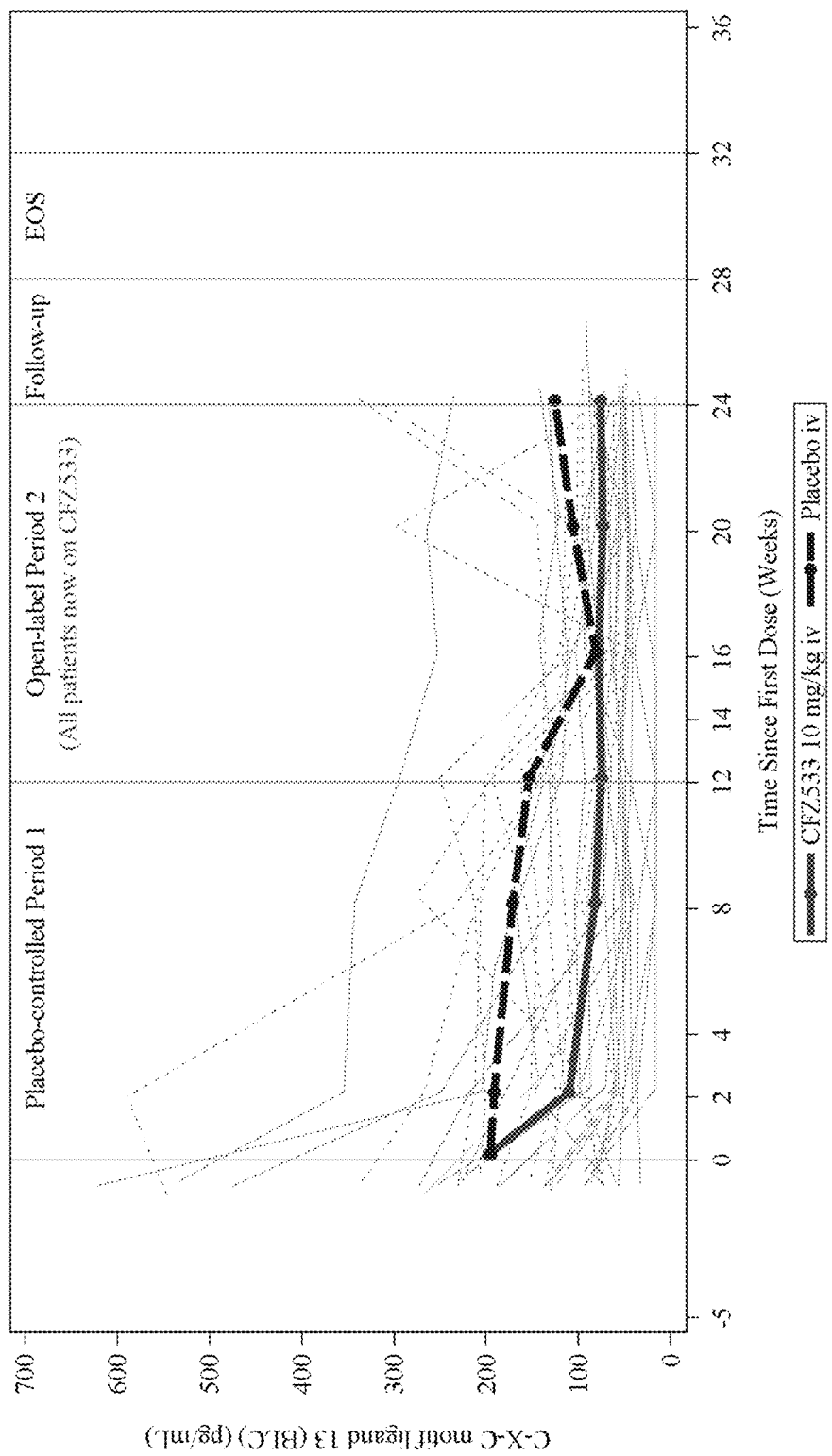
FIG. 14 is a graph showing biomarker levels (CXCL13) after IV administration (Cohort 2; Study CCFZ533X2203).

FIG. 14 shows profile plot of CXCL13 (pg/mL)—Cohort 2: 10 mg/kg IV.

Figure 15:
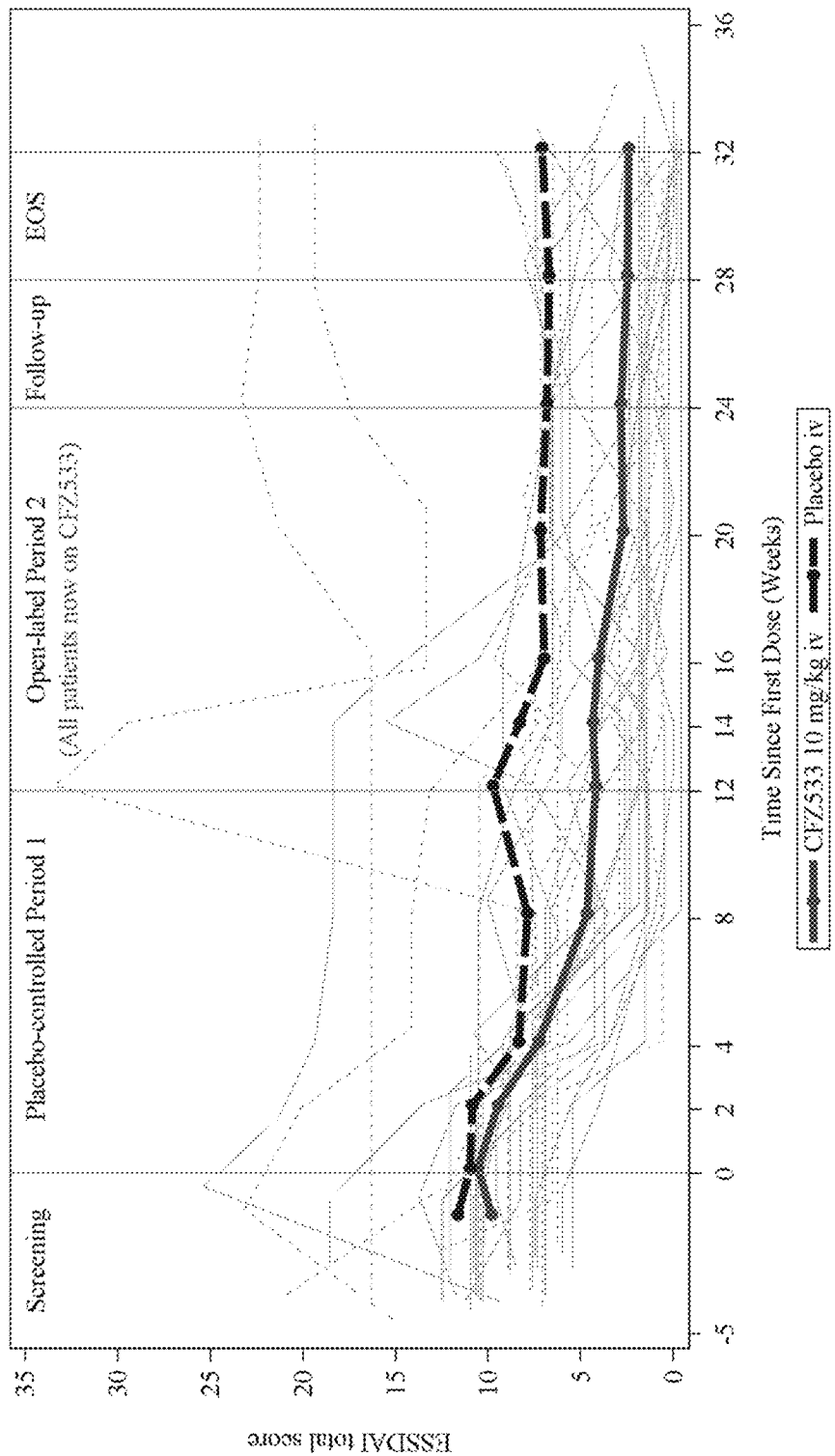
FIG. 15 is a graph showing clinical scores (ESSDAI) after IV administration (Cohort 2; Study CCFZ533X2203).

FIG. 15 shows profile plot of ESSDAI total score in 10 mg/kg CFZ533 cohort.

Figure 16:
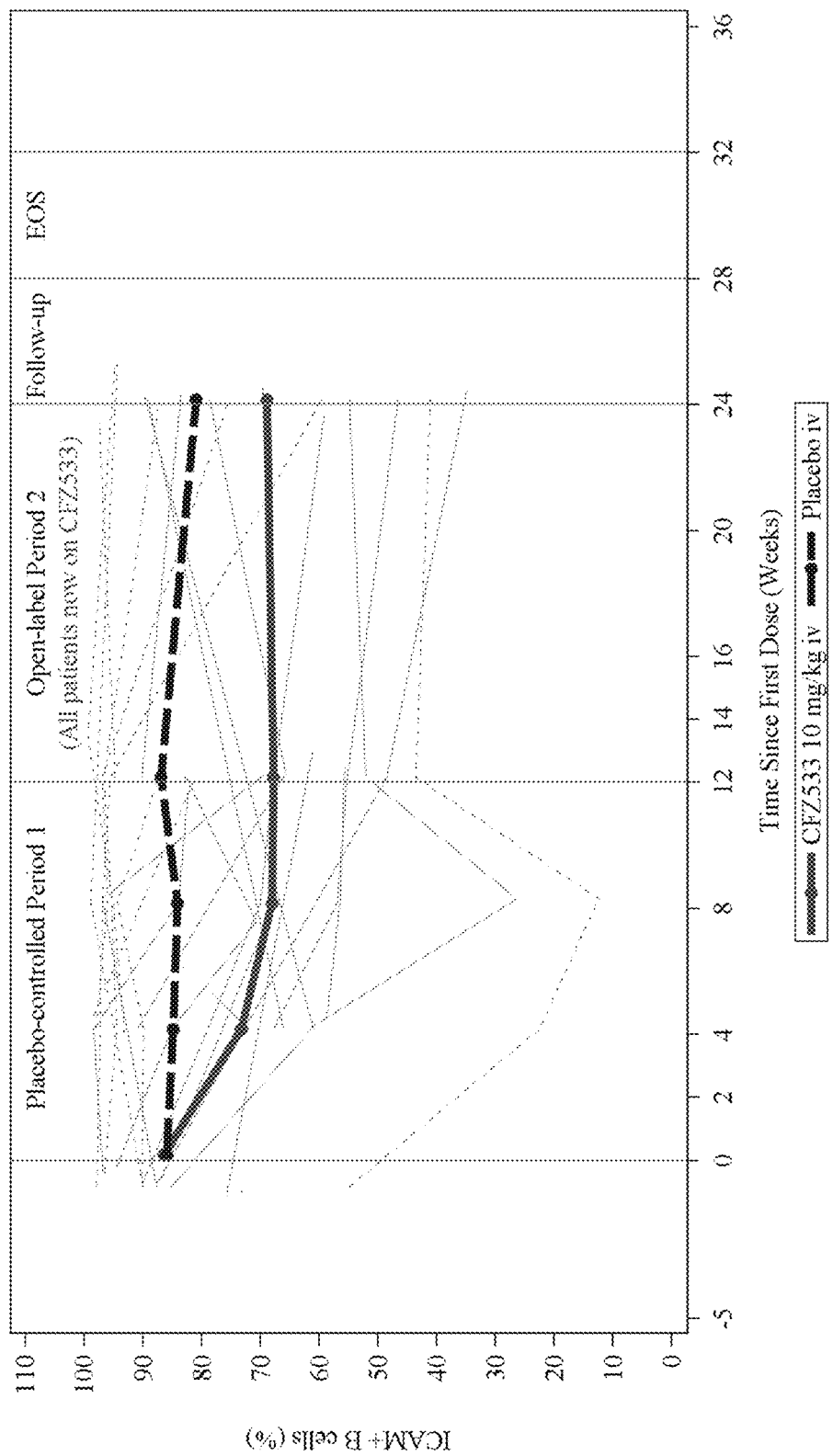
FIG. 16 is a graph showing ICAM and B cell levels after IV administration (Cohort 2; Study CCFZ533X2203).

FIG. 16 shows profile plot of ICAM+ B cells (%)—Cohort 2: 10 mg/kg IV.

Figure 17:
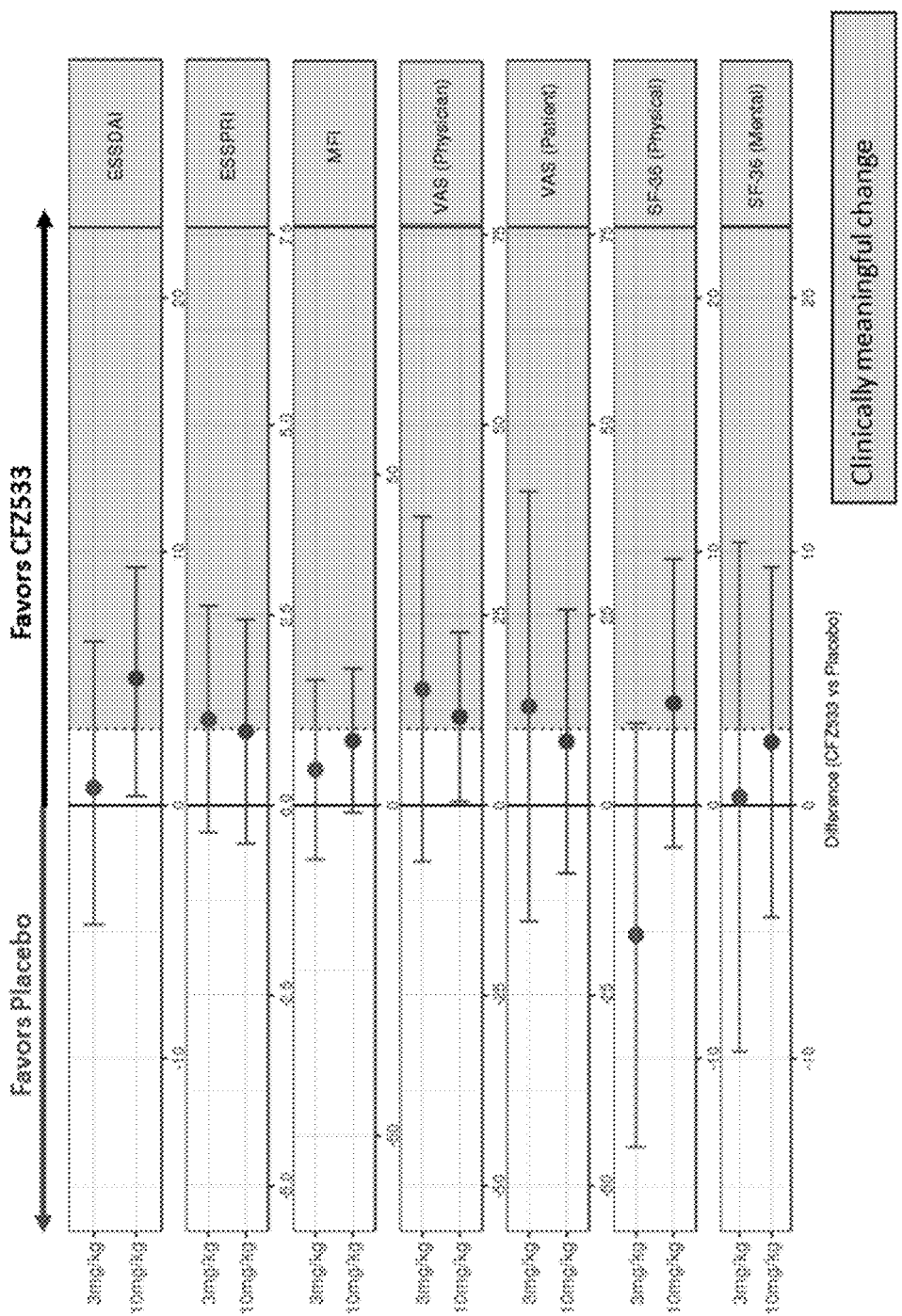
FIG. 17 is a schematic representation showing treatment results for different clinical endpoints (IV and SC administration; Study CCFZ533X2203).

FIG. 17 shows treatment group difference in various endpoints, CFZ533 vs placebo at Week 13 (after 12 weeks of treatment—Period 1).

CD40 signaling has been associated with the pathogenesis of autoimmune diseases (AD), and patients with systemic ADs (including pSS) generally present with increased CD40 expression and elevated serum/plasma sCD40 levels. In salivary glands biopsies from primary Sjögren's syndrome patients, CD40 was constitutively expressed by lymphocytes, ductal epithelial cells and endothelial cells (Dimitriou et al, 2002), which is in line with elevated plasma levels at baseline noted in Study CCFZ533X2203.

CFZ533 is subject to target mediated disposition (TMD), a process in which a significant proportion of CFZ533 (relative to dose) is bound with high affinity to CD40 such that this interaction is reflected in the PK profile of CFZ533. In such circumstances additional factors to consider for defining the appropriate posology to treat pSS patients include CD40 expression level in the body, CD40 synthesis and degradation (the biology of the target), and CFZ533-CD40 binding kinetics.

Previous clinical experience with CFZ533 in healthy volunteers, rheumatoid arthritis, primary Sjögren's Syndrome, kidney transplantation, Grave's disease and myasthenia gravis patients, has shown that elevated CD40 expression is associated with high elimination (clearance) rate of CFZ533, loss of target engagement and loss of CD40 pathway blockade in target tissues, if CD40 is not fully saturated. Under full CD40 occupancy, the contribution of CD40 to the overall clearance of CFZ533 is minimal, and the disposition of CFZ533 is mainly the consequence of CFZ533 binding to FcRn receptors (a high capacity receptor responsible for IgG homeostasis by recycling/salvage.

As can be seen from the data, from a pharmacokinetic/ pharmacodynamic perspective and dose finding strategy, it is likely that an appropriate posology in pSS patients would include a loading regimen followed by maintenance regimen.

The loading regimen, likely during the first month, through IV or SC administration is justified because CFZ533 is subject to CD40 mediated elimination. If CD40 is not fully saturated at start of treatment, in conditions of elevated CD40 expression, a high elimination (clearance) rate of CFZ533 is likely to be associated with loss of target engagement and loss of CD40 pathway blockade in target tissues. After the loading period, and based on preliminary modeling using PK data from the ongoing study CCFZ533X2203 in pSS patients a SC maintenance regimen will be selected to ensure full CD40 pathway blockade in target tissues.

Cohort 3

Decreases in ESSDAI from baseline to week 12 in Cohort 3 showed a similar pattern in both dosing arms as in Cohort 2, thus supporting efficacy of the two IV/SC or SC/SC dosing regimens of CFZ533. However, as Cohort 3 was open label and without placebo control, the efficacy data were only exploratory and should be interpreted with caution.

Example 8. Blockade of CD40-CD154 Pathway Interactions Suppresses Ectopic Germinal Centers and Inhibits Pathology in the NOD/ShiLtJ Mouse Model of Sjögren's Syndrome Sjögren's syndrome (SS) is a chronic, autoimmune disease characterized by sialadenitis and exocrine gland dysfunction. It is one of the most common rheumatic systemic autoimmune disease after RA with a prevalence adult population is 0.3-0.5%. Clinical manifestations include fatigue, keratoconjunctivitis sicca, xerostomia, dry nose, dry vagina, dry trachea, dry skin, arthralgia/arthritis, Raynaud's, lymphadenopathy, interstitial pneumonitis, vasculitis (usually cutaneous), nephritis, and lymphoma.

EULAR Sjögren's syndrome disease activity index (ESSDAI) was designed to measure disease activity in patients with primary SS. ESSDAI is an HA accepted primary outcome measure for SS and designed as complementary to patient reported outcomes (ESSPRI).

Specific manifestations of the disease in both primary and secondary SS patients include the presence of anti-Ro and La autoantibodies as well as mononuclear cell infiltrates in salivary and lacrimal glands (Bombardieri et al., 2012). In some instances, these accumulations of T and B lymphocytes form well-organized structures referred to as ectopic lymphoid structures (ELS) that bear morphological and functional similarities to GCs (Voulgarelis et al., 2008). Previous work has reported evidence of ELS in salivary glands from SS patients and from preclinical models of this disease and evidence of ongoing affinity maturation (Jacobi et al., 2002; Stott et al., 1998; Bombardieri et al., 2012), implicating these structures in disease pathology (Bombardieri et al., 2017).

There is relatively little published data on the role of various immune costimulatory pathways in ELS formation and function, despite unequivocal data supporting the essential role of pathways like CD40-CD154 (CD40 ligand) in GC biology (Laman et al., 1996). If such interactions were to play a role in ELS formation and function, then pathway blockade would be predicted to eliminate established structures in affected tissue and potentially improve organ function. To test this hypothesis, we examined the effect of therapeutic administration of an anti-CD154 monoclonal antibody in the non-obese diabetic (NOD/ShiLtJ) mouse model of secondary SS (Humphreys-Beher et al., 1996), and monitored salivary gland ELS, antibody secreting cells as well as expression of acquaporin-5 (AQP-5), a protein essential for secretory cell function (Delporte et al., 2006).

1. Material and Methods
CD40 Pathway Gene Signature in Salivary Glands

Cryosections of salivary glands from untreated NOD/ShiLtJ mice (Charles River, Germany), were used for gene expression profiling by microarray. Laser capture microdissection was applied to enrich for ELS.

NOD/ShiLtJ Mouse Model of Secondary SS

The NOD/ShiLtJ strain develops type 1 diabetes-like disease in addition to SS-like disease and can therefore be regarded as a model of secondary SS (Humphreys-Beher et al., 1994). 12-week old female NOD/ShiLtJ were randomized in 2 treatment groups (n=15 per group, two experiments): MR1 (Armenian hamster antimouse CD154 IgG) and isotype control (IC, hamster anti-mouse IgG, BioXcell) at 15 mg/kg, intraperitoneally (i.p.), 2×/week for 10 weeks. All procedures were performed according to the Swiss law for animal protection and were approved by the Cantonal Veterinary Office in Basel, Switzerland (Animal License No. BS-2482).

Histopathology and Immunohistochemistry of Spleen and Salivary Glands from NOD/ShiLtJ Mice Three-µm thick paraffin sections of left salivary glands were stained with hematoxylin and eosin (HE). Automated immunohistochemical stainings for CD3, CD45R, CD138, Iba-1, Ki-67 and AQP-5 were performed on Ventana Discovery XT immunostainer (Roche Diagnostics, Switzerland). Spleens from NOD mice were stained with Ki-67.

ELISPOT Assays for Antibody Secreting Cells (ASCs)

Single cell suspensions from salivary glands and spleens were prepared (online Supplementary File), and fresh CD45+ cells were added to pre-coated ELISPOT plates and incubated for 20 hours at 37° C. in the dark. ASC binding to plates were revealed by adding a TMB substrate solution, and the density of spots was measured with an EliSpot Reader "AID classic".

Anti-Ro ELISA

Mouse Anti-SSA/Ro60 was assessed in serum using ELISA kit cat. No. 5710 (Alpha Diagnostic International, Inc. USA) according to the manufacturer's instructions.

2. Results

Upregulation of a B Cell CD40 Gene Signature in Salivary Glands

Microarray analyses was used to identify genes downstream of CD40 in B cells following rCD154 stimulation of primary, human CD19pos B cells, 43 of which could be mapped to murine genes. It was then examined whether the expression of these genes was modulated in salivary gland (SG) tissue from 12- and 24-week old NOD mice. Fourteen genes, including Cd40, Cd80 and Aicda were significantly upregulated in microdissected ELS compared to whole salivary gland (WS) tissue at both time points, suggesting chronic pathway activation (FIG. 26A). Ingenuity Pathway Analysis also indicated that CD40 and CD154 (CD40LG) were amongst the top upstream regulators both at week 12 and 24 (FIG. 26B), and it was possible to demonstrate overlap between CD40 pathway genes upregulated in SGs from NOD/ShiLtJ mice and from patients with pSS (Horvath et al., 2012).

CD40-CD154 Interactions are Essential for ELS Formation

NOD/ShiLtJ mice develop focal cellular infiltrates in SGs at 8-12 weeks of age with 100% incidence that precedes a decline in SG function (Jonsson et al. 2012). The above data suggested chronic CD40 pathway signaling in NOD SG tissue, and this was supported by evidence of CD40 expression by mononuclear cells in inflammatory foci (Roescher et al. 2012). Therefore, it was opted to test the effects of therapeutic CD40-CD154 blockade by dosing the anti-CD154 mAb MR1 at 15 mg/kg bi-weekly starting at 12 weeks of age for ten weeks.

FIG. 26B shows that chronic dosing of MR1 for 10 weeks in NOD/ShiLtJ mice led to a significant reduction in ELS in salivary glands as defined by clusters of Ki67-positive cells. In addition there was a strong reduction in the percentage of SG-resident B and T cells, and macrophages. Histological images indicated that MR1 was able to suppress ELS ten weeks after the start of dosing (FIG. 26C).

Blockade of CD40-CD154 Interactions Inhibits ASC Formation and Autoantibody Production MR1 administration also resulted in a reduction in total IgG (but not IgM) ASCs in spleen, SGs, and bone marrow (FIG. 26B) as well as complete suppression of splenic GCs. Anti-CD154 treated mice also displayed a significant reduction in serum anti-Ro IgG levels, although the frequency of Ro-specific ASCs in salivary glands did not appear to be significantly affected (FIG. 26C).

Blockade of CD40-CD154 Interactions Prevents Loss of AQP-5-Positive Cells

Figure 27A:
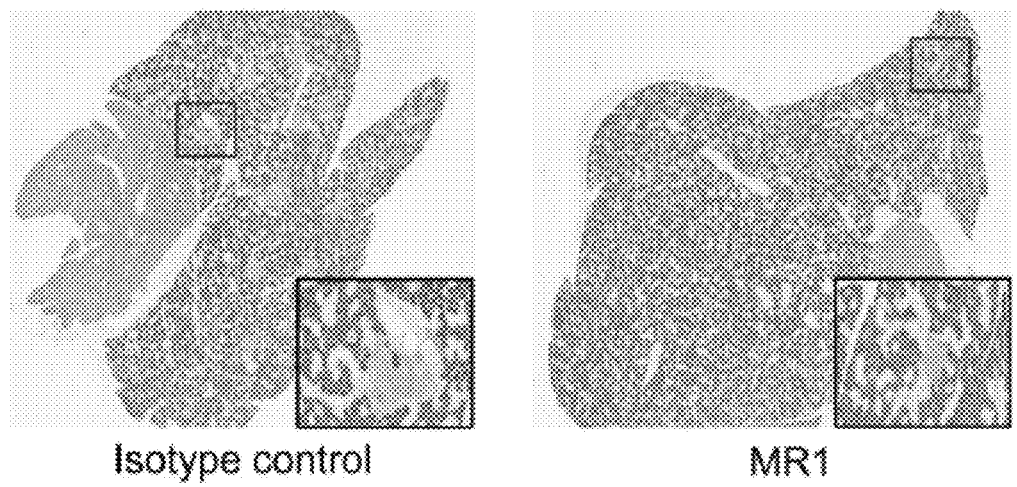
FIGS. 27A and 27B show experimental results; Increased percentage of AQP-5-positive cells in salivary glands of NOD mice after 10-week treatment with anti-CD154.
Figure 27B:
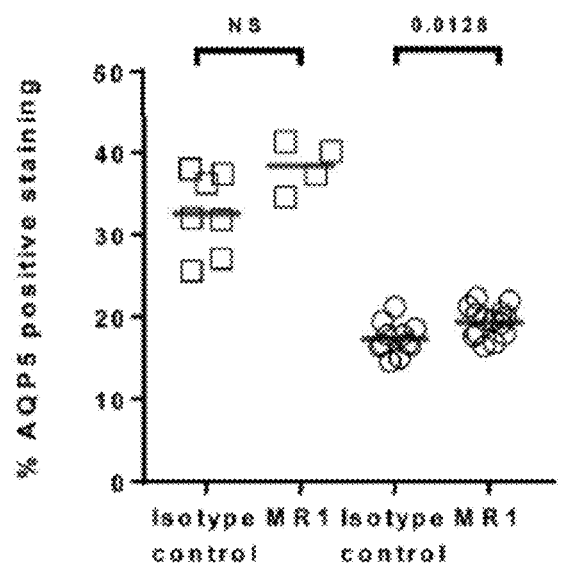

While it is possible to assess stimulated salivary flow in mice, sampling for such analyses requires fasting, anaesthesia and pilocarpine stimulation (Jonsson et al. 2006); factors that can affect animal welfare and interpretation of the read-out. It was therefore opted to monitor expression of AQP-5, a water channel protein involved in regulating production of saliva and tears (Delporte et al., 2006) that has been suggested to be involved in secretory function in SS (Yoshimura et al., 2016). Evaluation of AQP-5 positivity as assessed by IHC staining (FIG. 27), shows a higher percentage of AQP-5 positive cells in MR1-treated compared to control animals, suggesting that CD40-CD154 blockade may prevent or delay loss of salivary gland secretory cell function.

3. Discussion

Evidence of affinity maturation and presence of autoreactive B cells in salivary gland ELS suggests a potential role of these structures in SS pathology (Stott et al., 1998). Given the functional similarities between ELS and GCs, it was hypothesized that immunological costimulatory pathways involved in GC biology may play a similar role in ELS. Deficiency in either CD40 or CD154 prevents GC formation and pharmacological blockade of ligand or receptor also disrupts established GCs (Ristov et al., 2018; Kim et al. 2014). CD40-CD154 interactions have also been implicated in ELS biology, as CD40 expression has been observed on infiltrating cells in SGs glands from pSS patients as well as in NOD mice (Roescher et al. 2012; Ohlsson et al. 2002). Coupled with persistent upregulation of genes downstream of CD40 in ELS from NOD mice as well as in SG biopsies from pSS patients, these data suggested that this costimulatory pathway was active in infiltrating salivary gland leukocytes.

Additionally it was demonstrated that therapeutic blockade of CD40-CD154 interactions led to elimination of ELS, profound reductions in infiltrating leukocytes as well as reductions in serum anti-Ro autoantibody levels, CD40-CD154 blockade also appeared to prevent loss of cells expressing AQP-5, a protein essential for secretory cell function (Delporte et al., 2006), although assessment of saliva production would be a more direct measure of SG function. Previous data indicate that prophylatic administration of a single-dose of MR1 in young NOD mice (4-5 weeks of age; 1-2 months prior to evidence of sialadenitis) could prevent development of sialadenitis and reduce levels of anti-Ro autoantibodies (Mahmoud et al., 2016), consistent with results from CD40-deficient NOD mice. However, it has previously not been shown that therapeutic blockade of CD40-CD154 interactions can abolish SG inflammation, ELS and reduce autoantibody levels in this model.

The data contrast with earlier work where adeno-associated viral expression of a soluble CD40-Ig fusion protein in SGs of NOD mice failed to reduce sialadenitis (Roescher et al., 2012). As the authors reported no evidence of fusion protein expression in SGs, it is likely that concentrations of the drug were insufficient to achieve full CD40-CD154 pathway blockade. In contrast, this study could clearly demonstrate abrogation of splenic GCs suggesting there was sufficient MR1 exposure for a complete, pathway-relevant PD effect in tissue. Collectively, the data suggest that therapeutic blockade of the CD40-CD154 costimulatory pathway with biologics such as the anti-CD40 antibody mAb1 could provide a beneficial therapeutic effect in SS patients (Ristov et al., 2018).

Example 9. Characterization of the In Vitro and In Vivo Properties of CFZ533, a Blocking and Non-Depleting Anti-CD40 Monoclonal Antibody 1. Methods Surface Plasmon Resonance Analysis of Affinity of CFZ533 for CD40

The binding analyses of recombinant CFZ533 were performed at 25° C. with HBS-EP+ as running buffer. A typical binding analysis cycle consisted of three steps: (i) capture of the antibody via ProteinA immobilized on the chip surface, (ii) binding of CD40 antigen to the captured anti-CD40 antibody, and (iii) regeneration of the ProteinA surface. To determine the kinetic rate constants of the antigen-antibody binding interactions, binding data were processed, double referenced with responses from blank injections. The binding curves were fitted locally using the 1:1 interaction model of the Biacore T100 Evaluation software to determine kinetic rate constants. The value for the equilibrium dissociation constant (KD) was calculated as the ratio of the rate constants kd/ka. All binding measurements were performed in two independent experiments.

Surface Plasmon Resonance Analysis of Affinity of CFZ533 for FcγRIIIA

Extracellular domains of human FcγRIIIA tagged with a 4-amino acid purification tag (4APP; Novartis) and an Avi biotinylation tag (GLNDIFEAQKIEWHE; Avidity) were synthesized by Geneart: human FcγRIIIA (CD16a) 158V (Uniprot: P08637, 17-199), human FcγRIIIA 158F (Uniprot: P08637, 17-199), expressed in HEK293 cells and purified with anti-4APP affinity chromatography. Receptors were site directed biotinylated with BirA (Avidity), bound to streptavidin sensor chips (General Electric), and the equilibrium-binding levels of the different Abs were analyzed by surface plasmon resonance (T100, General Electric) as described (Warncke et al. 2012). Equilibrium dissociation constants ($K_D$) were calculated by a 1:1 model.

Human Leukocyte Cultures

Whole blood buffy coats were obtained from healthy volunteers (Blutspendezentrum, Basel, Switzerland) or whole blood collected from healthy volunteers provided under informed consent in accordance with the Swiss Human Research Act and approval of the responsible ethic committee (Ethikkommission Nordwest-und Zentralschweiz; EKNZ). Human tonsil samples were obtained from both Ergolz Klinik (Liestal, Switzerland) (Study Protocol No. 1000244 v.03; approved by Ethikkommission beider Basel; EKBB) and Kantonspital (Liestal, Switzerland) (Study Protocol No. TRI0149 v.01; approved by EKNZ). For in vitro culture experiments, please see supplementary material for detailed methods. Briefly, whole blood, isolated PBMCs, in vitro derived monocyte DCs or human tonsil B cells were incubated with single concentrations or a dose titration of CFZ533 or relevant control antibodies. For pathway blocking experiments, these cultures also included an EC80 concentration of recombinant human CD154 (5 µg/ml) and IL-4 (75 ng/ml). Readouts for in vitro assays included proliferation assessed by thymidine incorporation ($^3$H-TdR), flow cytometric-based assessment of expression of the activation molecule CD69 on B cells, and cytokine secretion assessed by ELISA. Similar assays were used for NHP whole blood and PBMCs. In some human whole blood experiments, CD40 receptor occupancy was also examined by used of a fluorescently tagged CFZ533. Where appropriate, IC50 values were estimated using linear regression-based curve-fitting in GraphPad Prism® software.

In Vitro Cell Depletion Assays

See supplementary material for detailed methods. Briefly, the ability of CFZ533 to mediated depletion of CD20$^{pos}$ B cells was monitored in human whole blood over a period of three days in comparison to the B cell depleting antibody Rituximab. For CDC, CFZ533 or Rituximab were incubated with RAJI B cells in the presence or absence of rabbit complement and cell lysis was assessed by luminescence.

Internalization of CFZ533

Internalization of fluorescently tagged CFZ533 and rCD154 was assessed in vitro using the human B cell line RI-1 (Th'ng et al, 1987). CD40 dependence of CFZ533 internalization was assessed using a CD40 knockout RI-1 cell line. Internalization was assessed using an Amnis® image flow cytometer (Merck KHaA, Damstadt) according to the manufacturer's instructions and data analyzed using ImageStream®$^X$ software.

In Vivo Studies

Single dose pharmacokinetic/pharmacodynamic (PK/PD) studies utilized biologics-treatment naive cynomolgus monkeys (Macaca fascicularis) between 7.5-8.5 years old (6.5±2.6 kg) and captive-bred from Philippines (Siconbrec, Makati City, Philippines). Animal handling, care, drug treatments and blood sampling are performed according to the Swiss Federal Law for animal protection (animal licenses BS #1900, BS #1495). For the recall immunization experiments, we utilized animals from a toxicology study conducted at Covance Laboratories GmbH, Muenster, Germany, (manuscript in preparation). The study was performed according to an authorized study protocol and local standard operating procedures in strict compliance with national legal regulations on animal welfare law and accepted animal welfare standards.

In the PK study, CFZ533 was administered to three animals at calculated single doses of 16.2 (5532), 18.5 (5531) and 20 (5530) mg/kg. Blood was sampled for analyses of CFZ533 serum concentrations, numbers of peripheral T and B lymphocytes, and CD40 occupancy on peripheral B cells by CFZ533. For recall TDAR experiments, animals were immunized with keyhole limpet hemocyanin (KLH) in Alum on study days 8 (priming) and 43 (recall; during CFZ533 treatment) respectively. Serum was sampled one day before and 7, 14 and 21 days after priming and recall immunizations. KLH specific IgM/IgG titers were determined with sandwich ELISA using cynomolgus monkey anti-KLH IgM/IgG reference serum as standard. PK assessment was performed as described above. See supplementary material for additional details on the PK and TDAR experiments.

Histological Analysis of Germinal Centers

Sections of formalin fixed, embedded in paraffin wax (FFPE) spleen and lymph nodes (axillary, mandibular and mesenteric) stained with hematoxylin and eosin as well as with an indirect immune-peroxidase method (HRP+DAB from Dako) with the following markers: anti-CD20 antibody (M0755, Dako), anti-CD8 antibody (RM-9116-SO, Medac) and Ki67 (M7240, Dako). All slides were assessed and graded according to the intensity of the staining (negative to intense). In addition, the staining pattern and distribution of any immunohistochemical stained cells within the tissue were also described.

2. Results

CFZ533 Binds Human CD40 and Inhibits rCD154-Induced Activation of Multiple CD40 Expressing Cell Types Table 3 indicates that the KD of CFZ533 for recombinant human CD40 was determined by surface plasmon resonance as 0.3 nM, thus being very similar to its parental antibody HCD122 (wild-type IgG1 version of CFZ533).

TABLE 3

Binding affinities (KD) and kinetics of HCD122 and CFZ533 to human CD40.

|  | HCD122 | CFZ533 |
|---|---|---|
| $K_D$ [M] | 4.67 ± 1.00 × $10^{-10}$ | 3.05 ± 0.26 × $10^{-10}$ |
| $k_a$ [1/Ms] | 2.84 ± 0.67 × $10^5$ | 3.13 ± 0.73 × $10^5$ |
| $k_d$ [1/s] | 1.26 ± 0.03 × $10^{-4}$ | 0.93 ± 0.14 × $10^{-4}$ |
| $Chi^2[RU^2]$ | 0.17-0.19 | 0.10-0.15 |

FIG. 18A shows effect of CFZ533 on rCD154 and IL-4-mediated proliferation (3H-TdR) of human whole blood cultures, PBMCs, and isolated tonsil B cells from multiple donors (5, 32 and 6 donors respectively). Data is presented as normalized cpm (rCD154+IL-4=100; dotted lines). FIG. 18B shows CFZ533 inhibited TNF-alpha production by rCD154-stimulated moDCs after overnight culture. FIG. 18C shows delayed addition of CFZ533 inhibited rCD154+IL-4 mediated human PBMC proliferation. CFZ533 was added to human PBMCs one hour before, simultaneously with, or two and six hours after stimulation with rCD154+IL-4, and proliferation (3H-TdR) was assessed after a subsequent four days of culture (dotted and dashed lines represent rCD154+IL-4 and cell plus media controls). For all data, the mean and SD of readouts of rCD154-induced stimulation were graphed as a function of log-transformed CFZ533 concentrations. Where appropriate, IC50 values were determined using linear regression based curve-fitting. FIG. 18D shows relationship between CD40 occupancy and pathway blockade by CFZ533. Human whole blood from 10 donors was cultured overnight with rCD154 in presence of a dose titration of CFZ533. The degree of pathway activation (% CD69pos on B cells) and degree of CD40 occupancy (staining with AlexaFlour 488 labeled CFZ533) was evaluated. Open and filled circles indicate the percent of CD40 occupied by CFZ533 and percent CD69pos expressing cells on CD20pos B cells as a function of log-transformed CFZ533 concentration respectively (Mean and SD shown). Dotted and dashed lines represent rCD154-induced CD69 expression and cells plus media control cultures normalized across all donors.

FIG. 18A indicates that CFZ533 completely inhibited rCD154-induced proliferation of human whole blood cultures, PBMCs as well as purified tonsillar B cells from multiple donors with potencies (IC50 values) of 0.024 µg/ml (0.16 nM), 0.017 µg/ml (0.12 nM) and 0.071 µg/ml (0.47 nM) respectively. In addition, we could demonstrate that CFZ533 completely blocked rCD154-induced TNF production by primary monocyte-derived dendritic cells (moDCs) with an IC50 of 0.04 µg/ml (0.27 nM) (FIG. 18B).

As published previously, CFZ533 inhibited rCD154-induced proliferation of PBMCs from Cynomolgus monkeys (Cordoba et al., 2015). CFZ533 inhibited rCD154-induced proliferation of PBMCs from humans, rhesus and cynomolgus animals with similar potency (IC50 of 0.02, 0.03, and 0.01 µg/ml, respectively), and could also bind CD40 on B cells from these species with EC50 values of approximately 0.2 µg/ml, see Table 4.

TABLE 4

Cellular binding and functional properties of CFZ533 in human and NHPs.

|  | Inhibition of rCD154-induced proliferation (IC50 PBMCs) | CD40 occupancy by CFZ533 (MFI EC50 on CD20+ cells) |
|---|---|---|
| Human | 0.017 + 0.012 µg/ml<br>0.12 + 0.08 µM<br>(n = 32) | 0.22 + 0.042 µg/ml<br>1.49 + 0.28 µM<br>(n = 4) |
| Rhesus | 0.026 + 0.017 µg/ml<br>0.18 + 0.12 µM<br>(n = 8) | 0.22 + 0.033 µg/ml<br>1.49 + 0.22 µM<br>(n = 6) |
| Cynomolgus | 0.010 + 0.003 µg/ml<br>0.07 + 0.02 µM<br>(n = 4) | 0.20 + 0.068 µg/ml<br>1.35 + 0.46 µM<br>(n = 4) |

The above cellular data were derived from experiments where CFZ533 was added prior to, or simultaneously with rCD154, indicating that the antibody could prevent binding of the endogenous ligand. We could also demonstrate that addition of CFZ533 up to 6 hours following initiation of leukocyte cultures containing rCD154 resulted in complete inhibition of cellular activation with minimal loss of potency, indicating that CFZ533 could displace the endogenous ligand from CD40 (FIG. 18C).

We also wanted to evaluate the relationship between the degree of CD40 occupancy by CFZ533, and the extent of pathway inhibition. To do so we simultaneously assessed CD40 receptor occupancy by CFZ533 and rCD154-induced CD69 in whole blood from multiple donors. FIG. 18D indicates that CD40 receptor occupancy by CFZ533 of at least 90% was required for complete blockade of CD40 pathway activation. A similar relationship between receptor occupancy and pathway inhibition was also observed using CD23 and CD54 as readouts of CD40 pathway activation (data not shown).

CFZ533 Displays Minimal Stimulatory Potential In Vitro

Figure 19A:
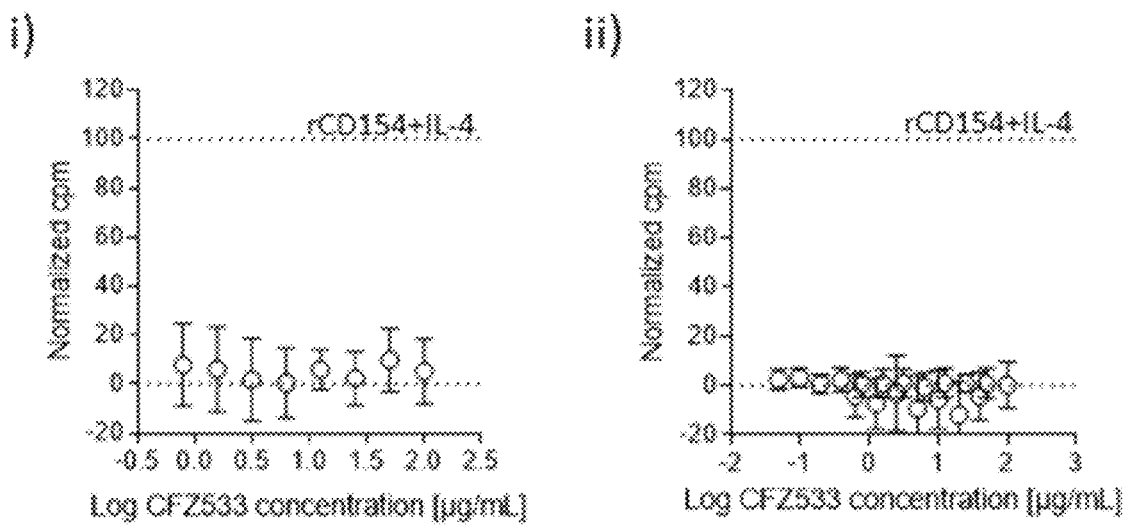
FIGS. 19A, 19B and 19C are graphs showing CFZ533 minimal stimulatory activity in vitro.
Figure 19B:
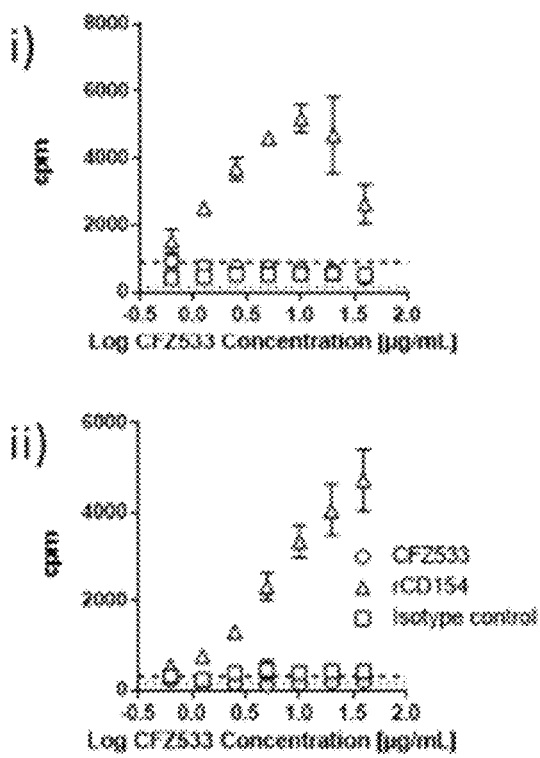
Figure 19C:
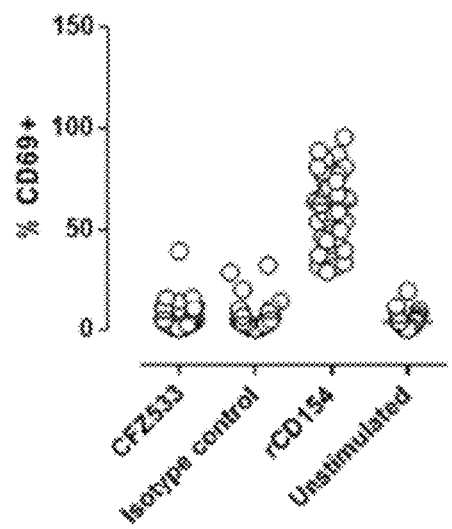

The ability of CFZ533 to stimulate activation of human leukocytes was assessed using proliferation and upregulation of the activation molecule CD69 on B cells in whole blood. FIG. 19A shows data regarding i. Human whole blood from multiple donors (n=13) were incubated with a dose titration of CFZ533, and proliferation (³H-TdR) was assessed after three days of culture. ii. Human PBMCs from multiple donors (n=26) were incubated with a dose titration of CFZ533, and proliferation (³H-TdR) was assessed after three days of culture. For both graphs, data is presented as mean and SD of normalized cpm as a function of log-transformed CFZ533 concentration (rCD154+IL-4=100; dotted lines, cells plus media=0; dashed lines). FIG. 19B shows that CFZ533 does not induce human PBMC proliferation in the presence of additional stimuli. Human PBMCs were stimulated for 3 days with a dose titration of CFZ533 in the presence of IL-4 (i) or anti-IgM F(ab')2. (ii). The mean and SD of 3H-TdR (cpm) is shown as a function of log-transformed CFZ533 concentration. In FIG. 19C it is shown how human whole blood (41 donors) was cultured overnight with no stimuli, CFZ533, isotype control or rCD154 and CD69 expression on B cells was assessed by FACS. Each dot represents data from a single donor with mean % CD69 values indicated by a horizontal red line.

FIG. 19A shows that CFZ533 was unable to induce thymidine incorporation by human whole blood (1:10 dilution) or PBMCs in contrast to rCD154. The inability of CFZ533 to induce proliferation was unaffected by the addition of additional co-stimuli such as IL-4, or anti-IgM (FIG. 19B). We could also demonstrate that CFZ533 was unable to induce upregulation of CD69 on B cells in whole blood from multiple donors, again in contrast to rCD154 (FIG. 19C). Finally, CFZ533 was unable to induce cytokine production by CD40 expressing monocyte-derived DCs or human umbilical vein endothelial cells (HUVECs) (data not shown).

CFZ533 does not Mediate Cell Depletion

CFZ533 was engineered to contain a N297A mutation, previously demonstrated to abrogate FcγR binding resulting in an inability to mediate antibody-dependent cellular cytotoxicity (ADCC). CFZ533 was not able to bind FcγRIIIA in comparison to HCD122 (wild-type IgG1) (Table 5), and we wanted to examine how this lack of binding affected the ability of CFZ533 to mediate cell depletion.

TABLE 5

Binding affinities ($k_a$[1/M]) of HCD122 and CFZ533 to human FcγRIIIA

| FcγR species | HCD122 (wild-type IgG1) | CFZ533 (N297A IgG1) |
|---|---|---|
| Human FcγRIIIA 158V | $1.72 \times 10^6$ | n.d. |
| Human FcγRIIIA 158F | $6.99 \times 10^5$ | n.d. | n.d. not detected

Figure 20A:
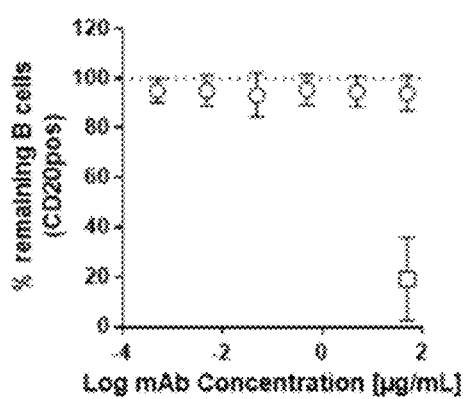
FIGS. 20A and 20B are graphs showing that CFZ533 does not mediate cell depletion in vitro.
Figure 20B:
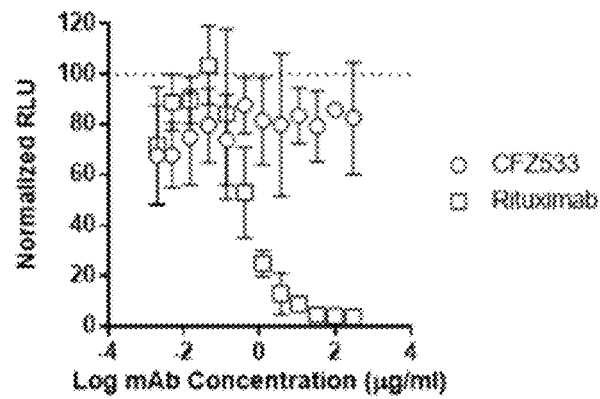

FIG. 20A shows data from human whole blood cultures incubated for 72 hours in the presence of a dose titration of CFZ533 or 50 μg/ml Rituximab. B cells numbers were determined based on CD45pos and CD19pos events falling within lymphocyte FSC/SSC gate. Results for individual antibody concentrations were calculated as percent remaining B cells with reference to untreated samples and graphed as a function of log-transformed antibody concentration (adjusted to 100% and shown as a dotted line). Data represent the mean and SD of eight independent donors. FIG. 20B shows results from Raji B cells incubated with different concentrations of Rituximab or CFZ533 and a fixed concentration of rabbit complement. Concentration dependent killing of the Raji cells was analyzed after 2 hours, where the viability of the cells was measured by determination of the ATP concentration in each well using luciferase. Results are presented as isotype-control normalized relative luciferase units (RLU) as a function of log-transformed antibody concentration.

FIG. 20A indicates that while the depleting anti-CD20 antibody Rituximab was able to eliminate approximately 80% of B cells in human whole blood, while CFZ533 failed to mediate any cell depletion. In addition, CFZ533 was unable to mediate complement-dependent cytotoxicity (CDC) of Raji B cells, in contrast to Rituximab (FIG. 20B).

CFZ533 is Internalized by B Cells in a CD40-Dependent Manner

Figure 21A:
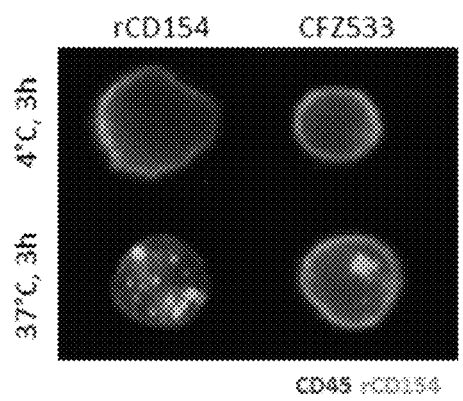
FIGS. 21A, 21B and 21C are representative images of individual RI-1 B cells showing internalization of CD40 receptors upon binding by recCD154 or CFZ533.
Figure 21B:
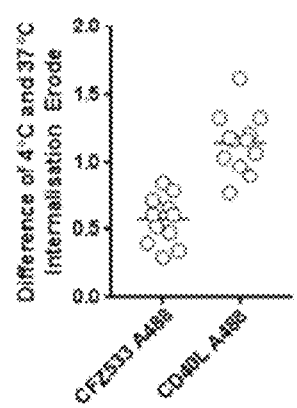

We next wanted to examine whether CFZ533 could be internalized by the CD40 expressing human B cell line RI-1. FIG. 21A indicates that rCD154 was internalized under permissive conditions (37° C.) in comparison to non-permissive conditions (4° C.), where weak staining of rCD154 could be observed on the plasma membrane. CFZ533 was also internalized, although there did appear to be residual membrane staining at 37° C. FIG. 21B indicated that the extent of internalization of rCD154 appeared to be greater than that observed for CFZ533. Using a CD40 knockout RI-1 B cell line, we could demonstrate that binding and internalization of CFZ533 (FIG. 21C) and rCD154 (data not shown) was CD40 dependent.

Figure 21C:
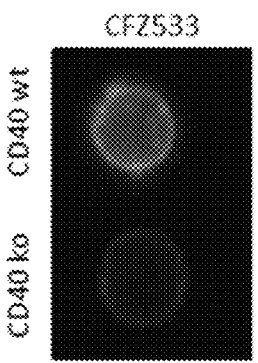

FIG. 21A shows Representative images of individual RI-1 B cells cultured with AlexaFlour 488 labeled rCD154 or CFZ533 for 3 hours at 37° C. or 4° C. FIG. 21B. Relative internalization erode of CFZ533 and rCD154 under permissive conditions (non-permissive erode values subtracted). Each dot represents data from an individual experiment and the population mean is indicated as a horizontal red line. FIG. 21C. Representative images of individual CD40 expressing or CD40 knock-out RI-1 cells cultured with Alexa488 labeled CFZ533 for 3 hours at 37° C. In all experiments, cells were co-stained with AlexaFlour 647 labeled CD45 to demark the cell membrane.

Pharmacokinetic Properties of CFZ533 in Non-Human Primates

Figures 22A, 22B, 22C:
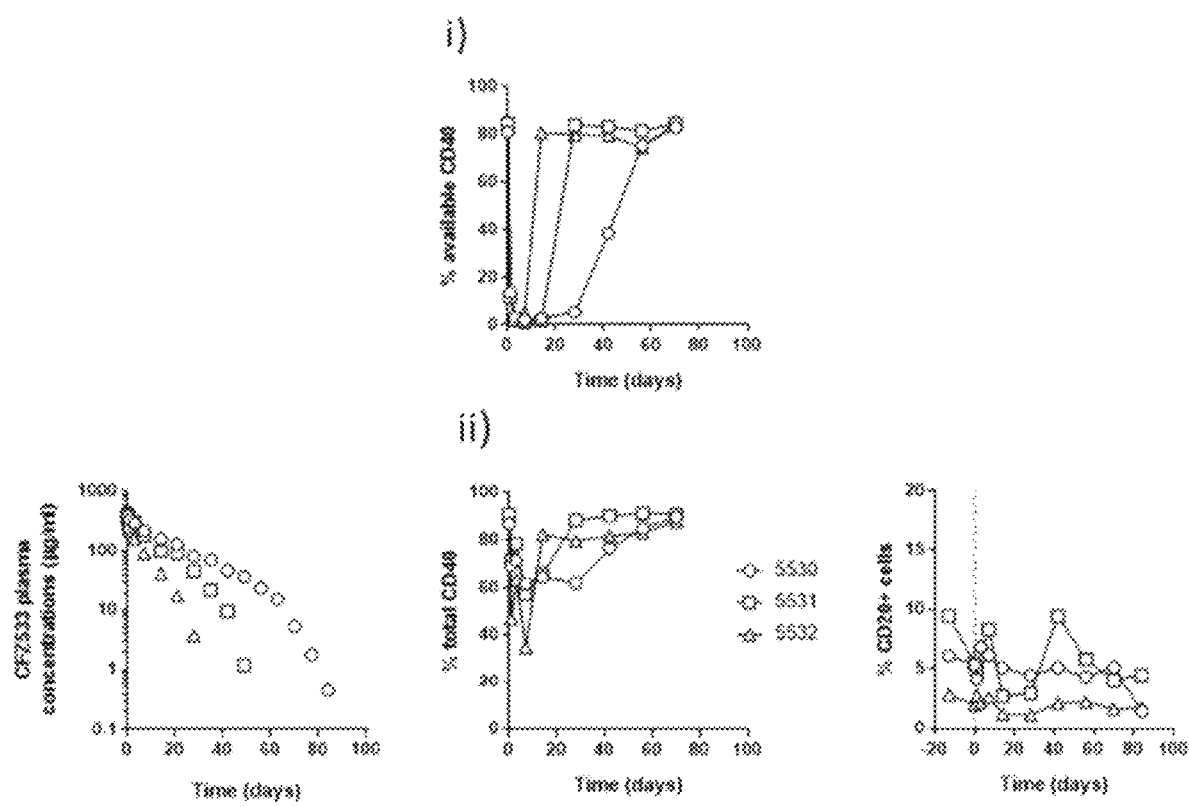
FIGS. 22A, 22B, and 22C are graphs showing the pharmacokinetic and pharmacodynamic (target engagement; no B cell depletion) properties of CFZ533 in non-human primates.

FIG. 22A. Serum concentrations of CFZ533 in three cynomolgus monkeys after single dose administration at calculated doses of 16.2 (5532), 18.5 (5531) and 20 (5530) mg/kg intravenously. FIG. 22B. CD40 occupancy: percent available CD40 (i) and percent total CD40 (ii) C. Peripheral B/T cells: percentage of peripheral blood B cells after single dose. Day 0 is when CFZ533 was administered.

Data above indicated that CFZ533 bound NHP CD40, and could inhibit rCD154-induced activation of NHP B cells with similar potencies. This suggested that cynomolgus and rhesus monkeys would be suitable species for in vivo studies investigating the relationship between CFZ533 PK and PD. Data in FIG. 22A shows the PK profiles of three cynomolgus monkeys following a single intravenous dose of CFZ533 (calculated doses of 16.2, 18.5 and 20 mg/kg). Typical for a monoclonal antibody targeting an internalizing membrane bound antigen (Mager et al. 2006 and Ng et al. 2006), the time course of CFZ533 concentration exhibited clear target-mediated disposition, resulting in non-linear PK profiles and concentration-dependent clearance rate and half-life. The inflection point observed in the PK profiles is a marker of target engagement and is associated with an increased contribution of CD40 to the overall clearance of CFZ533, and a shorter half-life. Further, the inflection point in the PK profiles coincided with the time where a drop of CD40 saturation was observed (FIG. 22B, i). This occurred at approximately 10-20 μg/ml, when CFZ533 was subject to more rapid elimination. In all animals, there was no loss of CD40 receptor expression on cells (FIG. 22B, ii). Further, CFZ533 did not deplete peripheral blood B cells (FIG. 22C) or T cells (data not shown), despite some observed variations throughout the study.

CFZ533 Inhibits Recall T Cell-Dependent Antibody Production

Figure 23A:
FIG. 23A is an experimental design schematic of a PK/PD and vaccination study in non-human primates.
Figure 23B:
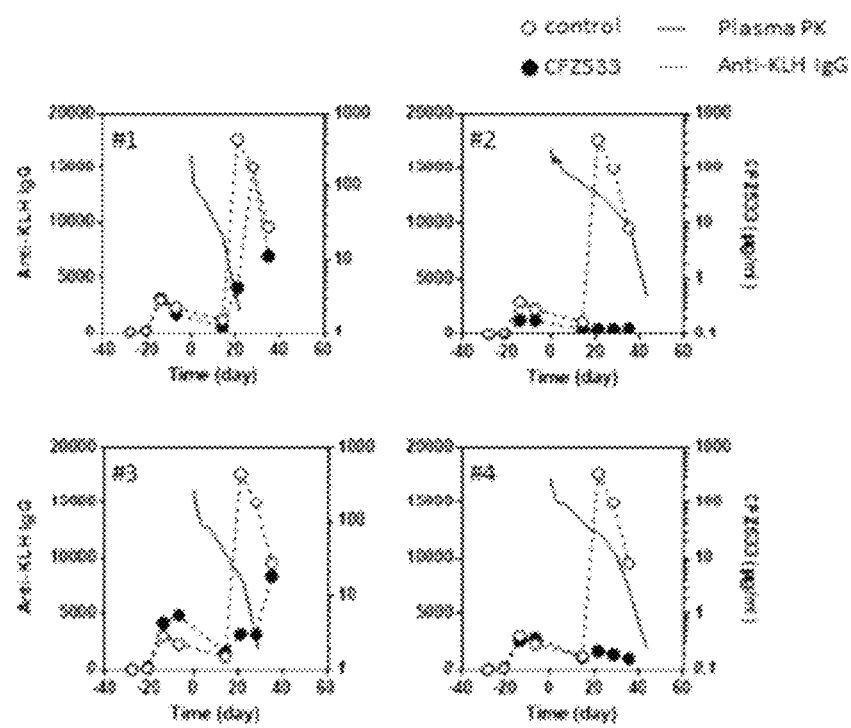
FIG. 23B is graphs showing anti-KLH IgG (immune response) and plasma CFZ533 levels (pharmacokinetics).
Figure 23C:
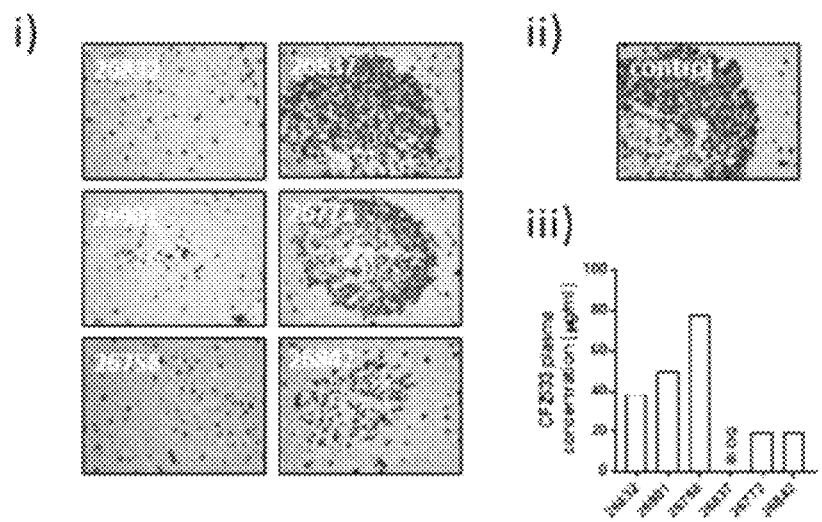
FIG. 23C shows results of a histological analysis of germinal centers.

FIG. 23A shows experimental design schematic for evaluating the effect of CFZ533 on recall TDARs. Arrows below the x-axis highlight primary and secondary KLH immunizations. The timing of a single dose of 10 mg/kg CFZ533 is shown above. The asterisks indicate time points at which anti-KLH IgG and/or CFZ533 levels were measured. FIG. 23B. Each graph shows anti-KLH IgG (closed symbols) and plasma CFZ533 levels (log-scale; unbroken line) for an individual animal. Average anti-KLH IgG levels from control animals (open symbols) are overlaid on each graph for comparative purposes. FIG. 23C. Histological analysis of germinal centers (Ki67 staining) in mLNs from Rhesus monkeys from a 1 mg/kg/week subcutaneous multiple dose 26-week study using CFZ533. Representative mLN sections from six animals are shown (i) along with a control image (ii). iii. Average steady state CFZ533 serum concentrations over a dosing interval from individual animals at the end of the treatment period.

An expected on-target, PD effect of CD40 blocked is inhibition of a TDAR (Kawabe et al. 1994). CFZ533 inhibits primary TDARs in NHPs and humans, and we also wanted to examine the effects of this antibody on a recall TDAR. The experimental design is summarized in FIG. 23A. Briefly, four rhesus monkeys were immunized with KLH in Alum at study day −28 (priming), prior to a single intravenous dose of CFZ533 at 10 mg/kg on study day 1, followed by a second KLH immunization on study day 15.

FIG. 23B illustrates the effects of CFZ533 on anti-KLH IgG recall responses in four individual animals in comparison to data from immunized controls (no CFZ533). There was inter-animal variability in PK profiles of CFZ533, with more rapid elimination of CFZ533 observed in animals #1 and #3. Higher plasma concentrations were observed for a longer period of time in animals #2 and #4. Interestingly, these animals displayed complete suppression of an anti-KLH IgG (and IgM; data not shown) recall response on study day 15 (note all animals mounted a primary TDAR to KLH). In contrast, anti-KLH IgG responses were observed (albeit with some delay) in animals with more rapid clearance of CFZ533 (higher delay for animal #3 as compared to animal #1), notably when serum CFZ533 levels were less than approximately 40 μg/ml at the time of second KLH immunization. As has been observed with previous in vivo experiments with CFZ533 in transplanted (Cordoba et al. 2015) and nontransplanted animals (FIG. 22B), no peripheral B cell depletion was observed (data not shown).

The above results indicated that CFZ533 serum concentrations higher than approximately 40 μg/ml were required for complete suppression of a recall TDAR in NHPs. We wanted to further examine the relationship between CFZ533 exposure and CD40 pathway-relevant tissue pharmacodynamic effects. At the termination of a 26-week toxicology study, at 1 mg/kg/week CFZ533 subcutaneously we performed histological and molecular analysis of GCs in mesenteric lymph nodes (mLNs). FIG. 23C (i) indicates that of the six animals dosed, we could observe complete suppression of GCs in three individuals, whereas GCs could still be observed in the mLNs of the remaining animals. FIG. 23C (iii) indicates that serum concentrations of at least 38 μg/mL (average steady-state concentration over the dosing interval) were associated with complete suppression of GC development in cortical B cell areas of lymph nodes, whereas incomplete (animal 26842) or no suppression (animals 26772 and 26837) of GCs was observed at serum concentrations below 20 μg/mL, despite full CD40 occupancy on whole blood $CD20^{pos}$ B cells (animals 26842 and 26772; data not shown). There was no evidence of peripheral B cell depletion (data not shown).

DISCUSSION

CFZ533 is being developed as a potential therapy for solid organ transplantation and autoimmune diseases associated with dysregulation of the CD40-CD154 co-stimulatory pathway. Here we describe the characterization of the functional properties of CFZ533 in CD40-pathway relevant in vitro and in vivo model systems as well as investigating the relationship between CFZ533 exposure and PD effects.

CFZ533 was able to bind CD40 and completely prevent rCD154-induced pathway activation on different human immune cell types including B cells and DCs. In addition, it appears that in excess of 90% CD40 occupancy was required for CFZ533 to completely block pathway activation in whole blood. Collectively these data suggested that CFZ533 has the potential to block CD40 pathway-dependent effector functions irrespective of cell type, assuming sufficient receptor occupancy was achieved. Our data also indicated that in PBMCs, CFZ533 was able to displace pre-bound rCD154 from CD40 suggesting that the epitopes of the mAb and physiological ligand may overlap; a notion under investigation in structural studies.

In vivo, a concentration-dependent clearance rate and half-life was observed for CFZ533 in single dose PK studies. This PK profile suggested that CD40 receptor expression affected the elimination of CFZ533. At low CFZ533 concentrations (i.e. incomplete target saturation), the contribution of CD40 to the overall clearance of CFZ533 was elevated and the half-life was somewhat shorter than usually observed for IgG1 type antibodies. At higher concentrations corresponding to complete target saturation (and full functional pathway inhibition), the contribution of the receptor to the overall clearance of CFZ533 was limited and the half-life was increased. The target-mediated clearance of CFZ533 was consistent with CD40-mediated internalization of CFZ533 observed in vitro, that is likely followed by lysosomal degradation of the complex.

An additional finding from the PK/PD studies confirmed the inability of CFZ533 to deplete peripheral B cells in vivo (Cordoba et al. 2015). As mentioned, the inability of CFZ533 to deplete CD40 expressing cells is due to the presence of a N297A mutation in the antibody leading to the absence of N-linked glycosylation in the hinge region, rendering it unable to bind FcγRIIIA or mediate ADCC or CDC. Fc-silencing of CFZ533 was done to prevent depletion of CD40-expressing cell types; of particular concern given the broad tissue distribution of this receptor on immune and non-immune cell types, particularly under inflammatory conditions.

In addition to efficacy in NHP renal transplantation (Cordoba et al. 2015), results in this paper indicated that CFZ533 completely inhibited recall TDARs. This result suggested that memory B cell responses to T cell-dependent antigens were fully dependent on CD40-CD154 interactions. The extent of inhibition of the recall response appeared to be related to the concentration of CFZ533, with serum levels in excess of 30-40 μg/ml (for at least a week after boosting) being required for full suppression of an antigen-specific antibody response. This relationship between serum concentration and a CD40 pathway-relevant tissue PD readout also held when examining the effect of CFZ533 on mesenteric lymph node GCs, where a minimum threshold of average, steady-state serum CFZ533 concentrations was required for complete suppression of GCs. These data point to the importance of establishing a relationship between peripheral drug exposures and a target-relevant PD effect in tissue in order to inform dosing strategies. Several biologics targeting the CD40-CD154 costimulation pathway are being developed for various autoimmune diseases. In addition to anti-CD40 mAbs like CFZ533, anti-CD154 mAbs remain in the clinic, despite the potential risk for thromboembolic events (Boumpas et al., 2003). Recent results have suggested that Fc-silencing and pegylated F(ab')2 approaches may eliminate the thromboembolic liabilities of antibodies targeting CD154, however there are reports that Fc-silent anti-CD154 mAbs may be less efficacious. To date there is no evidence of thromboembolic events as sociated with administration of multiple anti-CD40 antibodies in preclinical models or in the clinic.

In conclusion, our data indicate that CFZ533 is a pathway blocking, non-depleting anti-CD40 antibody with minimal agonistic properties. At sufficient, pharmacologically relevant exposures, CFZ533 is able to completely inhibit recall TDARs as well as suppress germinal centers without depleting CD40 expressing cell types. These data, combined with preclinical efficacy in kidney transplantation provide solid scientific rationale for the potential clinical utility of CFZ533 in select autoimmune diseases and solid organ transplantation.

REFERENCES

Bombardieri M, Pitzalis C. Ectopic lymphoid neogenesis and lymphoid chemokines in Sjogren's syndrome: at the interplay between chronic inflammation, autoimmunity and lymphomagenesis. Curr Pharm Biotechnol. 2012 August; 13(10):1989-1996.

Bombardieri M, Barone F, Lucchesi D, Nayar S, van den Berg W B, Proctor G, et al. Inducible tertiary lymphoid structures, autoimmunity, and exocrine dysfunction in a novel model of salivary gland inflammation in C57BL/6 mice. J Immunol. 2012 Oct. 1; 189(7):3767-3776.

Bombardieri M, Lewis M, Pitzalis C. Ectopic lymphoid neogenesis in rheumatic autoimmune diseases. Nat Rev Rheumatol. 2017 March; 13(3):141-154.

Boumpas D T, Furie R, Manzi S, Illei G G, Wallace D J, Balow J E et al. A short course of BG9588 (anti-CD40 ligand antibody) improves serologic activity and decreases hematuria in patients with proliferative lupus glomerulonephritis. Arthritis Rheum 2003; 48(3):719-727.

Cordoba F, Wieczorek G, Audet M, Roth L, Schneider M A, Kunkler A et al. A novel, blocking, Fcsilent anti-CD40 monoclonal antibody prolongs nonhuman primate renal allograft survival in the absence of B cell depletion. Am J Transplant 2015; 15(11):2825

Dimitriou I D, Kapsogeorgou E K, Moutsopoulos H M, et al (2002) CD40 on salivary gland epithelial cells: high constitutive expression by cultured cells from Sjögren's syndrome patients indicating their intrinsic activation. Clin Exp Immunol; 127(2):386-92.

Delporte C, Steinfeld S. Distribution and roles of aquaporins in salivary glands. Biochim Biophys Acta. 2006 August; 1758(8):1061-1070. Harland R, Klintmalm G, Yang H, et al. (2015) ASKP1240 in De Novo Kidney Transplant Recipients. Am J Transplant; 15(S3): Abstract #3012.

Horvath S, Nazmul-Hossain A N, Pollard R P, Kroese F G, Vissink A, Kallenberg C G, et al. Systems analysis of primary Sjögren's syndrome pathogenesis in salivary glands identifies shared pathways in human and a mouse model. Arthritis Res Ther. 2012 Nov. 1; 14(6):R238.

Jacobi A M, Hansen A, Kaufmann O, Pruss A, Burmester G R, Lipsky P E, et al. Analysis of immunoglobulin light chain rearrangements in the salivary gland and blood of a patient with Sjögren's syndrome. Arthritis Res. 2002; 4(4):R4.

Jonsson M V, Delaleu N, Brokstad K A, Berggreen E, Skarstein K. Impaired salivary gland function in NOD mice: association with changes in cytokine profile but not with histopathologic changes in the salivary gland. Arthritis Rheum. 2006 July; 54(7):2300-2305.

Kaufman I, Schwartz D, Caspi D, et al (1999) Sjögren's syndrome—not just Sicca: renal involvement in Sjögren's syndrome. Ann Rheum Dis.58:253-6.

Kawabe T, Naka T, Yoshida K, Tanaka T, Fujiwara H, Suematsu S et al. The immune responses in CD40-deficient mice: impaired immunoglobulin class switching and germinal center formation. Immunity 1994; 1(3):167-178.

Kim E J, Kwun J, Gibby A C, Hong J J, Farris A B, 3rd, Iwakoshi N N, et al. Costimulation blockade alters germinal center responses and prevents antibody-mediated rejection. Am J Transplant. 2014 January; 14(1):59-69.

Komaroff A L, Fagioli L R, Doolittle T H, et al (1996) Health status in patients with chronic fatigue syndrome and in general population and disease comparison groups. Am J Med; 101:281-90.

Kuenstner S, Langelotz C, Budach V, et al (2002) The comparability of quality of life scores. A multitrait multimethod analysis of the EORTC QLQ-C30, SF-36 and FLIC questionnaires. Eur J Cancer; 38:339-48.

Laman J D, Claassen E, Noelle R J. Functions of CD40 and its ligand, gp39 (CD40L). Crit Rev Immunol. 1996; 16(1):59-108.

Mager D E. Target-mediated drug disposition and dynamics. Biochem Pharmacol 2006; 72(1):1-10.

Mahmoud T I, Wang J, Kamell J L, Wang Q, Wang S, Naiman B, et al. Autoimmune manifestations in aged mice arise from early-life immune dysregulation. Sci Transl Med. 2016 Oct. 19; 8(361):361ra137.

Manganelli P and Fietta P (2003) Apoptosis and Sjögren syndrome. Semin Arthritis Rheum; 33(1):49-65.

Meijer J M, Meiners P M, Vissink A, et al (2010) Effectiveness of rituximab treatment in primary Sjögren's syndrome: a randomized, double-blind, placebo-controlled trial. Arthritis Rheum; 62:960-8.

Moerman R V, Arends S, Meiners P M, et al (2014) EULAR Sjögren's Syndrome Disease Activity Index (ESSDAI) is sensitive to show efficacy of rituximab treatment in a randomized controlled trial. Ann Rheum Dis; 73:472-4.

Ng C M, Stefanich E, Anand B S, Fielder P J, Vaickus L. Pharmacokinetics/pharmacodynamics of nondepleting anti-CD4 monoclonal antibody (TRX1) in healthy human volunteers. Pharm Res 2006; 23(1):95-103.

Ohlsson M, Szodoray P, Loro L L, Johannessen A C, Jonsson R. CD40, CD154, Bax and Bcl-2 expression in Sjögren's syndrome salivary glands: a putative anti-apoptotic role during its effector phases. Scand J Immunol. 2002 December; 56(6):561-571.

Ristov J, Espie P, Ulrich P, Sickert D, Flandre T, Dimitrova M, et al. Characterization of the in vitro and in vivo properties of CFZ533, a blocking and non-depleting anti-CD40 monoclonal antibody. Am J Transplant. 2018 Apr. 17.

Roescher N, Lodde B M, Vosters J L, Tak P P, Catalan M A, Illei G G, et al. Temporal changes in salivary glands of non-obese diabetic mice as a model for Sjögren's syndrome. Oral Dis. 2012 January; 18(1):96-106.

Roescher N, Vosters J L, Lai Z, Uede T, Tak P P, Chiorini J A. Local administration of soluble CD40:Fc to the salivary glands of non-obese diabetic mice does not ameliorate autoimmune inflammation. PLoS One. 2012; 7(12): e51375.

Segal B, Bowman S J, Fox P C, et al (2009) Primary Sjögren's Syndrome: health experiences and predictors of health quality among patients in the United States. Health Qual Life Outcomes; 7:46.

Sellam J, Proulle V, Jüngel A, et al (2009) Increased levels of circulating microparticles in primary Sjögren's syndrome, systemic lupus erythematosus and rheumatoid arthritis and relation with disease activity. Arthritis Res Ther; 11:R156.

Seror R, et al (2011a) EULAR Sjogren's syndrome disease activity index: development of a consensus systemic disease activity index for primary Sjogren's syndrome. Ann Rheum Dis.; 69(6): 1103-9.

Seror R, et al (2011b) EULAR Sjögren's Syndrome Patient Reported Index (ESSPRI): development of a consensus patient index for primary Sjögren's syndrome. Ann Rheum Dis.; 70(6):968-72.

Stott D I, Hiepe F, Hummel M, Steinhauser G, Berek C. Antigen-driven clonal proliferation of B cells within the target tissue of an autoimmune disease. The salivary glands of patients with Sjogren's syndrome. J Clin Invest. 1998 Sep. 1; 102(5):938-946.

Tishler M, Yaron I, Shirazi I, et al (2008) Hydroxychloroquine treatment for primary Sjögren's syndrome: its effect on salivary and serum inflammatory markers. Scand J Rheumatol. 37:213-8.

Th'ng K H, Garewal G, Kearney L, Rassool F, Melo J V, White H et al. Establishment and characterization of three new malignant lymphoid cell lines. Int J Cancer 1987; 39(1):89-93.

Vossenkämper A, Lutalo P M, Spencer J (2012) Translational mini-review series on B cell subsets in disease. Transitional B cells in systemic lupus erythematosus and Sjögren's syndrome: clinical implications and effects of B cell-targeted therapies. Clin Exp Immunol; 167:7-14.

Voulgarelis M, Moutsopoulos H M. Mucosa-associated lymphoid tissue lymphoma in Sjogren's syndrome: risks, management, and prognosis. Rheum Dis Clin North Am. 2008 November; 34(4):921-933, viii.

Warncke M, Calzascia T, Coulot M, Balke N, Touil R, Kolbinger F et al. Different adaptations of IgG effector function in human and nonhuman primates and implications for therapeutic antibody treatment. J Immunol 2012; 188(9):4405-4411.

Winzer M, Aringer M. (2010) Use of methotrexate in patients with systemic lupus erythematosus and primary Sjögren's syndrome. Clin Exp Rheumatol. 28 (5 Suppl 61):S156-9.

Yoshimura S, Nakamura H, Horai Y, Nakajima H, Shiraishi H, Hayashi T, et al. Abnormal distribution of AQP5 in labial salivary glands is associated with poor saliva secretion in patients with Sjogren's syndrome including neuromyelitis optica complicated patients. Mod Rheumatol. 2016; 26(3):384-390.

The invention claimed is:

1. A method of treating primary Sjogren's syndrome in a human subject, comprising administering a therapeutically effective dose of anti-CD40 antibody to said subject, wherein the antibody is administered through a loading dosing and a maintenance dosing, wherein the loading dosing is administered in three weekly (Q1W) subcutaneous injections starting with a 600 mg antibody at week 1 followed by two Q1W subcutaneous injections of about 150 mg to about 600 mg antibody at week 2 and 3, and the maintenance dosing is subcutaneously administered biweekly (Q2W) in an amount of between about 150 mg to 600 mg antibody starting at week 5, and wherein the antibody
   comprises the heavy chain amino acid sequence of SEQ ID NO: 9 and the light chain amino acid sequence of SEQ ID NO: 10; or the heavy chain amino acid sequence of SEQ ID NO: 11 and the light chain amino acid sequence of SEQ ID NO: 12.

2. The method according to claim 1, wherein the antibody is administered together with one or more pharmaceutically acceptable carriers.

3. The method according to claim 2, wherein the loading dosing is three weekly (Q1W) 600 mg antibody injections at week 1, 2, and 3 and the maintenance dosing is Q2W injections of 150 mg, 300 mg or 600 mg antibody beginning at week 5.

4. The method according to claim 3, wherein the antibody comprises a heavy chain having the amino acid sequence set forth in SEQ ID NO. 9 and a light chain having the amino acid sequence set forth in SEQ ID NO. 10.

5. The method according to claim 1, wherein at least two subcutaneous injections of the loading dosing are different doses.

6. The method according to claim 1, wherein the loading dosing is administered in three weekly (Q1W) subcutaneous injections of 600 mg antibody on weeks 1, 2, and 3, and the maintenance dosing is administered every two weeks (Q2W) beginning on week 5 as subcutaneous injections of 600 mg antibody.

7. The method according to claim 6, wherein the antibody comprises a heavy chain having the amino acid sequence set forth in SEQ ID NO. 9 and a light chain having the amino acid sequence set forth in SEQ ID NO. 10.

8. The method according to claim 1, wherein the loading dosing is administered in three weekly (Q1W) subcutaneous injections of 600 mg antibody on week 1, 300 mg antibody on week 2, and 300 mg antibody on week 3, and the maintenance dosing is administered every two weeks (Q2W) beginning on week 5 as subcutaneous injections of 300 mg antibody.

9. The method according to claim 8, wherein the antibody comprises a heavy chain having the amino acid sequence set forth in SEQ ID NO. 9 and a light chain having the amino acid sequence set forth in SEQ ID NO. 10.

10. The method according to claim 1, wherein the loading dosing is administered in three weekly (Q1W) subcutaneous injections of 600 mg antibody on week 1, 150 mg antibody on week 2, and 150 mg antibody on week 3, and the maintenance dosing is administered every two weeks (Q2W) beginning on week 5 as subcutaneous injections of 150 mg antibody.

11. The method according to claim 10, wherein the antibody comprises a heavy chain having the amino acid sequence set forth in SEQ ID NO. 9 and a light chain having the amino acid sequence set forth in SEQ ID NO. 10.

12. The method according to claim 1, wherein the antibody comprises a heavy chain having the amino acid sequence set forth in SEQ ID NO. 9 and a light chain having the amino acid sequence set forth in SEQ ID NO. 10.

* * * * *